US006426070B1

(12) United States Patent
Rosenberg et al.

(10) Patent No.: US 6,426,070 B1
(45) Date of Patent: Jul. 30, 2002

(54) METHODS FOR INACTIVATING ENVELOPED RNA VIRUS PARTICLES AND COMPOSITIONS FOR USE THEREWITH

(75) Inventors: Helene F. Rosenberg, Bethesda, MD (US); Joseph B. Domachowske, Syracuse, NY (US)

(73) Assignee: The United States as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/446,959

(22) PCT Filed: Jul. 2, 1998

(86) PCT No.: PCT/US98/13852

§ 371 (c)(1),
(2), (4) Date: May 9, 2000

(87) PCT Pub. No.: WO99/01152

PCT Pub. Date: Jan. 14, 1999

Related U.S. Application Data

(60) Provisional application No. 60/052,986, filed on Jul. 2, 1997.

(51) Int. Cl.$^7$ ...................... A61K 38/47; A61K 39/155; A61K 35/14; A61K 38/16; G01N 33/86

(52) U.S. Cl. ............................... 424/94.61; 424/185.1; 424/211.1; 436/69.2; 436/238; 530/350; 530/380

(58) Field of Search .............................. 424/94.6, 184.1, 424/185.1; 436/69.1, 69.2, 236, 238; 530/390.1, 350, 380

(56) References Cited

FOREIGN PATENT DOCUMENTS

| DE | 40 24 530 A1 | 2/1992 |
|---|---|---|
| EP | 0 502 718 A1 | 9/1992 |
| JP | 10117777 A | 5/1998 |
| SU | 1232263 A | 5/1986 |
| WO | WO 98/03669 | 1/1998 |
| WO | WO 98/34637 | 8/1998 |

OTHER PUBLICATIONS

Kita et al. 1995. Eosinophil major basic protein induces degranulation and IL–8 production by human eosinophils. Journal of Immunology. vol. 154, pp. 4749–4758.*

Ackerman, S. et al., "Comparative Toxicity of Purified Human Eosinophil Granule Cationic Proteins for Schistosomula of *Schistosoma Mansoni*", *The American Journal of Tropical Medicine and Hygiene*, vol. 34, No. 4, pp. 735–745 (Jul. 1985).

Ackerman, S., "Characterization and Functions of Eosinophil Granule Proteins", *Eosinophils Biological and Clinical Aspects*, CRC Press, Inc., Boca Raton, FL, pp. 33–74 (1993).

Barker, R. et al., "Eosinophil Cationic Protein cDNA Comparison with Other Toxic Cationic Proteins and Ribonucleases", *The Journal of Immunology*, vol. 143, No. 3, pp. 952–955 (Aug. 1, 1989).

Begun, D., "Origin and Evoluation of a New Gene Descended From alcohol dehydrogenase in Drosophila", *Genetics*, vol. 145, No. 2, pp. 375–382 (Feb. 1997).

Beintema, J., "Presence of a basic amino acid residue at either position 66 or 122 is a condition for enzymic activity in the ribonuclease superfamily", *FEBS Letters*, vol. 254, Nos. 1 and 2, pp. 1–4 (Aug. 28, 1989).

Burrows, B. et al., "The Relationship of Childhood Respiratory Illness to Adult Obstructive Airway Disease", *American Review of Respiratory Disease*, vol. 115, No. 5, pp. 751–760 (May 1977).

Chin, J. et al., "Field Evaluation of a Respiratory Syncytial Virus Vaccine and a Trivalent Parainfluenza Virus Vaccine in a Pediatric Population", *The American Journal of Epidemiology*, vol. 89, No. 4, pp. 449–463 (1969).

Cirino, N. et al., "Targeting RNA decay with 2',5' oligoadenylate–antisense in respiratory syncytial virus–infected cells", Proceedings of the National Academy of Sciences of the United States of America, vol. 94, No. 5, pp. 1937–1942 (Mar. 1997).

Cohen, A. et al., "Eosinophilia in Patients Infected with Human Immunodeficiency Virus", *The Journal of Infectious Diseases*, vol. 174, No. 3, pp. 615–618 (Sep. 1996).

Collins, P. et al., "Respiratory Syncytial Virus", *Fields Virology*, Third Edition, vol. 1, pp. 1313–1351 (1996).

Colocho Zelaya, E.A. et al., "Eosinophil cationic protein in nasopharyngeal secretions and serum of infants infected with respiratory syncytial virus", *Pediatric Allergy and Immunology*, vol. 5, No. 2, pp. 100–106 (May 1994).

Deming, M. et al., "Ribonuclease k6: Chromosomal Mapping and Divergent Rates of Evolution within the RNase A Gene Superfamily", *Genome Research*, vol. 8, No. 6, pp. 599–607 (Jun. 1998).

Domachowske, J. et al., "Recombinant Human Eosinophil–Derived Neurotoxin (rhEDN) is an Effective Antiviral Agent Against Respiratory Syncytial Virus in Vitro", *Clinical Infectious Diseases*, vol. 25, No. 2, pp. 355 (Aug. 1997).

(List continued on next page.)

*Primary Examiner*—Mary E. Mosher
*Assistant Examiner*—Shanon A. Foley
(74) *Attorney, Agent, or Firm*—Merchant & Gould P.C.

(57) ABSTRACT

A method for inactivating a virion of an enveloped RNA virus comprising contacting the virion with an eosinophil-derived ribonuclease, such as eosinophil-derived neurotoxin (EDN) or eosinophil cationic protein (ECP). The invention also provides methods for treating a subject infected by an enveloped RNA virus and for preventing infection by an enveloped RNA virus comprising administering an effective amount of an eosinophil-derived ribonuclease, such as EDN or ECP. The invention also provides a composition comprising an effective amount of an eosinophil-derived ribonuclease and an acceptable carrier.

15 Claims, 26 Drawing Sheets

OTHER PUBLICATIONS

Domachowske, J. et al., "Eosinophils inhibit retroviral transduction of human target cells by a ribonuclease–dependent mechanism", *Journal of Leukocyte Biology*, vol. 62, No. 3, pp. 363–368 (Sep. 1997).

Domachowske, J. et al., "Recombinant Human Eosinophil–Derived Neurotoxin/RNase 2 Functions as an Effective Antiviral Agent against Respiratory Syncytial Virus", *The Journal of Infectious Diseases*, vol. 177, No. 6, pp. 1458–1464 (Jun. 1998).

Durack, D. et al., "Neurotoxicity of human eosinophils", Proceedings of the National Academy of Sciences of the United States of America, vol. 76, No. 3, pp. 1443–1447 (Mar. 1979).

Durack, D. et al., "Purification of human eosinophil–derived neurotoxin", *Proceedings of the National Academy of Sciences of the United States of America*, vol. 78, No. 8, pp. 5165–5169 (Aug. 1981).

Dyer, K. et al., "Eosinophil Charcot–Leyden Crystal Protein Binds to Beta–Galactoside Sugars", *Life Sciences*, vol. 58, No. 23, pp. 2073–2082 (May 3, 1996).

Falsey, A. et al., "Respiratory Syncytial Virus and Influenza A Infections in the Hospitalized Elderly", *The Journal of Infectious Diseases*, vol. 172, No. 2, pp. 389–394 (Aug. 1995).

Freireich, E. et al., "Quantitative Comparison of Toxicity of Anticancer Agents in Mouse, Rat, Hamster, Dog, Monkey, and Man", *Cancer Chemotherapy Reports*, vol. 50, No. 4, pp. 219–244 (May 1966).

Fukada, T. et al., "Calcium Ionophore A23187 Calcium–Dependent Cytolytic Degranulations in Human Eosinophils", *The Journal of Immunology*, vol. 135, No. 2, pp. 1349–1356 (Aug. 1985).

Garofalo, R. et al., "Eosinophil degranulation in the respiratory tract during naturally acquired respiratory syncytial virus infection", *The Journal of Pediatrics*, vol. 120, No. 1 pp. 28–32 (Jan. 1992).

Gleich, G. et al., "Biochemical and functional similarities between human eosinophil–derived neurotoxin and eosinophil cationic protein: Homology with ribonuclease",Proceedings of the National Academy of Sciences of the United States of America, vol. 83, No. 10, pp. 3146–3150 (May 1986).

Gleich, G. et al., "Eosinophils", *Inflammation Basic Principles and Clinical Correlates*, Raven Press, Ltd., New York, pp. 663–700 (1992).

Goodman, M. et al., "Darwinian evolution in the genealogy of haemoglobin", *Nature*, vol. 253, No. 5493, pp. 603–608 (Feb. 20, 1975).

Gordon, M., "Remarks on Hodgkins's Disease, A Pathogenic Agent in the Glands, and its Application in Diagnosis", *The British Medical Journal*, vol. 1, pp. 641–644 (Apr. 15, 1933).

Graur, D., "Amino Acid Composition and the Evolutionary Rates of Protein–Coding Genes", *Journal of Molecular Evolution*, vol. 22, pp. 53–62 (1985).

Gu, X. et al., "A Model for the Correlation of Mutation Rate with GC Content and the Origin of GC–Rich Isochores", *Journal of Molecular Evolution*, vol. 38, No. 5, pp. 468–475 (May 1994).

Gullberg, U. et al., "The Cytotoxic Eosinophil Cationic Protein (ECP) has Ribonuclease Activity", *Biochemical and Biophysical Research Communications*, vol. 139, No. 3, pp. 1239–1242 (Sep. 30, 1986).

Herndon, F. et al., "Depletion of Eosinophils by Anti–IL–5 Monoclonal Antibody Treatment of Mice Infected with *Trichinella spiralis* Does not Alter Parasite Burden or Immunologic Resistance to Reinfection", *The Journal of Immunology*, vol. 149, No. 11, pp. 3642–3647 (Dec. 1, 1992).

Hofsteenge, J., "Ribonuclease Inhibitor", *Ribonucleases Structures and Functions*, pp. 621–658 (1997).

Ide, M. et al., "Ammonium chloride exposure inhibits cytokine–mediated eosinophil survival", *Journal of Immunological Methods*, vol. 168, No. 2, pp. 187–196 (1994).

Iwama, M. et al., "Purification and Properties of Human Urine Ribonucleases", *The Journal of Biochemistry*, vol. 89, No. 4, pp. 1005–1016 (Apr. 1981).

Kim, H. et al., "Respiratory Syncytial Virus Disease in Infants Despite Prior Administration of Antigenic Inactivated Vaccine", *The American Journal of Epidemiology*, vol. 89, No. 4, pp. 422–434 (1969).

Kimpen, J. et al., "Activation of Human Eosinophils In Vitro by Respiratory Syncytial Virus", *Pediatric Research*, vol. 32, No. 2, pp. 160–164 (Aug. 1992).

Klebanoff, S. et al., "Virucidal Effect of Stimulated Eosinophils on Human Immunodeficiency Virus Type 1", *AIDS Research and Human Retroviruses*, vol. 12, No. 1, pp. 25–29 (Jan. 1, 1996).

Kroegel, C. et al., "Characterization of Eosinophil Cell Activation by Peptides Differential Effects of Substance P, Melittin, and FMET–Leu–Phe", *The Journal of Immunology*, vol. 145, No. 8, pp. 2581–2587 (Oct. 15, 1990).

Lehrer, R. et al., "Direct Inactivation of Viruses by MCP–1 and MCP–2, Natural Peptide Antibiotics from Rabbit Leukocytes", *Journal of Virology*, vol. 54, No. 2, pp. 467–472 (May 1985).

Lehrer, R. et al., "Antibacterial Properties of Eosinophil Major Basic Protein and Eosinophil Cationic Protein", *The Journal of Immunology*, vol. 142, No. 12, pp. 4428–4434 (Jun. 15, 1989).

Leonidas, D. et al., "Crystal structure of human Charcot–Leyden crystal protein, an eosinophil lysophospholipase, identifes it as a new member of the carbohydrate–binding family of galectins", *Structure*, vol. 3, No. 12, pp. 1379–1393 (1995).

Li, W. et al., *Fundamentals of Molecular Evolution*, Sinauer Associates, Inc., Sutherland, Massachusetts, (1991).

Li, W. et al., "A New Method for Estimating Synonymous and Nonsynonymous Rates of Nucleotide Substitution Considering the Relative Likelihood of Nucleotide and Codon Changes", *Molecular Biology and Evolution*, vol. 2, No. 2, pp. 150–174 (Mar. 1985).

Li, W., "Unbiased Estimation of the Rates of Synonymous and Nonsynonymous Substitution", *Journal of Molecular Evolution*, vol. 36, No. 1, pp. 96–99 (Jan. 1993).

Long, M. et al., "Natural Selection and the Origin of jingwei, a Chimeric Processed Functional Gene in Drosophila", *Science*, vol. 260, pp. 91–95 (Apr. 2, 1993).

Martin, E. et al., "Defensins and other endogenous peptide antibiotics of vertebrates",*Journal of Leukocyte Biology*, vol. 58, No. 2, pp. 128–136 (Aug. 1995).

Mitra, A. et al., "A mammalian 2–5A system functions as an antiviral pathway in transgenic plants", Proceedings of the National Academy of Sciences of the United States of America, vol. 93, No. 13, pp. 6780–6785 (Jun. 25, 1996).

Molina, H. et al., "Toxic Effects Produced or Mediated by Human Eosinophil Granule Components on Trypanosoma Cruzi", *The American Journal of Tropical Medicine and Hygiene*, vol. 38, No. 2, pp. 327–334 (Mar. 1988).

Mosimann, S. et al., "X–ray Crystallographic Structure of Recombinant Eosinophil–derived Neurotoxin at 1.83 Å Resolution", *Journal of Molecular Biology*, vol. 260, No. 4, pp. 540–552 (Jul. 26, 1996).

Mouchiroud, D. et al., "Frequencies of Synonymous Substitutions in Mammals are Gene–Specific and Correlated with Frequencies of Nonsynonymous Substitutions", *Journal of Molecular Evolution*, vol. 40, No. 1, pp. 107–113 (Jan. 1995).

Nei, M. et al., "Simple Methods for Estimating the Numbers of Synonymous and Nonsynonymous Nucleotide Substitutions", *Molecular Biology and Evolution*, vol. 3, No. 5, pp. 418–426 (Sep. 1986).

Newton, D. et al., "Toxicity of an Antitumor Ribonuclease to Purkinje Neurons", *The Journal of Neuroscience*, vol. 14, No. 2, pp. 538–544 (Feb. 1994).

Ohta, T., "Further Examples of Evolution by Gene Duplication Revealed Through DNA Sequence Comparisons", *Genetics*, vol. 138, No. 4, pp. 1331–1337 (Dec. 1994).

Openshaw, P., "Immunity and Immunopathology to Respiratory Syncytial Virus", Supplement to: *American Journal of Respiratory and Critical Care Medicine*, vol. 152, No. 4, pp. S59–S62 (Oct. 1995).

Paul, C. et al., "Cytokine induction of granule protein synthesis in an eosinophil–inducible human myeloid cell line, AML14", *Journal of Leukocyte Biology*, vol. 56, No. 1, pp. 74–79 (Jul. 1994).

Prober, C. et al., "Reducing the Morbidity of Lower Respiratory Tract Infections Caused by Respiratory Syncytial Virus: Still No Answer", *Pediatrics*, vol. 99, No. 3, pp. 472–475 (Mar. 1997).

Rosenberg, H. et al., "Human Eosinophil Cationic Protein", *The Journal of Experimental Medicine*, vol. 170, No. 1, pp. 163–176 (Jul. 1, 1989).

Rosenberg, H. et al., "Molecular cloning of the human eosinophil–derived neurotoxin: A member of the ribonuclease gene family", Proceedings of the National Academy of Sciences of the United States of America, vol. 86, No. 12, pp. 4460–4464 (Jun. 1989).

Rosenberg, H. et al., "Characterization of the eosinophil granule proteins recognized by the activation–specific antibody EG2", *Journal of Leukocyte Biology*, vol. 56, No. 4, pp. 502–506 (Oct. 1994).

Rosenberg, H. et al., "Rapid evolution of a unique family of primate ribonuclease genes", *Nature Genetics*, vol. 10, No. 2, pp. 219–223 (Jun. 1995).

Rosenberg, H., "Recombinant Human Eosinophil Cationic Protein", *The Journal of Biological Chemistry*, vol. 270, No. 14, pp. 7876–7881 (Apr. 7, 1995).

Rosenberg, H. et al., "Eosinophil Cationic Protein and Eosinophil–derived Neurotoxin", *The Journal of Biological Chemistry*, vol. 270, No. 37, pp. 21539–21544 (Sep. 15, 1995).

Rosenberg, H. et al., "Molecular cloning and characterization of a novel human ribonuclease (RNase k6): increasing diversity in the enlarging ribonuclease gene family", *Nucleic Acids Research*, vol. 24, No. 18, pp. 3507–3513 (Sep. 15, 1996).

Rosenberg, H. et al., "Diversity among the primate eosinophil–derived neurotoxin genes: a specific C–terminal sequence is necessary for enhanced ribonuclease activity", *Nucleic Acids Research*, vol. 25, No. 17, pp. 3532–3536 (Sep. 1, 1997).

Rosenberg, H., "Isolation of Recombinant Secretory Proteins by Limited Induction and Quantitative Harvest", *Biotechniques*, vol. 24, No. 2, pp. 188, 190 and 192 (Feb. 1998).

Saito, T. et al., "Respiratory Syncytial Virus Induces Selective Production of the Chemokine RANTES by Upper Airway Epithelial Cells", *The Journal of Infectious Diseases*, vol. 175, No. 3, pp. 497–504 (Mar. 1997).

Saxena, S. et al., "Inhibition of HIV–1 Production and Selective Degradation of Viral RNA by an Amphibian Ribonuclease", *The Journal of Biological Chemistry*, vol. 271, No. 34, pp. 20783–20788 (Aug. 23, 1996).

Seminario, M. et al., "The role of eosinophils in the pathogenesis of asthma", *Current Opinion in Immunology*, vol. 6, No. 6, pp. 860–864 (1994).

Shapiro, R. et al., "Characteristic Ribonucleolytic Activity of Human Angiogenin", *Biochemistry*, vol. 25, No. 12, pp. 3527–3532 (Jun. 17, 1986).

Sher, A. et al., "Interleukin 5 is required for the blood and tissue eosinophilia but not granuloma formation induced by infection with *Schistosoma mansoni*", Proceedings of the National Academy of Sciences of the United States of America, vol. 87, No. 1, pp. 61–65 (Jan. 1990).

Sher, A. et al., "Ablation of Eosinophil and IgE Responses with Anti–IL–5 or Anti–IL–4 Antibodies Fails to Affect Immunity Against *Schistosoma mansoni* in the Mouse", *The Journal of Immunology*, vol. 145, No. 11, pp. 3911–3916 (Dec. 1, 1990).

Sibley, C. et al., "The Phylogeny of the Hominoid Primates, as Indicated by DNA–DNA Hybridization", *Journal of Molecular Evolution*, vol. 20, pp. 2–15 (1984).

Sigurs, N. et al., "Eosinophil cationic protein in nasal secretion and in serum and myeloperoxidase in serum in respiratory syncytial virus bronchiolitis: relation to asthma and atopy", *Acta Paediatrica an International Journal of Paediatrics*, vol. 83, No. 11, pp. 1151–1155 (Nov. 1994).

Slifman, N. et al., "Ribonuclease Activity Associated With Human Eosinophil–Derived Neurotoxin and Eosinophil Cationic Protein", *The Journal of Immunology*, vol. 137, No. 9, pp. 2913–2917 (Nov. 1, 1986).

Sorrentino, S. et al., "Eosinophil–derived Neurotoxin and Human Liver Ribonuclease", *The Journal of Biological Chemistry*, vol. 267, No. 21, pp. 14859–14865 (Jul. 25, 1992).

Spry, C., *Eosinophils A Comprehensive Review, and Guide to the Scientific and Medical Literature*, Oxford University Press (1988).

St. Clair, D. et al., "Angiogenin abolishes cell–free protein synthesis by specific ribonucleolytic inactivation of ribosomes", Proceedings of the National Academy of Sciences of the United States of America, vol. 84, No 23, pp. 8330–8334 (Dec. 1987).

Stark J. et al., "Respiratory Syncytial Virus Infection Enhances Neutrophil and Eosinophil Adhesion to Cultured Respiratory Epithelial Cells", *The Journal of Immunology*, vol. 156, No. 12, pp. 4774–4782 (Jun. 15, 1996).

Ticher, A. et al., "Nucleic Acid Composition, Codon Usage, and the Rate of Synonymous Substitution in Protein–Coding Genes", *Journal of Molecular Evolution*, vol. 28, No. 4, pp. 286–298 (Apr. 1989).

Tiffany, H. et al., "Hyperglycosylation of eosinophil ribonucleases in a promyelocytic leukemia cell line and in differentiated peripheral blood progenitor cells", *Journal of Leukocyte Biology*, vol. 58, No. 1, pp. 49–54 (Jul. 1995).

Twiggs, J. et al., "Respiratory Syncytial Virus Infection", *Clinical Pediatrics*, vol. 20, No. 3, pp. 187–190 (Mar. 1981).

Volovitz, B. et al., "Release of leukotriene $C_4$ in respiratory tract during acute viral infection", *The Journal of Pediatrics*, vol. 112, No. 2, pp. 218–222 (Feb. 1988).

Von Lichtenberg, F. et al., "The Fate of Challenge Schistosomula in the Murine Anti–Schistosome Vaccine Model", *The American Journal of Tropical Medicine and Hygiene*, vol. 34, No. 1, pp. 96–106 (Jan.1985).

Wolfe, K. et al., "Mutation rates differ among regions of the mammalian genome",*Nature*, vol. 337, No. 6204, pp. 283–285 (Jan. 19, 1989).

Wolfe, K. et al., "Mammalian Gene Evolution: Nucleotide Sequence Divergence Between Mouse and Rat", *Journal of Molecular Evolution*, vol. 37, No. 4, p. 441–456 (Oct. 1993).

Youle, R. et al., "RNase inhibition of human immunodeficiency virus infection of H9 cells", Proceedings of the National Academy of Sciences of the United States of America, vol. 91, No. 13, pp. 6012–6016 (Jun. 21, 1994).

Young, J. et al., "Mechanism of membrane damage mediated by human eosinophil cationic protein", *Nature*, vol. 321, No. 6070, pp. 613–616 (Jun. 1986).

Zhang, J. et al., "Positive Darwinian selection after gene duplication in primate ribonuclease genes", Proceedings of the National Academy of Sciences of the United States of America, vol. 95, No. 7, pp. 3708–3713 (Mar. 31, 1998).

Zweiman, B. et al., "The relationship between bronchiolitis and allergic asthma",*The Journal of Allergy*, vol. 37, No. 1, pp. 48–53 (Jan. 1966).

Pares, X. et al., "Structure and function of ribonuclease A binding subsites", *Essays in Biochemistry*, vol. 26, pp. 89–103 (1991).

Domachowske, J.B., et al., "Eosinophil cationic protein/ RNase 3 is another RNase A–family ribonuclease with direct antiviral activity", *Nucleic Acids Research*, vol. 26, No. 14, pp. 3358–3363 (Jul. 15, 1998).

* cited by examiner

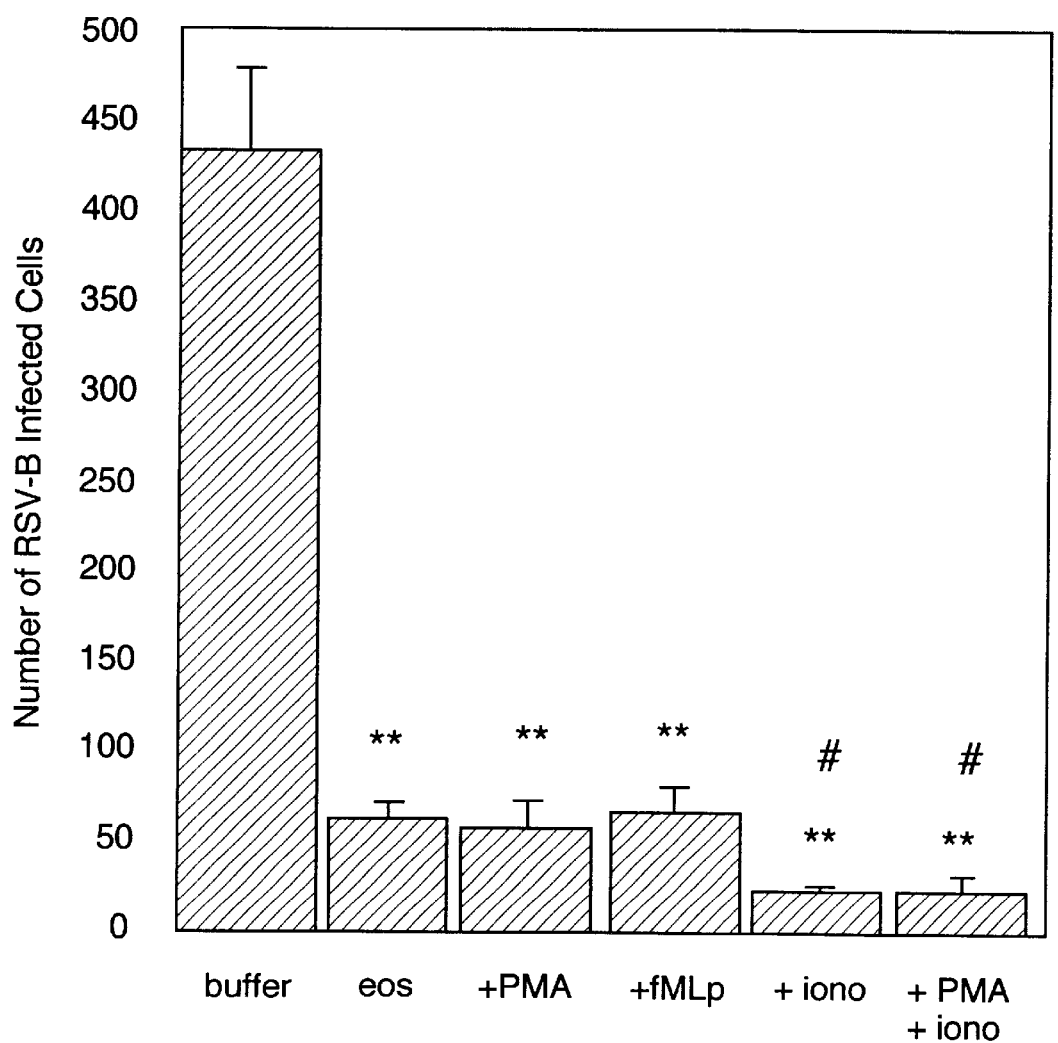

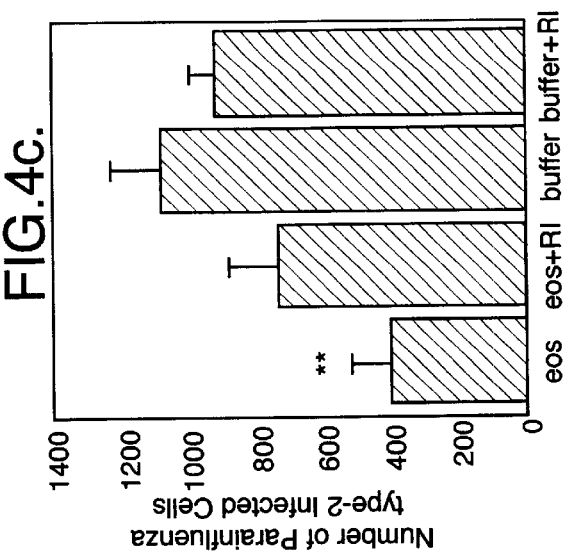
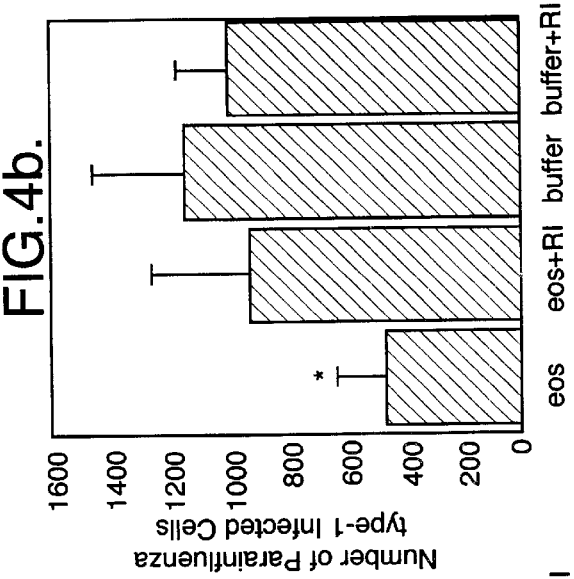
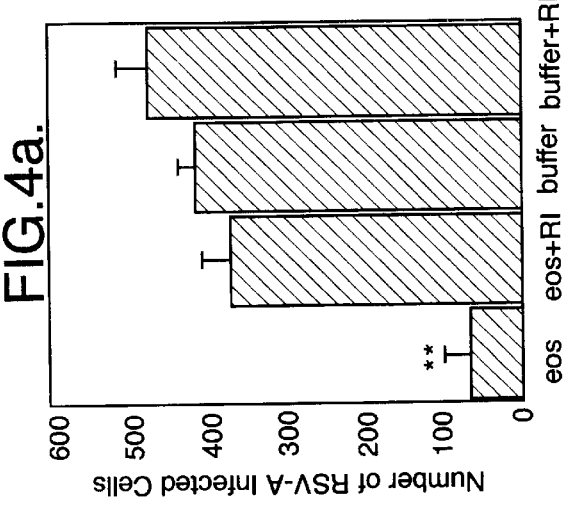
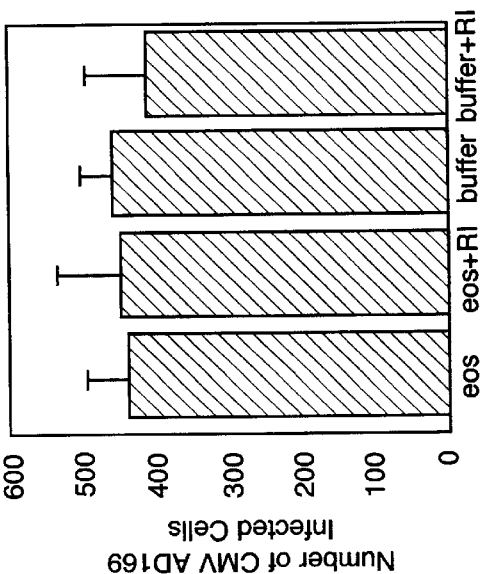
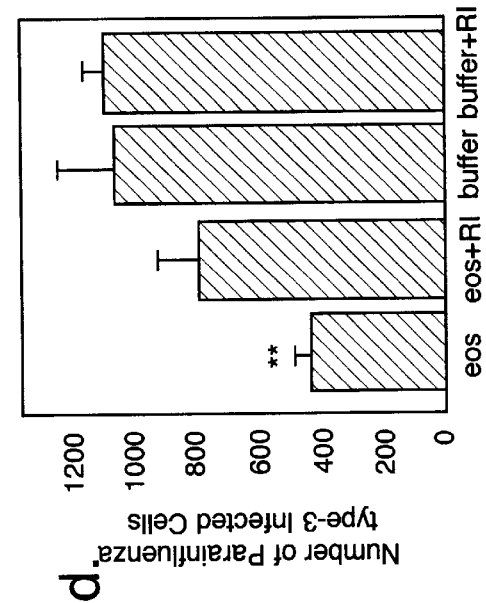

FIG. 12A

```
                        15                                    38
hEDN   KPPQFTWAQWFETQHINMTSQQCTNAMQVINNYQRRCKNQNTFLLTTFAN.
       ...|:||||||||..:|||...:|||||||.|:||||||||||||||||
omEDN  APQKFTRAQWFSIQHIQTTPLRCTNAMRAINKYQHRCKNQNTFLHTTFAA.

⌈VVNVCGNPNMTCPSNKTRKNCHHSGSQVPLIHCNLTTPSPQNISNCRYAQ.
        |||||||:|||||:|:||||||||.:||||||.|||...:.|.||⌉|||
       ⌊VVNVCGNTNITCPRNASLNNCHHSRVQPLTYCNLT..GPPTITNCVYSS.
         ⌊                           ⌉       129
       TPANMFYIVACDNRDQRRDPPQQYPVVPVHLDRII
       :||||||:||||||||..||||||||||||||:|
       TQANMFYVVACDNRDQ.RDPPQYPVVPVHLDTTI
```

FIG. 12b.
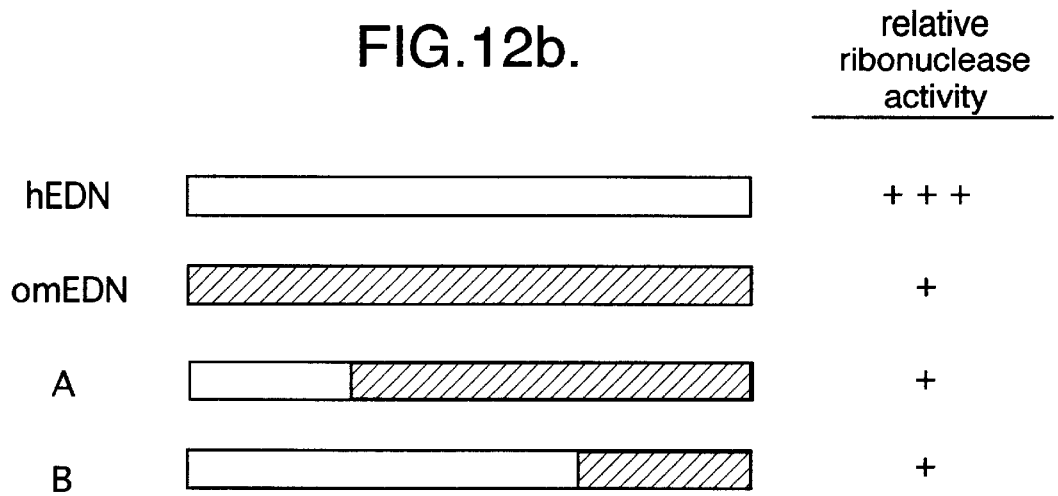
FIG. 13a.
FIG. 13b.
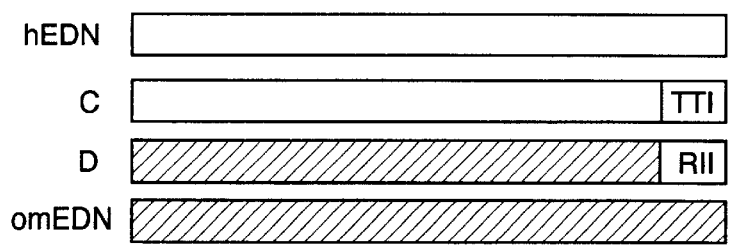
| $K_m$ (uM) | $K_{cat}$ (s$^{-1}$) | $K_{cat}/K_m$ (M$^{-1}$s$^{-1}$) |
|---|---|---|
| 0.70 | 0.91 | $1.3 \times 10^6$ |
| 3.3 | 0.54 | $1.6 \times 10^5$ |
| 5.0 | 0.065 | $1.3 \times 10^4$ |
| 2.0 | 0.023 | $1.2 \times 10^4$ |

FIG. 14

N-terminus

1   [S]KPPQFTWAQW FETQHINMTS QQCTNAMQVI NNYQRRCKNQ NTFLLTTFAN
51  VVNVCGNPNM TCPSNKTRKN CHHSGSQVPL IHCNLTTPSP QNISNCRYAQ
101 TPANMFYIVA CDNRDQRRDP PQYPVVPVHL DRI[EFPGTR SVDDYKDDDDK]
                                           └── FLAG ──┘
                                                    C-terminus

FIG. 15

```
  1 GCTGGATCAG TTCTCACAGG AGCTACAGCG CGGAGACTGG GAAACATGGT
 51 TCCAAAACTG TTCACTTCCC AAATTTGTCT GCTTCTTCTG TTGGGGCTTC
101 TGGCTGTGGA GGGCTCACTC CATGTCAAAC CTCCACAGTT TACCTGGGCT
151 CAATGGTTTG AAACCCAGCA CATCAATATG ACCTCCCAGC AATGCACCAA
201 TGCAATGCAG GTCATTAAACA ATTATCAACG GCGATGCAAA AACCAAAATA
251 CTTTCCTTCT TACAACTTTT GCTAACGTAG TTAATGTTTG TGGTAACCCA
301 AATATGACCT GTCCTAGTAA CAAAACTCGC AAAAATTGTC ACCACAGTGG
351 AAGCCAGGTG CCTTTAATCC ACTGTAACCT CACAACTCCA AGTCCACAGA
401 ATATTTCAAA CTGCAGGTAT GCGCAGACAC CAGCAAAACAT GTTCTATATA
451 GTTGCATGTG ACAACAGAGA TCAACGACGA GACCCTCCAC AGTATCCGGT
501 GGTTCCAGTT CACCTGGATA GAATCATCTA AGCTCCTGTA TCAGCACTCC
551 TCATCATCAC TCATCTGCCA AGCTCCTCAA TCATAGCCAA GATCCCATCT
601 CTCCATATAC TTTGGGTATC AGCATCTGTC CTCATCAGTC TCCATACCCC
651 TTCAGCTTTC CTGAGCTGAA GTGCCTTGTG AACCCTGCAA TAAACTGCTT
701 TGCAAATTC
```

FIG. 16A
FIG. 16B
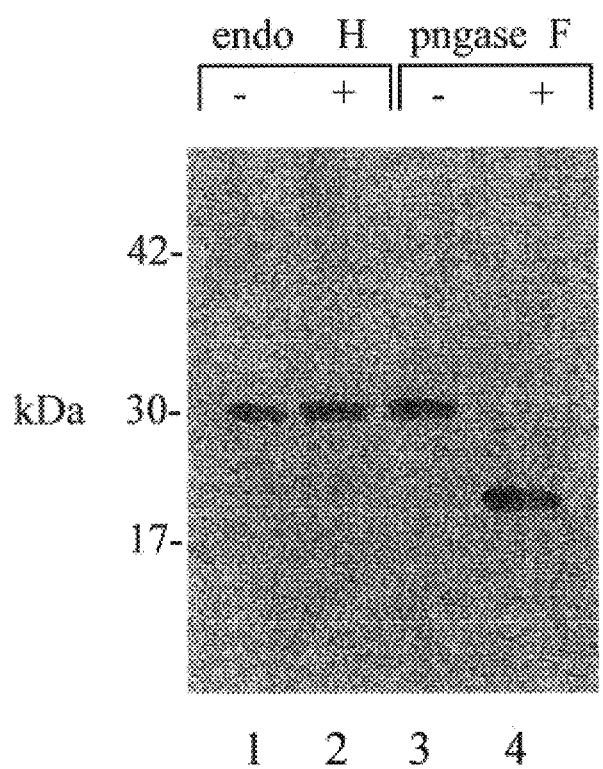
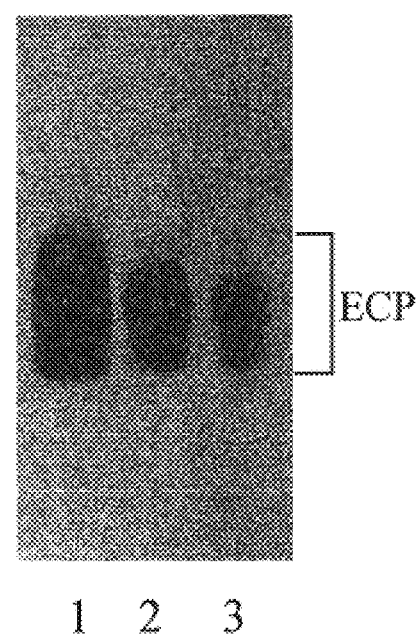

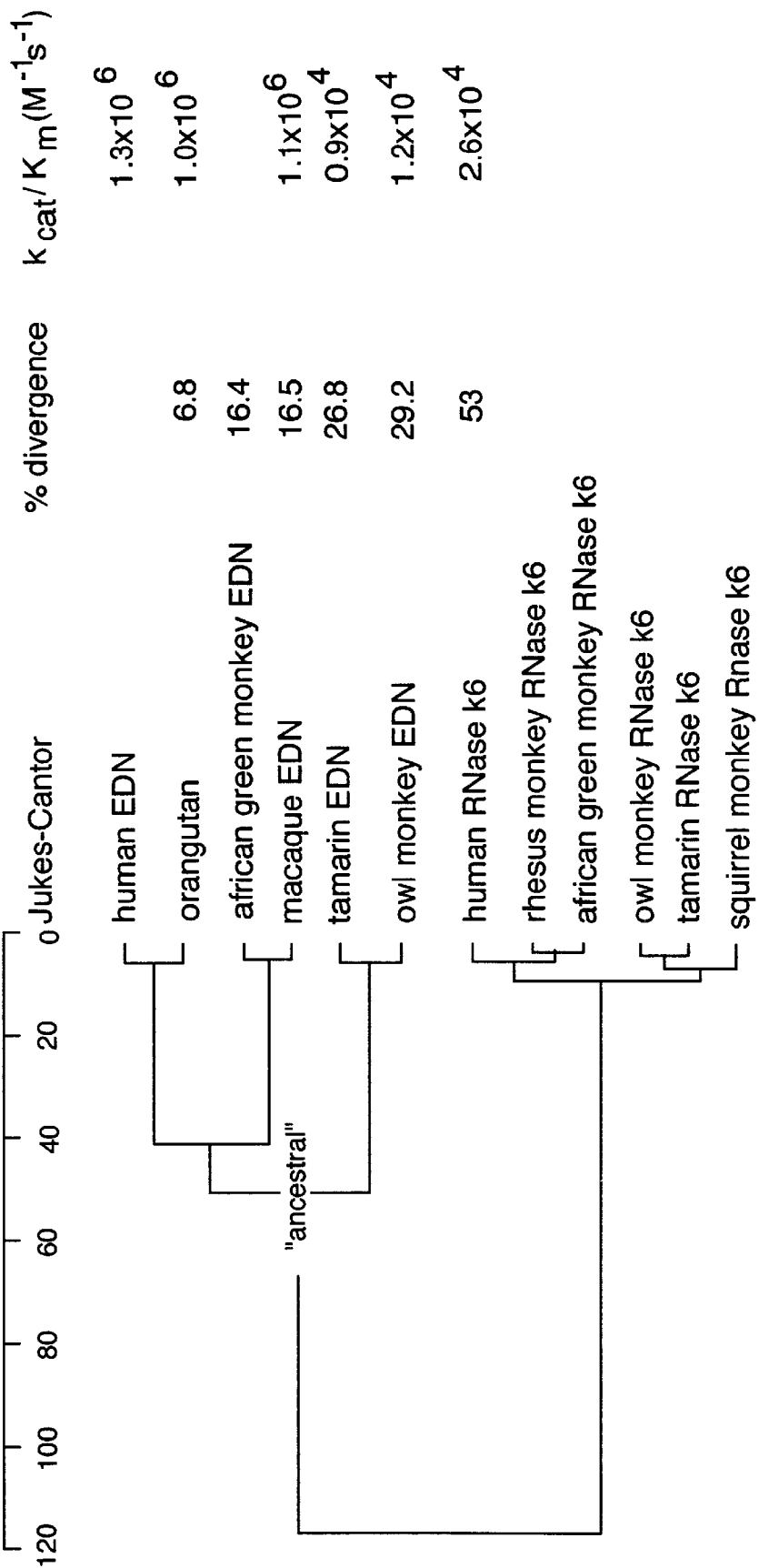

FIG. 19A

```
hEDN    KPPQFTWAQWFETQHINMTSQQCTNAMQVINNYQRRCKNQNTFLLTTFAN
        ..|.|:|||||||..||.|.:|||||||||.|.|:||.|||||||||||.
omEDN   APQKFTRAQWFSIQHIQTTPLRCTNAMRAINKYQHRCKNQNTFLHTTFAA

[VVNVCGNPNMTCPSNKTRKNCHHSGSQVPLIHCNLTTPSPQNISNCRYAQ
         ||||||:|.:|||.|.|..:|||||.:|||..|||||.||.:|..||.|
         VVNVCGNTNITCPRNASLNNCHHSRVQVPLTYCNLT..GPPTITNCVYSS]

TPANMFYIVACDNRDQRRDPPQYPVVPVHLDRII
        :.|.||||:||||||||.||||||||||||||.|
        TQANMFYVVACDNRDQ.RDPPQYPVVPVHLDTTI
```

METHODS FOR INACTIVATING ENVELOPED RNA VIRUS PARTICLES AND COMPOSITIONS FOR USE THEREWITH

This application is based on International Patent Application PCT/US98/13852 filed Jul. 2, 1998, which is based on U.S. Provisional Application No. 60/052,986 filed on Jul. 2, 1997, the entire contents of which are incorporated by reference herein. Throughout this application various publications are referenced. The disclosures of these publications in their entireties are hereby incorporated by reference into this application in order to more fully describe the state of the art to which this invention pertains.

BACKGROUND OF THE INVENTION

The eosinophil-derived neurotoxin (EDN) is a small, glycosylated protein found in the large specific granules of eosinophilic leukocytes. Durack and colleagues (D. T. Durack et at., 1981, Proc. Natl. Acad. Sci., USA 78:5165–5169) reported the isolation of EDN, and determined that eosinophil—related neurotoxicity—a syndrome of ataxia and paralysis associated with Purkinje cell degeneration (the Gordon phenomenon (M. H. Gordon, 1933, Br. Med. J. 1:643)—is mediated in part by the activity of this secretory protein (D. T. Durack et al., 1981, Proc. Natl. Acad. Sci., USA 78:5165–5169; D. T. Durack et al., 1979, Proc. Natl. Acad. Sci., USA 76:1443–1447).

Gleich and colleagues (G. J. Gleich et at., Proc. Natl. Acad. Sci., USA 83:3146–3150) later reported the amino terminal sequence of purified EDN, and noted the similarity between this peptide and the amino-terminal sequence of bovine ribonuclease A (RNase A). EDN's membership in the RNase A family of ribonuclease genes was later confirmed by molecular cloning (H. F. Rosenberg et al., 1989, Proc. Natl. Acad. Sci., USA 86:4460–4464; R. L. Barker et al., 1989, J. Immunol., 143:952–955). In terms of enzymatic activity, EDN is a catalytically efficient ribonuclease (N. R. Slifman et al., 1986, J. Immunol., 137:2913–2917; U. Gullberg et at, 1986, Biochem. Biophys. Res. Commun., 139:1239–1242; M. Iwami et al., 1981, J. Biochem., 89:1005–1016) and exhibits some degree of preference among experimental substrates (S. Sorrentino et al., 1992, J. Biol. Chem., 267:14859–14865). Both Sorrentino and colleagues (S. Sorrentino et al., 1992, J. Biol. Chem., 267:14859–14865) and Newton and colleagues (D. L. Newton et al., 1994, J. Neurosci., 14:538–544) have shown that EDN's neurotoxic effects are directly dependent on ribonuclease activity.

While the involvement of eosinophils in the pathophysiology of allergic diseases and asthma has been studied extensively, the potential beneficial roles played by these cells remain poorly understood (A. Sher et al., 1990, Proc. Natl. Acad. Sci. USA, 87:61–65; A. Sher et al., 1990. J. Immunol., 145:3911–3916; F. von Lichtenberg et al., 1985; Am. J. Trop. Med. Hyg., 34:96–106; F. J. Herndon et al., 1992, J. Immunol., 149:3642–3647; C. J. F. Spry 1988. Eosinophils. A comprehensive review and guide to the scientific and medical literature, Oxford University Press, Oxford, UK; G. J. Gleich, 1992, in Inflammation: basic principles and clinical correlates (J. I. Gallin et al., eds.) Raven Press Ltd, New York pp. 663–680). Under physiologic conditions, eosinophils represent only a small fraction of the total leukocytes present in peripheral blood, with the vast majority residing in the perivascular areas of the respiratory and gastrointestinal tracts (C. J. F. Spry, 1988, Oxford University Press, Oxford. UK).

Human eosinophils contain a number of distinct secretory effectors, including eosinophil peroxidase (EPO), major basic protein (MBP), eosinophil-derived neurotoxin (EDN), and eosinophil cationic protein (ECP) (G. J. Gleich 1992, Raven Press Ltd, New York. pp. 663–680; S. J. Ackerman, 1993 CRC Press, Boca Raton, Fla. pp. 33–70). EDN and ECP are closely-related proteins that have ribonuclease activity (N. R. Slifman et al., 1986, J. Immunol., 137:2913–2917; U. Gullberg et al., 1986, Biophys. Bioch. Res. Commun., 139:1239–1242) and that are members of the ribonuclease A (RNase A) superfamily (G. J. Gleich et al., 1986, Proc. Natl. Acad. Sci. USA. 83:3146–3150; H. F. Rosenberg et al., 1989, J. Exp. Med., 170:163–76; H. F. Rosenberg et al., 1989, Proc. Natl. Acad. Sci., USA 86:4460–4464; H. F. Rosenberg et al., 1995, Nature Genetics 10:219–223).

Although ECP has both anti-parasitic and antibacterial activity in vitro (S. J. Ackerman et al., 1985, Am. J. Trop. Med. Hyg., 34:735–745; R. I. Lehrer et al., 1986, J. Immunol., 142:4428–4434), neither of these functions depends on ribonuclease activity (H. A. Molina et al., 1988, Am. J. Trop. Med. Hyg., 38:327–334; H. F. Rosenberg, 1995, J. Biol. Chem., 270:7876–7881). There is evidence to suggest that ECP destabilizes the lipid membranes of target pathogens (J. D. E. Young et al., 1986, Nature, 321:613–616).

EDN, the major eosinophil ribonuclease, is 100-fold more ribonucleolytically active than ECP (N. R. Slifman et al., 1986, J. Immunol., 137:2913–2917) and although EDN displays specific neurotoxic activity when injected directly into the central nervous systems of experimental animals (D. T. Durack et al., 1979, Proc. Natl. Acad. Sci. USA, 76:1443–1447; D. T. Durack et al., 1981, Proc. Natl. Acad. Sci. USA, 78:5165–5169; D. L. Newton et al., 1994, J. Neurosci., 14:538–544; S. Sorrentino et al., 1992, J. Biol. Chem., 267:14859–14865), it has no defined physiologic function. The ribonucleolytic activities of EDN and ECP, the known membrane-disruptive potential of ECP, and findings relating other ribonucleases to the pathogenesis of viral disease (R. J. Youle et al., 1994, Proc. Natl. Acad. Sci. USA, 91:6012–6016; S. K. Saxena et al., 1996, J. Biol. Chem., 271:20783–20788; A. Mitra et al., 1996, Proc. Natl. Acad. Sci., USA 93:6780–6785; N. M. Cirino et al., 1997, Proc. Natl. Acad. Sci. USA, 94:1937–1942) raise questions about the role of ECP and EDN in the response to infection by enveloped RNA viruses.

Potential target pathogens of EDN and ECP are viruses of the family Paramyxoviridae, including respiratory syncytial virus (RSV) and parainfluenza virus. Although eosinophils are not generally perceived as agents of host defense against viral disease, there are a number of intriguing associations linking eosinophils, eosinophil granule proteins, asthma and allergic bronchospasm, and the pathogenesis of RSV disease (M. C. Seminario and G. J. Gleich, 1994, Curr. Opin. Immunol., 6:860–864; B. Burrows et al., 1977, Am. Rev. Respir. Dis., 115:751–760; B. Zweiman et al., 1996, J. Allerg., 37:48–53; J. T. Twiggs et al., 1981, Clin. Pediatr., 20:187. 190).

RSV has been recognized as the single most important respiratory pathogen in the newborn to two year old age group (C. B. Hall, 1993, Contemporary Pediatrics pp. 92–110). In the United States alone, approximately 67% of all children are infected with RSV within the first year of life, and 50% of those infected develop lower respiratory tract disease. Of this group, 2.5% require hospitalization (approximately 90,000 hospital admissions per year) leading to 4,000 deaths. RSV bronchiolitis in childhood has also been associated with the development of future respiratory disorders, most prominently, Reactive Airways Disease (asthma), a condition currently on the rise in the United States. Recent work has also established the importance of RSV in respiratory compromise in the elderly population (A. R. Falsey et al., 1995, J. Infect. Dis., 172:389–394). Controversy surrounds the use of currently available therapies (Ribavarin, RSV-immune globulin) (C. G. Prober and E. E. L. Wang, 1997, Pediatrics, 99:472–475). There is no vaccine readily available to combat this highly contagious disease.

Several groups have shown that, during RSV infection, eosinophils are recruited to and degranulate into the lung parenchyma (R. Garofalo et al., 1992, J. Pediatr., 120:28–32; E. A. Colocho Zelaya et al., 1994, Ped. All. Immunol., 5:100–106; P. J. Openshaw, 1995, Am. J. Respi. Crit. Care Med., 152.S59–S62; N. Sigurs et al., 1994, Acta Paediatr., 83:1151–1155) and wheezing during RSV infection is associated with increased concentrations of leukotriene C4 (B. Volovitz et al., 1992, J. Pediatr., 112:218–222) and ECP (R. Garofalo et al., 1992, J. Pediatr., 120:28–32) in respiratory secretions. Stark and colleagues (J. M. Stark et al., 1996, J. Immunol., 156:4774–4782) have shown that cultured respiratory epithelial cells infected with RSV support increased adherence of activated eosinophils. Kimpen and colleagues (J. L. L. Kimpen et al., 1995, Pediatric Res. 32:160–164) present evidence suggesting direct activation of eosinophils exposed to RSV in vitro. Saito and colleagues (T. Saito et al., 1997, 175:497–504) have demonstrated that human epithelial cells up-regulate the expression of the eosinophil chemoattractant, RANTES, in response to infection with RSV.

Most dramatically, children previously vaccinated with a formalin-inactivated RSV vaccine who subsequently developed natural RSV infection had increased blood eosinophil counts (J. Chin et al., 1969, Am. J. Epidemiol., 89:449–463) and massive eosinophil infiltrates were observed in post-mortem specimens of vaccinated children who died of RSV pneumonia (H. W. Kim et al., 1969, Am. J. Epidemiol., 89:422–433). These studies demonstrate that recruitment of eosinophils to the respiratory tract can and does occur in response to RSV infection, and, when exaggerated. may lead to a more severe form of RSV disease.

There is a need for agents useful to prevent and treat infection by enveloped RNA viruses, particularly single-stranded RNA viruses such as RSV. The methods and compositions of the present invention address this need.

SUMMARY OF THE INVENTION

The present invention provides a method for inactivating a virion of an enveloped RNA virus. The method comprises contacting the virion with an eosinophil-derived ribonuclease. Examples of eosinophil-derived ribonucleases include, but are not limited to, eosinophil-derived neurotoxin (EDN), eosinophil cationic protein (ECP), and congeners thereof. The invention additionally provides a method for treating a subject infected by an enveloped RNA virus. The method comprises administering to the subject an effective amount of an eosinophil-derived ribonuclease, such as EDN or ECP, a congener thereof or a pharmaceutically acceptable salt thereof. The invention additionally provides a method for preventing infection by an enveloped RNA virus in a subject. The method comprises administering to the subject an effective amount of an eosinophil-derived ribonuclease, such as EDN or ECP, a congener thereof or a pharmaceutically acceptable salt thereof.

In one embodiment, the eosinophil-derived ribonuclease is a recombinant protein. In one embodiment, the eosinophil-derived ribonuclease is a human protein. EDN includes proteins comprising the amino acid sequence shown in FIG. 14, SEQ ID NO:7 or 10, or encoded by the nucleotide sequence shown in FIG. 15 (SEQ ID NO:8) or SEQ ID NO:9. ECP includes proteins comprising the coding sequence of human ECP, encoded by nucleotides 55–537 of GenBank Accession No. X15161.

In one embodiment, the enveloped RNA virus is a single-stranded RNA virus, such as a member of the Paramyxoviridae, Orthomyxoviridae, Retroviridae, Togaviridae, Rhabdoviridae, Flaviviridae, Coronaviridae, or Filoviridae families. Members of the Paramyxoviridae family include, but are not limited to, parainfluenza virus (PIV) types 1, 2, 3 and 4, and respiratory syncytical virus (RSV) groups A and B. In another embodiment, the enveloped RNA virus is a double-stranded RNA virus.

The invention further provides a composition comprising an eosinophil-derived ribonuclease, such as eosinophil-derived neurotoxin (EDN), eosinophil cationic protein (ECP), a congener thereof, or a pharmaceutically acceptable salt thereof and, optionally, an acceptable carrier. In one embodiment, the composition is a pharmaceutical composition. In one embodiment, the composition is for aerosol administration. In another embodiment, the composition is for parenteral administration.

BRIEF DESCRIPTION OF THE FIGURES

FIG. 3A shows the number of RSV-B infected HEp-2 target cells per confluent monolayer after pre-treatment of RSV-B viral stocks with buffer, eosinophils (0.4×10⁶/ml), eosinophils+PMA (100 ng/ml), eosinophils+fMLP (100 μM), eosinophils +ionomycin (2 μM), or eosinophils+PMA+ionomycin. Error bars show the standard deviation for triplicate values under each condition. Two way analysis of variance was applied (ANOVA), asterisks show significance when compared to buffer control (**p<0.01) # shows significance when compared to eosinophils alone (#p<0.05).

FIG. 4A shows the results of independent trials demonstrating the effect of pre-treatment of RSV-A with isolated human eosinophils (0.4×10⁶/ml viral stock)+/−RI. Two way analysis of variance (ANOVA) was applied comparing each condition to the appropriate buffer control, asterisks show significance (*p<0.05; **p<0.01).

FIG. 4B shows the results of independent trials demonstrating the effect of pre-treatment of parainfluenza type 1 with isolated human eosinophils (0.4×10⁶/ml viral stock)+/−RI. Two way analysis of variance (ANOVA) was applied comparing each condition to the appropriate buffer control, asterisks show significance (*p<0.05; **p<0.01).

FIG. 4C shows the results of independent trials demonstrating the effect of pre-treatment of parainfluenza type 2 with isolated human eosinophils (0.4×10⁶/ml viral stock)+/−RI. Two way analysis of variance (ANOVA) was applied comparing each condition to the appropriate buffer control. asterisks show significance (*p<0.05; **p<0.01).

FIG. 4D shows the results of independent trials demonstrating the effect of pre-treatment of parainfluenza type 3 with isolated human eosinophils (0.4×10⁶/ml viral stock)+/−RI. Two way analysis of variance (ANOVA) was applied comparing each condition to the appropriate buffer control, asterisks show significance (*p<0.05; **p<0.01).

FIG. 4E shows the results of independent trials demonstrating the effect of pre-treatment of cytomegalovirus strain AD 169 with isolated human eosinophils (0.4×10⁶/ml viral stock)+/−RI. Two way analysis of variance (ANOVA) was applied comparing each condition to the appropriate buffer control, asterisks show significance (*p<0.05; **p<0.01).

FIG. 8B)

FIG. 12A shows amino acid sequence comparison between human EDN (SEQ ID NO:5) and owl monkey (SEQ ID NO:6) EDN as predicted from their respective cDNA sequences. Boxes enclose each of the eight cysteines conserved in this gene family; numbering above the sequence denotes the position of the conserved catalytic residues His 15, Lys 38 and His 129, numbered as per hEDN sequence. The brackets indicate the division points within chimeras A and B, as shown in FIG. 12B.

FIG. 12B is a diagram of hEDN (open rectangle), omEDN (shaded rectangle) and chimeras A and B with portions of both sequences. The relative ribonuclease activities of the recombinant EDNs and chimeras are shown at the right.

FIG. 13A is a diagram of chimeras. The three carboxy-terminal amino acids of omEDN (Thr-Thr-Ile) replace those of hEDN (Arg-Ile-Ile) in chimera C, and the reverse in chimera D.

FIG. 13B shows values for $K_m$ and $k_{cat}$ as calculated from the intercepts of double reciprocal plots of substrate concentration versus initial rates for chimeras C and D; values for hEDN from Rosenberg and Dyer, supra and omEDN, from FIG. 11 were included for comparison.

FIG. 14 is the amino acid sequence of recombinant human EDN (SEQ ID NO:7) prepared from the pFLAG-CTS bacterial expression system. Regions in boxes denote sequences not encoded by the cDNA.

FIG. 15 is a nucleic acid sequence encoding human EDN (SEQ ID NO:8).

FIG. 16A shows a western blot probed with M2 mAb demonstrating electrophoretic mobility and glycosylation of recombinant human ECP (rhECP) isolated from supernatants from baculovirus-infected Sf9 cells. Purified protein in lanes 2 and 4 were subjected to deglycosylation with endoglycosidase H (endo H) and endoglycosidase F (pngase F), respectively.

FIG. 16B shows a western blot probed with polyclonal anti-ECP antiserum demonstrating electrophoretic mobility of native ECP detected in an extract from human peripheral blood eosinophils.

FIG. 18A is a dendrogram depicting the relationships among human and non-human primate EDNs and human RNase k6. Distances were calculated by a version of the Jukes-Cantor method as per the DISTANCES algorithm of the Wisconsin Genetics Computer Group (WGCG) program on-line at the National Institutes of Health. Signal sequences were not included in the calculations. The ancestral sequence noted at the node demarcating the divergence of the Old World from the New World monkeys was inferred by maximum parsimony over informative sites.

FIG. 18B shows amino acid sequence divergences (1-%identity) as per the GAP algorithm of WGCG; signal sequences not included.

FIG. 18C shows catalytic constants determined via double-reciprocal plots of ribonuclease activities of each cDNA-encoded protein expressed in recombinant form.

FIG. 19A shows alignment of coding sequences of human (SEQ ID NO:5) and owl monkey (SEQ ID NO:6) EDN genes, with brackets indicating divisions between segments used to generate individual chimeras.

DETAILED DESCRIPTION OF THE INVENTION

Figure 1A:
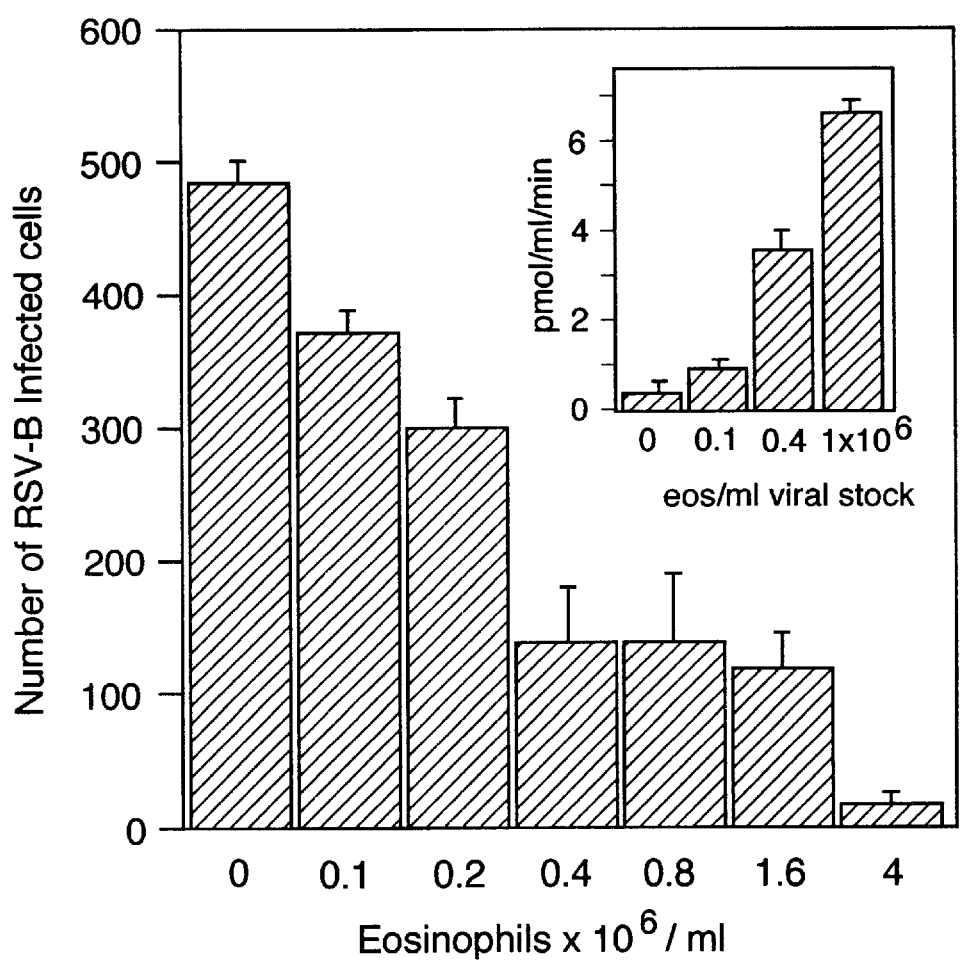
FIG. 1A shows the results of independent trials demonstrating the dose-dependent reduction in number of infected target HEp-2 cells per confluent monolayer resulting from pre-treatment of RSV-B viral stocks with isolated human eosinophils (0 to $4 \times 10^6$/ml viral stock). The inset shows activity of ribonucleases released from human eosinophils under these experimental conditions.

The invention provides methods and compositions for prevention and treatment of infection by enveloped RNA viruses, such as single-stranded RNA viruses, including paramyxoviruses such as RSV and PIV, and retroviruses. EDN and ECP are relatively soluble and thermostable proteins, quite active at low concentrations, with no direct toxicity to bronchial epithelial cells. Thus, recombinant EDN or ECP would be suitable for inhalation therapy. EDN and ECP can be used separately or in combination.

EDN or ECP, particularly recombinant EDN or ECP, may be used as an agent for direct inhalation therapy in children with established RSV bronchiolitis, in children for which there is a high index of suspicion, and as prophylactic therapy in children with predisposing conditions such as prematurity, bronchiole pulmonary displasia, congenital heart disease and immunodeficiency. Similar criteria may be applied to the susceptible elderly population.

Definitions

All scientific and technical terms used in this application have meanings commonly used in the art unless otherwise specified. As used in this application, the following words or phrases have the meanings specified.

As used herein "enveloped RNA virus" includes, but is not limited to single-stranded RNA viruses such as, members of the families: Paramyxoviridae, Orthomyxoviridae, Retroviridae, Togaviridae, Rhabdoviridae, Filoviridae, Flaviviridae, and Coronaviridae. Also included are double-stranded RNA viruses.

As used herein "Paramyxoviridae family" includes, but is not limited to, parainfluenza virus (PIV) types 1, 2, 3 and 4, respiratory syncytical virus (RSV) groups A and B, and measles virus.

As used herein "Orthomyxoviridae family" includes, but is not limited to, influenza virus A and B.

As used herein "Retroviridae family" includes, but is not limited to, human immunodeficiency virus (HIV) and human T-lymphotropic virus (HTLV) 1 and 2.

As used herein "Togaviridae family" includes, but is not limited to, rubella.

As used herein "Rhabdoviridae family" includes. but is not limited to, rabies virus.

As used herein "Filoviridae family" includes, but is not limited to, ebola virus.

As used herein "Flaviviridae family" includes, but is not limited to, yellow fever virus.

As used herein "Coronaviridae family" includes, but is not limited to, corona virus.

As used herein "eosinophil-derived neurotoxin" (EDN) means EDN purified from eosinophils or recombinant EDN. Examples of sources from which EDN may be purified or derived include, but are not limited to, primate eosinophils, including human eosinophils. Examples of recombinant EDN (rEDN) include. but are not limited to, polypeptides comprising the amino acid sequence shown in FIG. 14 (SEQ ID NO:7) or shown in SEQ ID NO: 10, polypeptides encoded by the nucleotide sequence shown in SEQ ID NO:8 or 9, polypeptides encoded by the nucleotide sequence having GenBank Accession No. M24157, congeners thereof or pharmaceutically acceptable salts thereof.

As used herein "eosinophil cationic protein" (ECP) means ECP purified from eosinophils or recombinant ECP. Examples of sources from which ECP may be purified or derived include, but are not limited to, primate eosinophils, including human eosinophils. Examples of recombinant ECP (rECP) include, but are not limited to, polypeptides encoded by nucleotides 55–537 of GenBank Accession No. X15161, congeners thereof or pharmaceutically acceptable salts thereof.

As used herein, "congener" of EDN or ECP means an EDN or ECP molecule having one or more amino acid substitutions or deletions in the amino acid sequence indicated, yet retaining the ability to inactivate virions of enveloped RNA viruses.

As used herein, "to inactivate a virion" means to render the virion incapable of reproducing. One skilled in the art can determine the ability of an EDN or ECP molecule or congener thereof to inactivate virions by using the shell vial assay described in Example 1, infra.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with the active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Col. Easton Pa. 18042, USA).

Methods of the Invention

The present invention provides a method for inactivating a virion of an enveloped RNA virus. The method comprises contacting the virion with an eosinophil-derived ribonuclease. Examples of eosinophil-derived ribonucleases include, but are not limited to, eosinophil-derived neurotoxin (EDN), eosinophil cationic protein (ECP), and congeners thereof. The method can be performed in vivo or ex vivo.

The invention additionally provides a method for treating a subject infected by an enveloped RNA virus. The method comprises administering to the subject an effective amount of an eosinophil-derived ribonuclease, such as EDN or ECP, a congener thereof or a pharmaceutically acceptable salt thereof.

The invention additionally provides a method for preventing infection by an enveloped RNA virus in a subject. The method comprises administering to the subject an effective amount of an eosinophil-derived ribonuclease, such as EDN or ECP, a congener thereof or a pharmaceutically acceptable salt thereof.

In one embodiment, the enveloped RNA virus is a member of the Paramyxoviridae, Orthomyxoviridae, Retroviridae, Togaviridae, Rhabdoviridae, Filoviridae, Flaviviridae or Coronaviridae families.

Examples of members of the Paramyxoviridae family include, but are not limited to, parainfluenza virus (PIV) types 1, 2, 3 and 4, respiratory syncytical virus (RSV) groups A and B, and measles virus.

Examples of members of the Orthomyxoviridae family include, but are not limited to, influenza virus A and B. Examples of members of the Retroviridae family include, but are not limited to, human immunodeficiency virus (HIV) and human T-lymphotropic virus (HTLV) 1 and 2. Examples of members of the Togaviridae family include, but are not limited to, rubella. Examples of members of the Rhabdoviridae family include, but are not limited to, rabies virus. Examples of members of the Filoviridae family include, but are not limited to, ebola virus. Examples of members of the Flaviviridae family include, but are not limited to, yellow fever virus. Examples of members of the Coronaviridae family include, but are not limited to. corona virus.

In one embodiment, the eosinophil-derived ribonuclease is a recombinant protein. In one embodiment, the eosinophil-derived ribonuclease is a human protein. EDN includes proteins comprising the amino acid sequence shown in FIG. 14 (SEQ ID NO:7), or SEQ ID NO:10, or encoded by the nucleotide sequence shown in FIG. 15 (SEQ ID NO:9) or SEQ ID NO:9. ECP includes proteins comprising the coding sequence of human ECP, encoded by nucleotides 55–537 of GenBank Accession No. X15161.

Further, congeners of EDN or ECP for use in accordance with the invention can have amino acid substitutions or deletions in the amino acid sequence shown in FIG. 14 (SEQ ID NO:7) or shown in SEQ ID NO:10. The only requirement being that substitutions or deletions result in EDN or ECP that retains the ability to inactivate virions of enveloped RNA viruses. These amino acid substitutions include, but are not necessarily limited to, amino acid substitutions known in the art as conservative.

For example, it is a well-established principle of protein chemistry that certain amino acid substitutions, referred to as conservative amino acid substitutions, can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine. and sometimes with valine. Lysine (K) and arginine (R) are frequently interchangeable in locations in which the significant feature of the amino acid residue is its charge and the differing pK's of these two amino acid residues are not significant. Still other changes can be considered conservative in particular environments.

In the amino acid sequence of EDN shown in FIG. 14, all or nearly all of the 8 cysteines are likely to be important to the three dimensional structure of the molecule (H. F. Rosenberg et al, 1989, Proc. Natl. Acad. Sci., USA 86:4460–4464). The histidines at positions 15 and 129, the lysine at position 38, the arginine at position 132, and the isoleucine at position 133 are important to the enhanced ribonuclease activity of EDN (See Example 4, infra, and Rosenberg and Dyer, 1995, J. Biol. Chem., 270:21539–21544). The residues indicated in boxes in FIG. 14 are not essential to EDN activity.

Efficacy of an EDN molecule of the invention for treating or preventing infection by an enveloped RNA virus can be determined in an animal model. Animal models for RSV infection are reviewed in P. J. M. Openshaw, 1995, *Am. J. Respir. Crit. Care Med.*, 152:S59–S62.

Administration of the Compositions

In accordance with the methods of the invention, the eosinophil-derived ribonuclease can be administered in a pharmaceutical composition in unit dosage form, preferably parenterally or via aerosol. The most effective mode of administration and dosage regimen for the molecules of the present invention depend upon the location of the tissue or disease being treated, the severity and course of the medical disorder, the subject's health and response to treatment and the judgment of the treating physician. Accordingly, the dosages of the molecules should be titrated to the individual subject.

By way of example, the interrelationship of dosages for animals of various sizes and species and for humans based on mg/m² of surface area is described by E. J. Freireich et al., 1966, *Cancer Chemother. Rep.*, 50(4):219–244. It would be clear that the dose of the composition of the invention required to achieve an appropriate clinical outcome may be further reduced with schedule optimization.

By way of example, for treating a subject infected by a member of the Paramyxoviridae family, such as RSV, recombinant EDN or ECP can be administered at a dose of about 1 to about 20 mg/kg body weight, once per day to every 4 hours, or with aerosol administration, as needed.

For direct inhalation therapy, there are a number of nebulizers currently in use in pediatric hospital settings (Salter 8900, B+F 61399, Marquist Acorn II) that could readily administer this type of therapeutic agent. Recombinant EDN or ECP may also be useful as adjunctive therapy when administered via an intramuscular or intravenous route.

For inhalation therapy, the EDN or ECP molecules of the invention will be formulated as an aerosol. The term "aerosol" includes any gas-borne suspended phase of the EDN or ECP molecules of the invention which is capable of being inhaled into the bronchioles or nasal passages. Specifically, aerosol includes a gas-borne suspension of droplets of the EDN or ECP molecules of the invention, as may be produced in a metered dose inhaler or nebulizer, or in a mist sprayer. Aerosol also includes a dry powder composition of an EDN or ECP molecule of the invention suspended in air or other carrier gas, which may be delivered by insufflation from an inhaler device, for example.

For solutions used in making aerosols of the present invention, the preferred range of concentration of the EDN or ECP molecules of the invention is 10 ng/ml to 1 mg/ml, more preferably 1 $\mu$g/ml to 100 $\mu$g/ml. Usually the solutions are buffered with a physiologically compatible buffer such as phosphate or bicarbonate. A typical pH range is 5–9, preferably 6.5–7.8, and more preferably 7.0–7.6. Typically, sodium chloride is added to adjust the osmolarity to the physiological range, preferably within 10% of isotonic. Formulation of such solutions for creating aerosol inhalants is discussed in Remington's Pharmaceutical Sciences, supra; see also, Ganderton & Jones, 1987, Drug Delivery to the Respiratory Tract, Ellis Horwood; Gonda, 1990, Critical Reviews in Therapeutic Drug Carrier Systems, 6:273–313; and Raeburn et al., 1992, J. Pharmocol. Toxicol. Methods, 27:143–159.

Solutions of the EDN or ECP molecules of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice. thereby putting droplets of the solution into the mouth and trachea of the subject to which the drug is to be administered. Typically, a mouth piece is fitted to the outlet of the orifice to facilitate delivery into the mouth and trachea.

When a congener of EDN or ECP is administered, it may be useful to additionally suppress the subject's immune responses to any foreign antigens introduced by the altered EDN or ECP molecule. Methods to suppress immune responses are well-known in the art (see R. S. Handschumacher, 1993, Drugs used for immunosuppression, in Goodman and Gilman's The Pharmacological Basis of Therapeutics, 8th ed., Gilman et al., eds., McGraw-Hill, New York, 1264–1276).

Compositions of the Invention

The invention further provides a pharmaceutical composition comprising an eosinophil-derived ribonuclease, congener thereof or a pharmaceutically acceptable salt thereof and a pharmaceutically acceptable carrier. The compositions can be used in the form of pharmaceutical preparations comprising the eosinophil-derived ribonuclease in a pharmacologically effective amount in admixture with a pharmaceutically acceptable carrier which may be conventional per se. These preparations may be formulated by well known procedures. In these respects. see for example Remington's Pharmaceutical Sciences, Chapter 43, 14th Ed., Mack Publishing Co., Easton, Pa. 18042, USA. These preparations can be administered in any suitable way such as by aerosol administration or parenterally, e.g., in the form of injectable solutions at suitable pH or topically, e.g. in the form of a cream. The intravenous regimen is administered in pharmacologic amounts between about 10 ng/kg to 50 mg/kg and at least about 1 µg to 1 ml/kg per day in pharmaceutically acceptable dosage form.

Preparation of Recombinant EDN

The cloning and sequencing of human EDN has been described by Rosenberg et al. 1989, Proc. Natl. Acad. Sci. USA, 86:4460–4464). Preparation of the pfCTS-EDN construct for expressing EDN is described in Rosenberg and Dyer, 1995, J. Biol. Chem., 270:21539–21544). Briefly, the cDNA sequence encoding human EDN was subcloned into the bacterial expression vector pFLAG-CTS. This vector has some unique features, including the ability to express the recombinant protein in frame with a bacterial secretion piece (ompA) which directs the recombinant protein to the periplasmic space, and the ability to express recombinant protein in frame with a C-terminal octapeptide (FLAG). The FLAG is detected by a monoclonal antibody (M2) that facilitates both isolation and detection of the recombinant protein. The inclusion of the C-terminal FLAG sequence did not interfere with the transport, folding or function of recombinant human EDN. Isolation of recombinant human EDN can be according to Rosenberg and Dyer, supra, according to H. F. Rosenberg, 1995, J. Biol. Chem., 270:7876–7881 or as follows.

One liter of bacterial culture is grown in Luria-Bertrani (LB) broth plus 100 µg/ml ampicillin overnight at 37° C. to saturation density. The culture is then divided into 4 parts, and each 250 ml aliquot is diluted to one liter with pre-warmed LB and ampicillin. After allowing culture to grow for one hour, isopropyl-1-thio-β-galactopyranoside (IPTG) (Boehringer Mannheim) is added to a final concentration of 1 µM. Bacteria are allowed to continue growing at 37° C. for 3–5 hours.

The total of 4 liters of culture are harvested using a GSA rotor at 8000 rpm for 5 minutes at 4° C. All bacterial pellets are resuspended in 200 ml phosphate buffered saline (PBS, pH 7.4) in 50 ml tubes using a SS34 rotor at 8000 rpm for 5 minutes at 4° C. The pellets are then flash frozen in ethanol on dry ice and stored at −80° C., or the preparation is continued.

The frozen pellets are resuspended in 10 ml PBS each plus 1 mM phenylmethylsulfonyl fluoride (PMSF). The suspensions are then briefly sonicated and debris is spun down using a SS34 rotor at 18,000 rpm for 10 minutes at 4° C. The centrifugation is repeated once. Sodium azide is added to the clarified bacterial lysate in 50 ml tubes to a final concentration of 0.1%, followed by addition of 0.3 to 0.4 ml M2-agarose resin. Tubes are then allowed to rotate end-over-end overnight at 4° C. The remainder of the procedure (washing, glycine elution, gel analysis) is as described in Rosenberg and Dyer, supra.

In a preferred embodiment, the EDN is prepared using baculovirus-infected Sf9 cells. A preferred nucleotide sequence for infection of insect cells is shown in SEQ ID NO:9. This nucleotide sequence encodes the polypeptide shown in SEQ ID NO:10. The final 17 amino acids of this sequence differ from the native EDN sequence, and include the carboxy-terminal octapeptide FLAG tag. The first 27 amino acids are likely a signal sequence that is cleaved prior to secretion of the protein, so that the residues at the amino terminus are "KPPQ . . . ."

Supernatants from infected cells are harvested at 96 hours post-infection. at >60% cell lysis. Cells are removed by centrifugation, and clarified supernatants are stored at −80° C. prior to use. Clarified supernatants are defrosted. and dialyzed overnight against 20 volumes of 40 mM tris, pH 8.0+1 mM NaCl. Dialyzed supernatants are subjected to high speed centrifugation to remove any remaining insoluble material, and then loaded in several aliquots over a pre-equilibrated Heparin-Sepharose column (5 ml). All column manipulations are done via FPLC (fast protein liquid chromatography) apparatus. The column loaded with supernatant material is washed with 5 volumes 50 mM tris, pH 8.0+1 mM NaCl. Proteins are eluted with a salt gradient, 50 mM tris, pH 8.0. 1 mM to 500 mM NaCl, and fractions with ribonuclease activity are combined. The volume of combined fractions is reduced to ~200μl by centrifugation over a Centricon 10 concentrator. Concentrated fractions are subjected to size separation over a Superdex G-75 column, with 50 mM tris pH 8.0+150 mH NaCl mobile phase. Fractions with ribonuclease activity evaluated by gel electrophoresis, and those apparently purified are combined. Protein concentration is determined by BCA assay. The procedure for rhEDNdK$^{38}$ differs slightly, as the protein cannot be detected by ribonuclease assay. In this case, the fractions previously determined as containing rhEDN by ribonuclease assay are combined.

Preparation of Recombinant ECP

Recombinant ECP can be prepared and purified as described in Example 5. infra, using a baculoviral vector containing the coding sequence of ECP, such as nucleotides 55–537 of the human ECP sequence having GenBank Accession No. X15161. Other suitable vectors and methods for preparing recombinant proteins are known in the art.

EXAMPLES

The following examples are presented to illustrate the present invention and to assist one of ordinary skill in making and using the same. The examples are not intended in any way to otherwise limit the scope of the invention.

Example 1

Ribonucleolytic Destruction of Virions of Respiratory Syncytial Virus by Eosinophil Secretory Proteins This example demonstrates that eosinophils have inherent antiviral activity against RSV and other enveloped single-stranded RNA viruses. In this example, RSV group A and B strains and parainfluenza virus types 1, 2 and 3 were exposed to isolated human eosinophils. The ability of these viruses to infect human target cells was measured. Following exposure to eosinophils, a dose-dependent decrease in viral infectivity was observed, an effect reversed by the addition of ribonuclease inhibitor. Reverse-transcriptase PCR analysis demonstrated ribonuclease-dependent loss of the RSV-B genome, showing that eosinophil secretory products can mediate the direct ribonucleolytic destruction of isolated virions. These results demonstrate that eosinophils function as effective antiviral agents in vitro at least in part via the actions of their secreted ribonucleases.

Materials and Methods

Preparation of viral stocks: RSV-B (ATCC Accession No. VR-1401) and CMV AD169 (ATCC Accession No. VR-538) were obtained from American Type Culture Collection (Rockville, Md.). Clinical isolates of RSV-A, parainfluenza virus types 1, 2 and 3 were obtained from Dr. Leonard B. Weiner. HEp-2 cells (Human laryngeal carcinoma) and MRC-5 (Human embryonic lung fibroblasts) cells maintained in Eagle's Minimal essential medium (EMEM)+10% heat inactivated fetal bovine serum (FBS) and 2 mM glutamine, and Rhesus monkey kidney cells (RhMK), maintained in EMEM+10% FBS were obtained from Viromed (Minneapolis, Minn.). RSV-A and RSV-B were used to inoculate 180 cm$^2$ flasks containing semi-confluent monolayers of HEp-2 cells, CMV AD169 was used to inoculate a semi-confluent monolayer of MRC-5 cells and parainfluenza virus types 1,2, and 3 were used to inoculate RhMk cells each in 50 ml maintenance media. When cytopathic effect reached approximately 80%, the supernatants were harvested, centrifuged at 2000 rpm to pellet cellular debris, then flash frozen in 1 ml aliquots.

Shell vial assay for quantifying viral infectivity: 1-dram shell vials containing round coverslips with confluent monolayers of the appropriate target cell line (HEp-2 for RSV, MRC-5 for CMV, or RhMK for parainfluenza) were obtained from Viromed (Minneapolis, Minn.). Monolayers were inspected for confluency (3–4×10$^5$ cells/monolayer) prior to use. Serial dilutions of each virus stock was prepared in maintenance media. Shell vials were inoculated with 200 μl of virus from each experimental condition, then centrifuged at 700×g at 22° C. for one hour. One ml of maintenance media was added and the shell vials were incubated at 37° C. for 16 hours (RSV and parainfluenza) or 40 hours (CMV), then fixed with acetone for 20 minutes. Immunofluorescence staining was performed by 60 minute incubations of mouse anti-RSV blend FITC-labeled monoclonal antibody (Chemicon International, Temecula, Calif.), mouse anti-parainfluenza Pan FITC-labelled monoclonal antibody (Chemicon International), or mouse anti-cytomegalovirus monoclonal antibody blend (1:300 in PBS) (Chemicon International) followed by FITC-labelled goat anti-mouse IgG (1:500 in PBS) (Kirkegaard and Perry Laboratories, Gaithersburg, Md.). Stained coverslips were mounted onto slides with FA mounting fluid, pH 7.2 (Difco Laboratories. Detroit, Mich.). Each coverslip was observed using fluorescence microscopy and the number of fluorescent cells per coverslip was determined. Triplicates were performed for all experiments.

Eosinophil isolation: Peripheral blood eosinophils were freshly isolated from normal volunteers by CD16 negative selection as described (T. T. Hansel et al., 1991. J. Immunol. Methods, 145:105–110; S. Miltenyi et al., 1990, Cytometry, 11:231–240). Briefly, 60 ml peripheral blood (per isolation) were subjected to Ficoll-Hypaque density centrifugation (Organon Teknika, Durham, N.C.). and the erythrocytes co-migrating with the granulocyte pellet were lysed with ACK lysing buffer (Biowhitaker, Walkersville. Md.). Granulocytes washed twice with PBS+0.5% BSA +1 mM EDTA (PBE) were incubated with anti-CD16-conjugated magnetic beads and isolated by magnetic activated cell sorting as per manufacturer's instructions (Milltenyi Biotec, Sunnyvale, Calif.). Eosinophils isolated by this method were 94–97% pure as determined by Quik-Diff staining (Fisher Scientific), and >95% viable by trypan blue exclusion. Eosinophils were used at a concentration of 0.4×10$^6$ cells/ml unless otherwise stated.

Neutrophil and mononuclear cell isolation: Peripheral blood neutrophils and mononuclear cell fractions were freshly isolated from normal volunteers by Ficoll-Hypaque density centrifugation (Organon Teknika). The mononuclear cell fraction was harvested and the erythrocytes co-migrating with the granulocyte pellet were lysed with ACK lysing buffer (Biowhittaker, Walkersville, Md.). The two different leukocyte fractions were washed twice with PBE. The mixed mononuclear cell fraction and the neutrophil fraction (<2% eosinophils) were resuspended in PBE and added to virus at the same concentrations used for eosinophils (0.4×10$^6$/ml).

Eosinophil treatment of viral stocks: Eosinophils isolated as described above were resuspended at 10$^7$ to 10$^8$ cells/ml in PBE, and introduced into viral stocks at concentrations varying from 0 (equivalent volume of PBE control) to 4×10$^6$ cells/ml, as indicated in each experiment. After 2 hours of gentle rotation at room temperature, eosinophils were removed by centrifugation, and the treated virus was used to transduce target cells in the shell vial assay. In experiments indicated, placental ribonuclease inhibitor (RI, 200 U/ml final concentration. Boehringer Mannheim, Indianapolis, Ind.), phorbol 12-myristate 13-acetate (PMA) (100 ng/ml, Sigma, St. Louis, Mo.), N-formyl-Met-Leu-Phe (MLP) (100 μM, Sigma), and/or ionomycin (2 μM, Sigma) was added to the virus just prior to the addition of eosinophils. In some experiments, freshly isolated human neutrophils or mononuclear cells were added to the virus at the same concentration used for the eosinophils.

Statistical Analysis: For each experiment, triplicates of each condition were performed. Error bars are indicated on each histogram to display standard deviation. Two way analysis of variance (ANOVA) was performed where indicated using Microsoft Excel 5.0 Software.

Ribonuclease assay: Generation of acid-soluble ribonucleotides from tRNA was performed as described previously (H. F. Rosenberg and K. D. Dyer, 1995, J. Biol. Chem., 270:21539–21544). Reactions were initiated by the addition of 5 or 10 μl 4 mg/ml tRNA (Sigma, St. Louis, Mo.) to 5 or 10 μl treated viral stocks in 40 mM sodium phosphate, pH 7.3 buffer, and stopped by the addition of cold 20 mM lanthanum nitrate/3% perchloric acid. Acid insoluble polymers were removed by centrifugation, and the acid soluble ribonucleotides generated were quantitated from the absorbance of the supernatant at 260 nm, with conversions and calculations as described (H. F. Rosenberg and K. D. Dyer, 1995, J. Biol. Chem., 270:21539–21544).

Detection of Intact Viral Genome by Reverse-transcriptase Polymerase Chain Reaction (RT-PCR): RNA was isolated from 1 ml volumes of treated viral stocks using RNAzol B (Teltest, Friendswood, Tex.) as per manufacturer's instructions. Complementary DNA (cDNA) was prepared from resuspended RNA using a cDNA synthesis kit (Boehringer Mannheim) with random hexamer priming. Forty cycle PCR was performed on serial dilutions of cDNA using RSV G protein specific 5' primer (ACTCATCCAAACAACCCACA; SEQ ID NO:1), and 3' primer (GGWACAAARTTGAACACTTC; SEQ ID NO:2) (J. R. Gottschalk et al., 1996, J. Clin. Micro., 34:41–43) W equals A and G, R equals T and A. Products of PCR were separated by 2.5% agarose gel electrophoresis, and the single amplification product of appropriate size was identified.

Results

To test the hypothesis that eosinophil secretory products can reduce the infectivity of single-stranded RNA viruses, the shell vial technology commonly used in clinical virology laboratories as previously described by Forbes and colleagues (B. A. Forbes et al., 1990, J. Infect. Dis., 162:39–45) was employed. This spin amplification technique allows for rapid target cell transduction by virus, followed by efficient identification of the primary virally-infected cells by immunofluorescent staining for viral-specific antigens. The results obtained from this assay have been shown to be analogous to those based on plaque forming units. Viral stocks (0.5 to 1.0×10⁶ plaque forming units/ml) were assayed at a 1:300 dilution, yielding 300–1000 stained cells per monolayer (3–4×10⁵ cells), in all experiments to follow.

Figure 1B:
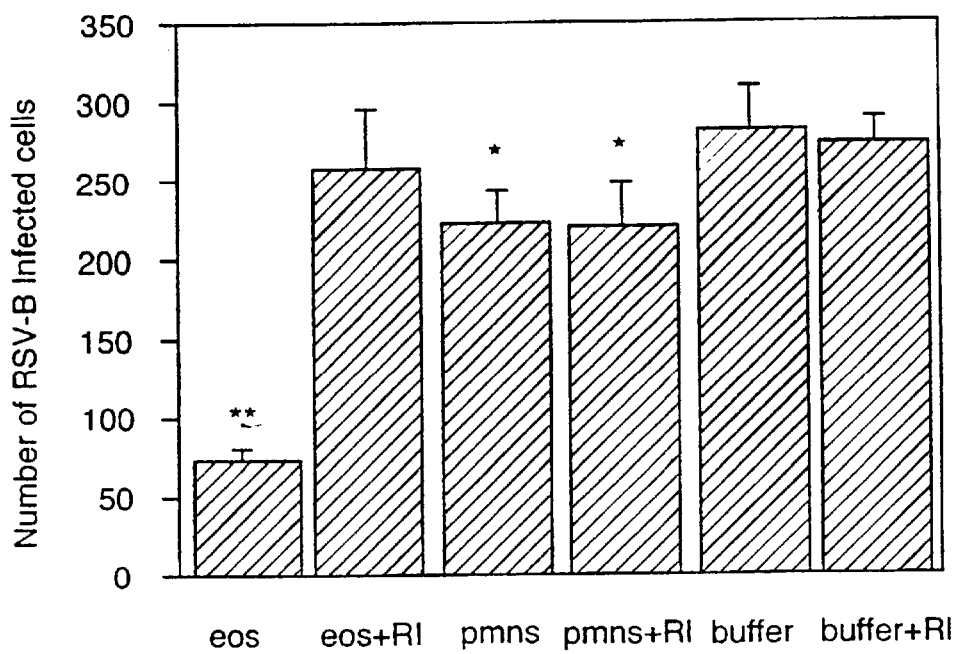
FIG. 1B shows the number of infected HEp-2 target cells per confluent monolayer after pre-treatment of RSV-B viral stocks with eosinophils+/−ribonuclease inhibitor (RI), neutrophils+/−RI, and buffer control+/−RI. Both eosinophils and neutrophils were added to viral stocks at a final concentration of $0.4 \times 10^6$ cells/ml and RI at 200 U/ml.
Figure 1C:
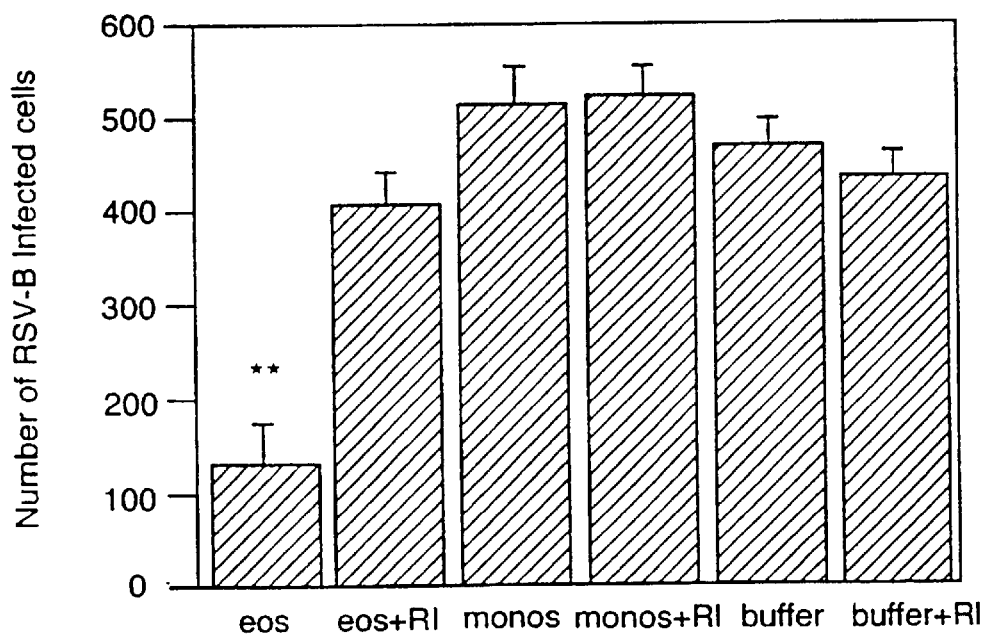
FIG. 1C shows the number of infected HEp-2 target cells per confluent monolayer after pre-treatment of RSV-B viral stocks with eosinophils+/−RI, mononuclear cells +/−RI, and buffer control+/−RI; concentration of cells and RI as in FIG. 1B. Error bars show the standard deviation for triplicate values under each condition. Two way analysis of variance (ANOVA) was applied comparing buffer control to each experimental condition. Asterisks show significance ($*p<0.05$; $**p<0.01$).
Figure 1D:
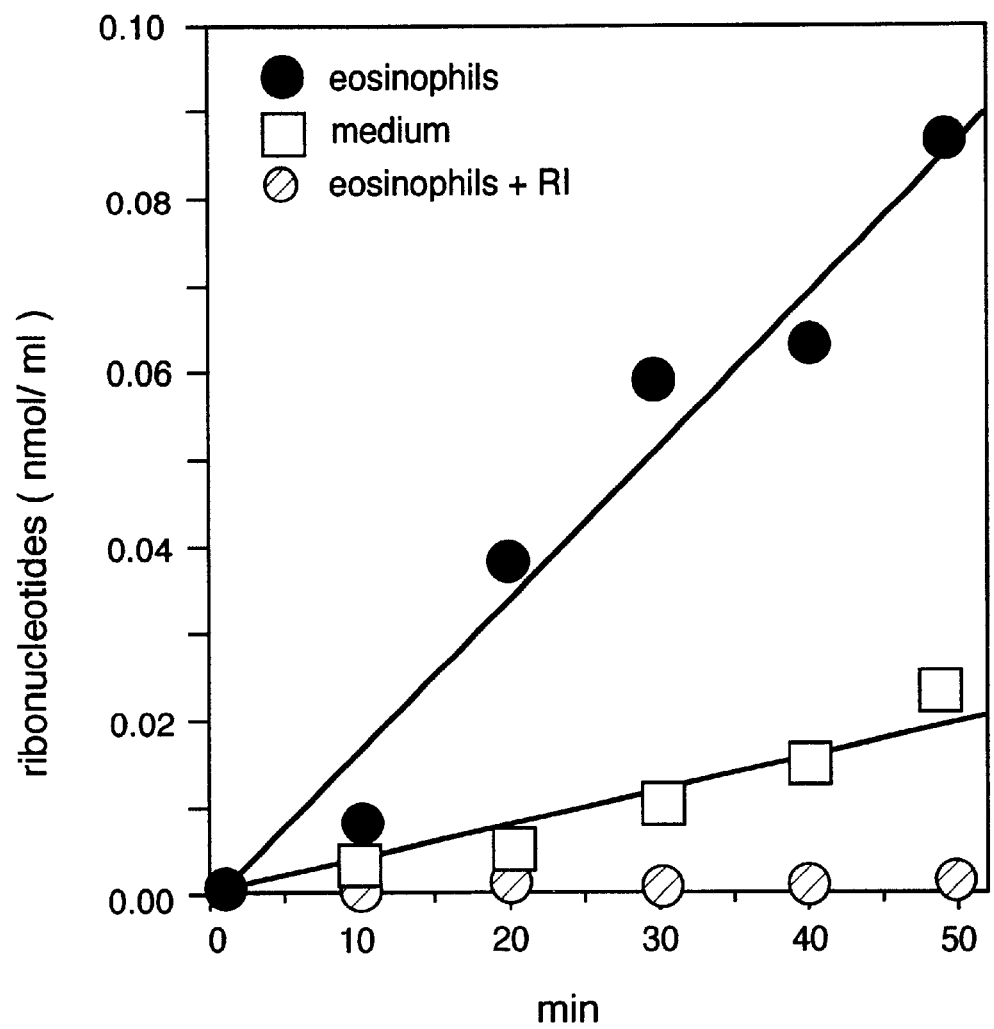
FIG. 1D shows ribonuclease activity detected in viral stocks after pretreatment with eosinophils ($0.4 \times 10^6$/ml; filled circles), buffer control (open squares), or eosinophils +RI (200 U/ml; shaded circles). Assay included 5 $\mu$l pre-treated viral stock with 20 $\mu$g yeast tRNA substrate in 0.8 ml reaction volume. Each point represents the mean of triplicate samples.

The data in FIG. 1A demonstrate that pre-incubation of viral stocks with isolated human eosinophils markedly impairs the infectivity of RSV-B, and that the degree of impairment correlates with the concentration of eosinophils within the given range (0 to 4×10⁶ per ml). At the highest eosinophil concentration (4×10⁶ per ml), a dramatic 20-fold reduction in the number of infected target cells was observed as compared to buffer controls. The ribonuclease activity detected in eosinophil-treated viral supernatants is directly proportional to the concentration of eosinophils (inset). Eosinophils were used at a concentration of 0.4×10⁶/ml in all experiments to follow. The data in FIG. 1B demonstrate that exposure of viral stocks of RSV-B to 0.4×10⁶ eosinophils/ml results in a ~4-fold reduction in viral infectivity, an effect that was reversed by the inclusion of ribonuclease inhibitor (RI) (p<0.01). Isolated human neutrophils have a slight, statistically significant ability to impair RSV-B infectivity as compared to the control (p<0.05); however, the neutrophil-mediated reduction in infectivity was not reversed by RI, suggesting a mechanism distinct from that promoted by eosinophils, potentially related to the antiviral activities characterized for the neutrophil defensins (R. I. Lehrer et al., 1985, J. Virol., 54:467–472). The analogous experiment was performed with either eosinophils or isolated human mononuclear cells incubated with RSV-B prior to target cell infection (FIG. 1C). The mononuclear cell fraction had no effect on RSV-B infectivity, while eosinophils again impaired infectivity in a ribonuclease-dependent fashion (p<0.01). Analogous to the results obtained with mononuclear cells, no loss of RSV-B infectivity was observed when viral stocks were pretreated with K562 (human erythroleukemia) or AML 3D10 (human promyelocytic leukemia (C. C. Paul et al., 1994, J. Leukoc. Biol., 56:74–79) cells. Eosinophils themselves were not infected by RSV-B as demonstrated by immunofluorescence staining after overnight incubation; the results of the experiments with RI suggest that this effect is mediated at least in part by the actions of the soluble, secreted eosinophil ribonucleases. The ribonuclease activity of eosinophil-treated (with and without RI) and buffer control-treated viral stocks was measured, as shown in FIG. 1D. These results demonstrate that granule-associated eosinophil ribonucleases are released under these experimental conditions, and that RI at the given concentration effectively inhibits their enzymatic activity.

Figure 2:
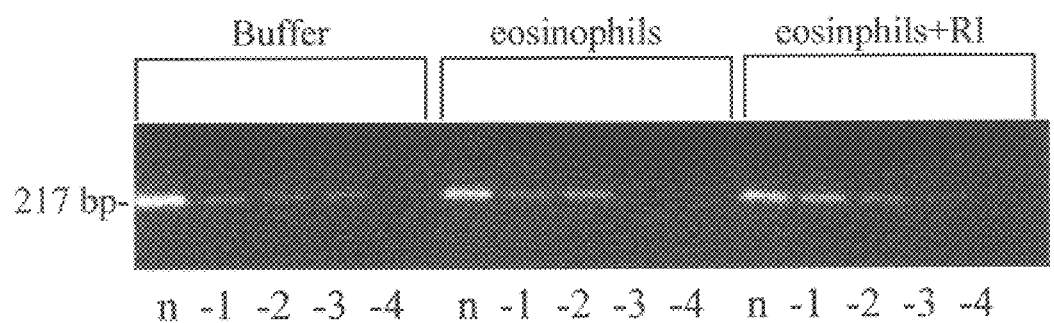
FIG. 2 shows the results of RT-PCR detection of a 217 bp segment of RSV attachment protein G representing a portion of the intact single stranded RSV viral genome. Ten-fold serial dilutions of cDNA generated from viral RNA from buffer-treated, eosinophil-treated ($0.4 \times 10^6$/ml), and eosinophils+RI-treated (200 U/ml) RSV-B viral stocks were used as templates.

FIG. 2 depicts the RT-PCR amplification of a 217 bp fragment of the 923 bp RSV-G protein gene encoded by the RSV genome. Complementary DNA (cDNA) was prepared from RNA extracted from viral stocks to which buffer alone. 0.4×10⁶ eosinophils/ml, or 0.4×10⁶ eosinophils/ml+200 U/ml RI were added; serial ten-fold dilutions of these cDNAs were used as PCR templates for amplification with gene-specific primers as described (J. R. Gottschalk, 1996, J. Clin. Micro., 34:41–43). The 217 bp amplification product was detected in the undiluted. as well as the 10-, 100- and 1000-fold diluted cDNAs prepared from the RNAs from the control- and eosinophils+RI-treated viral stocks. In contrast, the amplification product from cDNA originating in the eosinophil-treated viral stocks was visible only in the undiluted, 10- and 100-fold diluted cDNAs, representing loss of intact viral genome under these conditions. Similar results were obtained from eosinophil-treated stocks of RSV-A. These results suggest that eosinophils impair viral infectivity by ribonucleolytic destruction of the viral genome, an effect due all or in part to the activity of the secreted eosinophil ribonucleases.

Figure 3B:
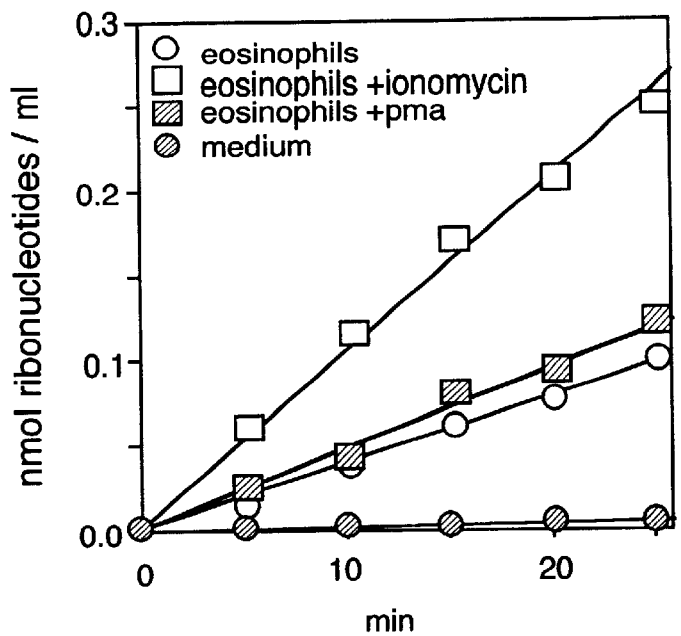
FIG. 3B shows ribonuclease activity detected in RSV-B viral stocks after pre-treatment with buffer (filled circles), eosinophils (open circles), eosinophils+PMA (shaded squares), or eosinophils+ionomycin (open squares). Assay included 10 μl pretreated viral stocks with 40 μg yeast tRNA substrate in 0.8 ml reaction volume. Each point represents the mean of triplicate samples.

As suggested by their ability to release granule-associated ribonucleases, the eosinophils used in these experiments are activated to some degree by the isolation procedure (M. Ide, 1994, J. Immunol. Methods, 168:187–196). To determine if additional eosinophil degranulation could be accomplished and to determine if such activation might serve to augment the observed antiviral effect, chemical agents known to enhance degranulation were included along with the eosinophils to the RSV-B viral stocks, including PMA (100 ng/ml), fMLP (100 $\mu$M), ionomycin (2 $\mu$M), or PMA+ionomycin (T. Fukuda et al., 1985, J. Immunol., 135:1349–1356; C. Kroegel et al., 1990, J. Immunol., 145:2581–2587). In this experiment, 2 $\mu$l of dimethylsulfoxide (DMSO) were added to the buffer and eosinophils alone conditions to account for the DMSO in which the aforementioned degranulation agents were dissolved. As shown in FIG. 3A inclusion of PMA or fMLP did not augment the observed antiviral effect over that seen for eosinophils alone. Interestingly, ionomycin, reported to be the most potent of this set of eosinophil degranulating agents (T. Fukuda et al., 1985, J. Immunol., 135:1349–1356) augmented both degranulation (FIG. 3B) as well as the observed antiviral activity to a marginal but statistically significant degree (p<0.05).

The observations on eosinophil-mediated antiviral activity were extended to include RSV-A (FIG. 4A), and parainfluenza virus types 1, 2 and 3 (FIGS. 4B, C and D, respectively), also of the family Paramyxoviridae. As anticipated, all of these enveloped, single-stranded RNA viruses display similar ribonuclease-dependent sensitivity to isolated human eosinophils. Also consistent with the hypothesis, the infectivity of the enveloped, double-stranded DNA virus, cytomegalovirus CMV AD169, was not altered by pre-incubation with human eosinophils (FIG. 4E).

Discussion

The data presented in this example demonstrate that isolated human eosinophils are active against isolated virions of the family Paramyxoviridae (RSV, parainfluenza) via the actions of their secreted ribonucleases. It is interesting to note that while eosinophils are readily recognized for their detrimental contributions to the pathophysiology of RSV bronchiolitis, their potential beneficial features have been entirely overlooked. Eosinophils can and most likely do provide an avenue of host defense against RSV and other respiratory viral pathogens, and, when the immunologic response to infection is intense, the cytotoxic properties of eosinophil granule proteins may become prominent, and exacerbate the clinical course of disease. This proposed "double-edged sword" concept of eosinophil function has parallels in the understanding of neutrophil function, with oxidative enzymes playing major roles in both antibacterial defense and host-cell free radical injury.

These data support the view that EDN and perhaps ECP, the major and minor eosinophil ribonucleases, respectively, are crucial to eosinophil-mediated antiviral activity. However, eosinophils contain several additional secretory proteins that may participate in the antiviral effect. Among these is eosinophil peroxidase (EPO), shown by Klebanoff and Coombs (S. J. Klebanoff and R. W. Coombs, 1996, AIDS Res. and Human Retroviruses. 12:25–29) to have isolated activity against clinical strains of HIV-1. In earlier studies, ECP was shown to have distinct membrane-lytic properties (J. D. E. Young et al., 1986, Nature, 321:613–616) and, along with the equally cationic major basic protein (MBP), might serve to rupture the viral envelope, rendering the RNA genome accessible for ribonucleolytic cleavage. Similarly, the eosinophil Charcot-Leyden protein (CLC) has been recently shown to bind to beta-galactoside sugars (D. D. Leonidas et al., 1995, Structure, 3:1379–1393; K. D. Dyer and H. F. Rosenberg, 1996, Life Sciences 58:2073–2082) and might participate in decreasing viral infectivity by associating with the RSV F and/or G surface glycoproteins that mediate viral penetration and attachment. respectively (P. L. Collins et al., 1996, Fields Virology 3rd Edition (B. N. Fields et al., eds.) pp. 1313–1351).

Example 2

Efficacy of Recombinant Human Eosinophil-derived Neurotoxin as an Antiviral Agent Against Respiratory Syncytial Virus in Vitro As shown in Example 1, introduction of isolated human eosinophils into stocks of respiratory syncytial virus groups A and B results in a loss of infectivity in a ribonuclease-dependent fashion. Although the ribonuclease dependence could indicate that EDN, the major eosinophil ribonuclease, is necessary for antiviral activity, it is not known from those results whether the participation of the other granule proteins (the cationic proteins ECP and MBP and/or eosinophil peroxidase (EPO)) is required. The data presented in this example demonstrate that recombinant human EDN can act alone to inactivate virion particles.

Materials and Methods

Preparation of RSV-B viral stocks: RSV-B (ATCC VR-1401) obtained from American Type Tissue Culture Collection (Rockville, Md.) were used to inoculate 180 cm$^2$ flasks of HEp-2 (human laryngeal carcinoma) cells maintained in Eagle's Minimal Essential medium (EMEM)+10% heat-inactivated fetal bovine serum (FBS) and 2 mM glutamine. When the cytopathic effect involved ~80% of the cell monolayer, the supernatants were harvested, subjected to centrifugation at ~900 g to pellet cellular debris. flash frozen in 1 ml single-use aliquots, and stored at –80° C. prior to use.

Isolation of human peripheral blood eosinophils: Peripheral blood eosinophils were freshly isolated from normal volunteers by CD16 negative selection as described (T. T. Hansel et al., 1991, J. Immunol. Methods. 145:105–110; S. Miltenyi et al., 1990, Cytometry 11:231–238). Briefly, 60 ml peripheral blood (per isolation) were subjected to Ficoll-Hypaque density centrifugation (Organon Teknika, Durham, N.C.), and the erythrocytes co-migrating with the granulocyte pellet were lysed with ACK lysing buffer (Biowhitaker, Walkersville, Md.). Granulocytes washed twice with PBS +0.5% BSA+1 mM EDTA (PBE) were incubated with anti-CD 16-conjugated magnetic beads and isolated by magnetic activated cell sorting as per manufacturer's instructions (Milltenyi Biotec, Sunnyvale, Calif.). Eosinophils isolated by this method were 94–97% pure as determined by Quik-Diff staining (Fisher Scientific), and >95% viable by trypan blue exclusion.

Preparation of recombinant proteins rhEDN and rhEDNdK$^{38}$: Creation of the recombinant plasmid constructs (pFLAG-CTS, International Biotechnologies, Inc., New Haven Conn.) and preparation of the recombinant protein was as previously described (H. F. Rosenberg and K. D. Dyer, 1995, J. Biol. Chem., 270:21539–21544). Briefly, recombinant proteins were isolated from 2–4 liters of bacterial culture after a 1 hour induction with isopropyl-1-thio-beta-galactoside. After harvest and sucrose lysis, recombinant proteins were concentrated and isolated by M2 mAb-agarose affinity chromatography (IBI). The concentration of recombinant proteins was determined by comparison to serial dilutions of a known concentration of FLAG-conjugated standard as described (H. F. Rosenberg and K. D. Dyer, 1995. J. Biol. Chem., 270:21539–21544)

Shell vial assay of viral infectivity: 1-dram shell vials containing coverslips with confluent monolayers ($3-4 \times 10^5$ cells/monolayer) of the HEp-2 human laryngeal carcinoma cell line were obtained from Viromed (Minneapolis, Minn.). Two hundred (200) microliters of pre-treated (eosinophils, rhEDN, control) RSV-B viral stock were added to each shell vial, which was then centrifuged at 700×g at 22° C. for one hour. One ml of maintenance media was added and the shell vials were incubated at 37° C. for 16 hours prior to acetone fixation and staining. Individual cells of the monolayer containing viral antigens were detected by staining with anti-RSV blend FITC-conjugated murine mAb (Chemicon International, Temecula, Calif.), followed by mounting (FA mounting fluid, pH 7.2, Difco Laboratories, Detroit, Mich.) and counting under fluorescence microscopy. Triplicates were performed for all experiments shown. The results of shell vial assay (number of infected cells/ml viral stock) have been shown to be equivalent to those determined from viral plaque assay (B. A. Forbes et al., 1990, J. Infect. Dis. 162:39–45).

Ribonuclease assay: Ribonuclease assay was described in detail in (H. F. Rosenberg and K. D. Dyer, 1995, J. Biol. Chem., 270:21539–21544). Reactions were initiated with 50 $\mu$g/ml yeast tRNA as substrate (Sigma Chemical Co., St. Louis Mo.) added to 0.8 ml reactions containing 40 mM sodium phosphate, pH 7.0 and 10 $\mu$l viral stocks treated with eosinophils, rhEDN, rhEDNdK$^{38}$, or controls. Reactions were stopped at given time points by the addition of ice-cold 3% perchloric acid with 40 nM lanthanum nitrate, and acid-soluble ribonucleotides remaining in the supernatant fraction after centrifugation were quantitated spectrophotometrically at 260 nM. All time points were performed in triplicate. Calculations included the following approximations: the average molecular weight ($M_r$) of tRNA as $M_r$=28, 100 (75–90 ribonucleotides/tRNA molecule x $M_r$=341/ribonucleotide), with $A_{260}$ of 1.0 corresponding to 40 $\mu$g of RNA (J. Sambrook et al., 1989, Molecular cloning a laboratory manual 2nd ed. Sold Spring Harbor Laboratory, Cold Spring Harbor, N.Y.). Ribonuclease inhibitor (RI) was purchased from Boehringer Mannheim, Indianapolis, Ind.

Reverse-transcriptase polymerase chain reaction (RT-PCR): RNA was isolated from 1 ml volumes of viral stocks treated with 100 nM rhEDN or 100 nm rhEDNdK$^{38}$ using RNAzol B (Teltest. Friendswood. Tex.) as per manufacturer's instructions. Complementary DNA (cDNA) was prepared from resuspended RNA using an RT-PCR first strand synthesis kit (Boehringer Mannheim) with random hexamer priming. Forty cycle PCR was performed on serial dilutions of cDNA using RSV G protein specific 5' primers and 3' primers as described (J. R. Gottschalk et al., 1996, J. Clin. Micro. 34:41–43). The PCR products were separated by 2.5% agarose gel electrophoresis and the single amplification product of appropriate size was identified.

Statistical analysis: Standard deviation, slopes and correlation coefficients ($r^2$) were determined with the assistance of Microsoft Excel software on-line at the National Institutes of Health.

Results

Figure 5:
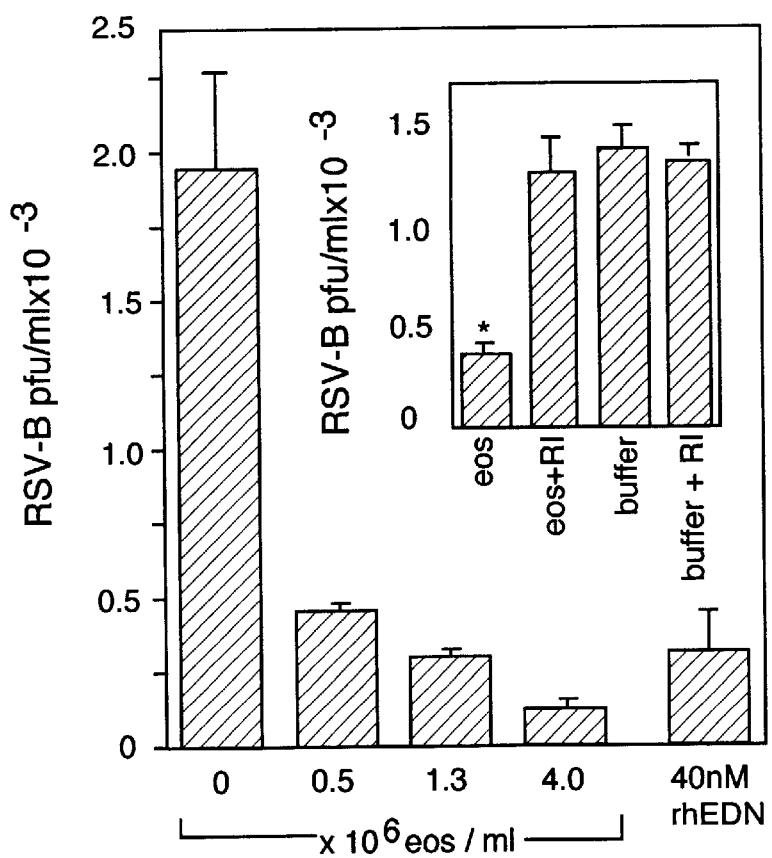
FIG. 5 shows plaque-forming units (pfu) RSV-B per ml remaining after treatment of viral stocks with isolated human eosinophils (0 to 4×10⁶/ml viral stock) or with 40 nM recombinant human EDN (rhEDN). Inset shows pfu RSV-B per ml remaining after treatment of viral stocks with isolated human eosinophils (0.4×10⁶/ml viral stock) or buffer control with or without placental ribonuclease inhibitor (RI, 200 U/ml); (*) p<0.01.

Antiviral activity of isolated eosinophils and of recombinant human EDN (rhEDN): In FIG. 5, the reduction in infectivity resulting from the presence of increasing concentrations of eosinophils (0 to 4×10⁶/ml) is compared to that mediated by 40 nM recombinant human EDN (rhEDN). These results clearly indicate that nanomolar concentrations of rhEDN can act al one to decrease viral infectivity, presenting the first potentially physiologic role for this protein. The antiviral effectiveness of rhEDN falls within the range of the two lower eosinophil concentrations (0.5 to 1.0×10⁶/ml). Interestingly, the ribonuclease activity of 40 nM rhEDN (9.0 pmol ribonucleotides/ml/min) also falls within the range of the ribonuclease activity released by 0.5 to 10×10⁶ eosinophils/ml at 8.2 and 14 pmol/ml/min, respectively (Table 1). As the recombinant protein differs somewhat from native, eosinophil-derived EDN, it is difficult to make absolute conclusions as to whether the EDN from the eosinophils is acting alone (as can rhEDN) or in concert with other eosinophil secretion products in mediating the observed antiviral effect.

TABLE 1

Ribonuclease activities of culture supernatants containing eosinophils, recombinant human EDNs, and controls. Initial rates calculated from four consecutive time points performed in triplicate; all correlation coefficients ($r^2$) at 0.90 or higher.

Figure 6A:
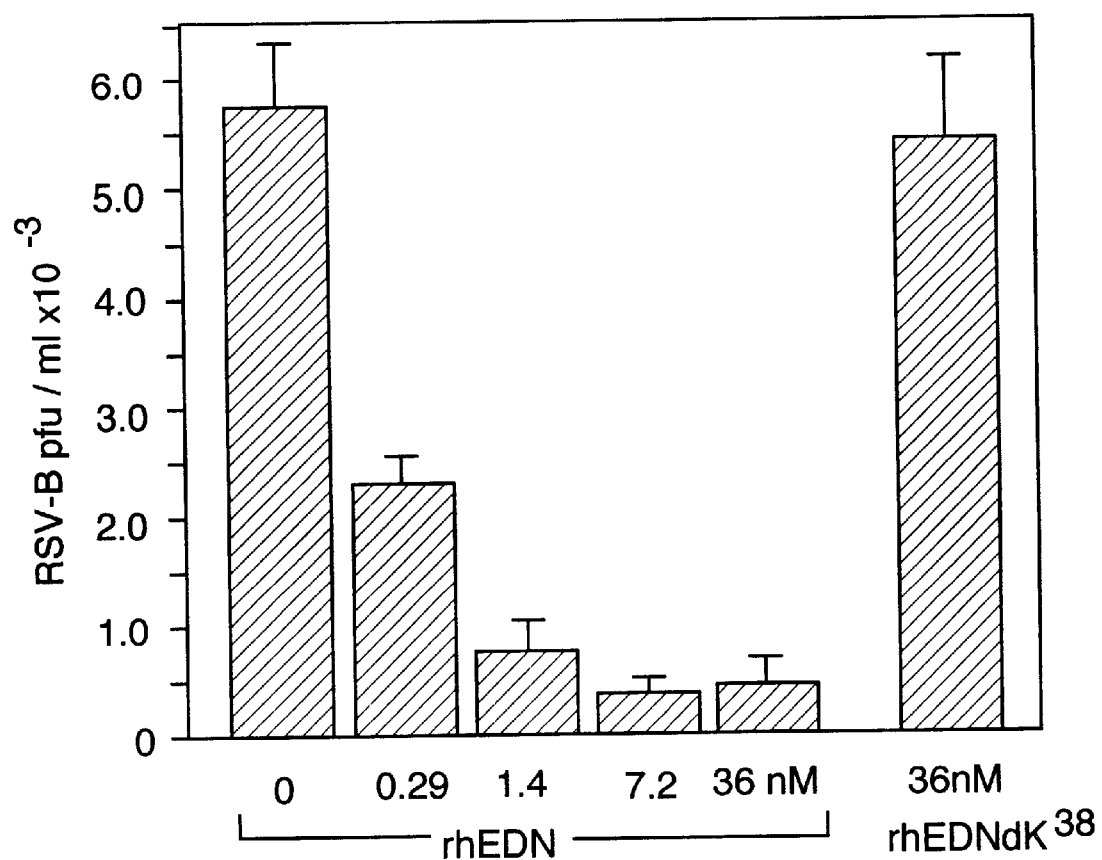
FIG. 6A is a dose response demonstrating plaque-forming units (pfu) RSV-B per ml remaining after treatment of viral stocks with rhEDN (0 to 36 nM final concentration) or with 36 nM inactivated rhEDNdK³⁸ (K³⁸ to R (Rosenberg and Dyer, 1995, J. Biol. Chem. 270:21539–21544)).
Figure 6B:
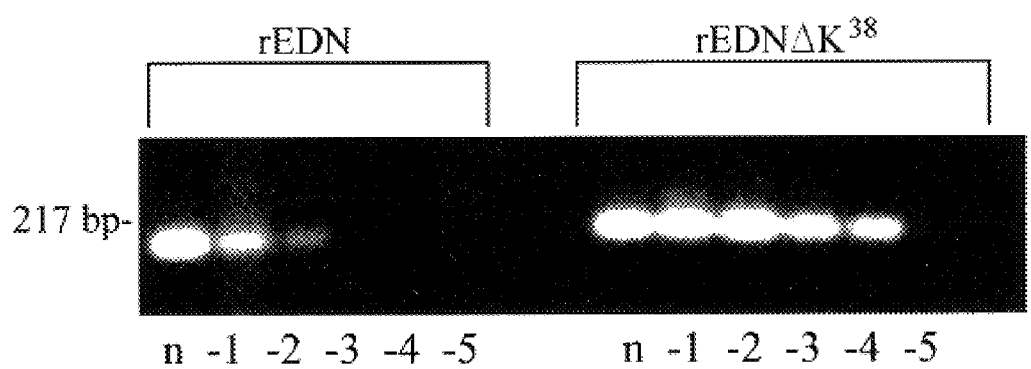
FIG. 6B shows RT-PCR detection of a 217 bp segment of the RSV G protein using serial 10-fold dilutions (n, undiluted −1, 10⁻¹ dilution) . . . −5 dilution) of cDNAs prepared from RNA isolated from virions treated with 100 nM rhEDN or 100 nM rhEDNdK³⁸.

| Agent | Specific Activity (pmol ribonucleotides/ml/min) |
|---|---|
| Eosinophils (FIG. 5): | |
| 0 eosinophils | 0.94 |
| 0.5 × 10⁶ eosinophils | 8.2 |
| 1.0 × 10⁶ eosinophils | 14 |
| 3.0 × 10⁶ eosinophils | 30 |
| 40 nM rhEDN | 9.0 |
| rhEDN (FIG. 6): | |
| 0 nM rhEDN | 0.98 |
| 0.29 nM rhEDN | 1.1 |
| 1.4 nM rhEDN | 1.8 |
| 7.2 nM rhEDN | 3.8 |
| 36 nM rhEDN | 8.2 |
| 36 nM rhEDNdK³⁸ (inactivated) | 0.97 |
| RNase A (FIG. 7): | |
| 0 nM RNase A | 0.97 |
| 40 nM RNase A | 203 |
| 400 nM RNase A | 1812 |
| 4000 nM RNase A | 22,300 |

Dose-dependence of the rhEDN-mediated anti-viral effect: The data in FIG. 6A demonstrate that the loss of viral infectivity (~6000 to 300 pfu/ml) increases in direct proportion to the concentration of rhEDN (0 to 7.2 nM rhEDN). The ribonucleolytically inactivated rhEDNdK³⁸, in which the active-site lysine of rhEDN was converted by site-directed mutagenesis to a catalytically inactive arginine (R) residue (H. F. Rosenberg and K. D. Dyer, 1995, J. Biol. Chem., 270:21539–21544) displayed no anti-viral activity in this assay. This result indicates, as anticipated from previous results with isolated eosinophils (inset to FIG. 5), that the capacity for ribonuclease activity is crucial to antiviral activity. This observation is supported by the data in FIG. 6B, in which loss of intact viral genome is observed in stocks pre-treated with 100 nM rhEDN.

Figure 7:
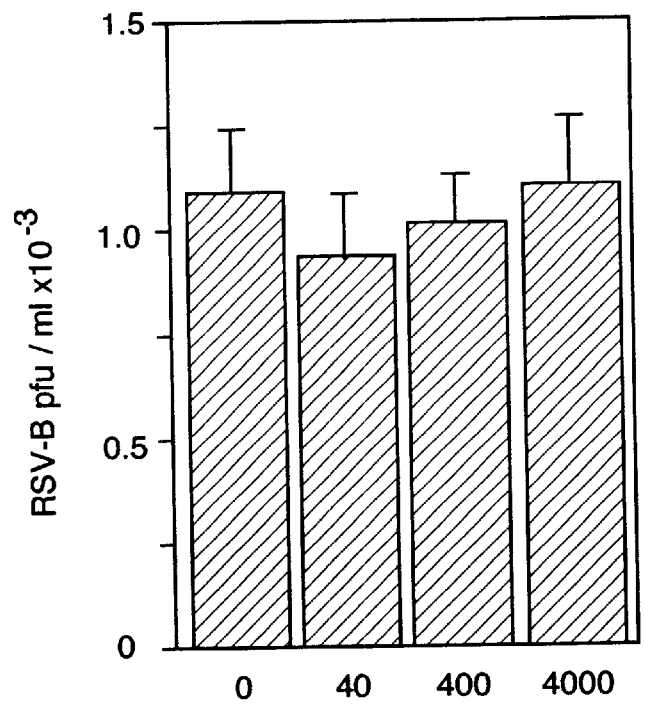
FIG. 7 shows plaque-forming units (pfu) RSV-B per ml remaining after treatment of viral stocks with bovine pancreatic RNase A (0 to 4000 nM final concentration).

Ribonuclease A (bovine pancreatic ribonuclease) has no anti-viral activity: No antiviral activity was observed with concentrations of RNase A from 40 to 4000 nM (FIG. 7). The ribonuclease activities measured for these final concentrations of RNase A range from 203 to 22,300 pmol ribonucleotides produced/ml/min, representing ~20 to 2000-fold more enzymatic activity than 40 nM rhEDN. These results indicate that while ribonuclease activity may be crucial to the antiviral activity, other properties that may be unique to rhEDN clearly contribute to its overall effectiveness.

Discussion

The data presented in this example show that rhEDN functions as a potent and effective antiviral agent against virions of the pathogen, respiratory syncytial virus, in an in vitro system. The rhEDN-mediated antiviral effect is dose-dependent at nanomolar (0.29 to 7.2 nM) concentrations, and was not replicated by a ribonucleolytically inactive form of the recombinant protein. Furthermore, introduction of RNase A (40 to 4000 nM) did not reduce viral infectivity, suggesting that while ribonuclease activity may be crucial to antiviral activity, other unique features of rhEDN are clearly necessary for this effect.

The observation that the primary structure of EDN was homologous to that of RNase A (G. J. Gleich et al., 1986, PNAS 83:3146–3150) and that EDN was a potent ribonuclease against standard substrates (N. R. Slifman et al., 1986, J. Immunol, 137:2913–2917) suggested that the physiologic function of EDN might encompass this enzymatic activity. Based on study of the evolutionary history of EDN, the gene encoding EDN has incorporated non-silent mutations at a rapid rate while maintaining all the structural and catalytic components necessary for ribonuclease activity (H. F. Rosenberg et al., 1995, Nature Genetics, 10:219–223). In its role as an antiviral agent, the ribonuclease activity of EDN has been shown to be a crucial feature.

Although rhEDN can work alone to reduce viral infectivity, this does not necessary imply that EDN does work alone under more physiologic circumstances. At first glance, the ribonucleolytic activity and the antiviral potency of 40 nM rhEDN and that 0.5 to 1.0×10⁶ eosinophils/ml are within range of each other, suggesting EDN as the sole mediator of the antiviral effect. However, the recombinant protein differs somewhat from native EDN, most notably in that it lacks the extensive glycosylation characteristic of EDN both within granules and released from activated eosinophils (H. F. Tiffany et al., 1995, J. Leukoc. Biol., 58:49–54). The combined ribonucleolytic, membrane lytic, and oxidative properties of the four major eosinophil granule proteins may each contribute to the antiviral activity of human eosinophils (G. J. Gleich, 1992, in Inflammation: basic principles and clinical correlates (J. I. Gallin et al., eds.) Raven Press Ltd., New York, pp. 663–680) (S. J. Ackerman, 1993, in Eosinophils. Biological and clinical aspects (S. Makino, T. Fukuda. eds) CRC Press, Boca Raton, Fla. pp. 33–70).

Introduction of RNase A, even at the highest concentrations, results in no loss in viral infectivity, suggesting that other features of EDN, in addition to its ribonuclease activity, are crucial to its antiviral activity. One issue is cationicity; although not as cationic as ECP or eosinophil major basic protein, the calculated pI of EDN is 8.9, well above neutrality, and above that of RNase A (calculated pI=4.8). Membrane perturbation by cationic proteins such as ECP (J. D. E. Young et al., 1986, Nature, 321:613–616) and the neutrophil defensins (E. Martin et al., 1995, J. Leukoc. Biol. 58:128–136) has been studied in detail. The possibility that EDN has as yet uncharacterized membrane-perturbing features is intriguing, and would go a long way toward explaining how EDN finds access to the viral genome.

Example 3

Eosinophil Inhibition of Retroviral Transduction of Human Target Cells by a Ribonuclease-dependent Mechanism In this example, stocks of a replication-defective retrovirus, Moloney murine leukemia virus, modified to encode the reporter gene beta-galactosidase were pre-treated with isolated human eosinophils, then used to transduce human erythroleukemia (K-562) target cells. The results presented in this example demonstrate that eosinophils function as effective anti-retroviral agents in vitro via the actions of their secreted ribonucleases.

Materials and Methods

Preparation of retroviral stocks: The psi-crip packaging cell line transfected with the pMFGS-βgal retroviral construct (O. Danos and R. C. Mulligan, 1988. Proc. Natl. Acad. Sci. USA, 85:6460–6064) was a generous gift of Dr. Harry Malech. High titer viral stocks were isolated as supernatants of replicate cultures of transfected cells grown to confluence in Iscove's modified Dulbecco's medium (IMDM)+10% fetal calf serum (FCS)+2 mM glutamine and stored at −80° C. prior to use.

Eosinophil isolation: Peripheral blood eosinophils were isolated from normal volunteers by CD16 negative selection as described (T. T. Hansel et al., 1991, J. Immunol. Methods, 145:105–110; S. Miltenyi et al., 1990, Cytometry, 11:231–238). Briefly, 100–200 ml peripheral blood (per isolation) were subjected to Ficoll-Hypaque density centrifugation (Organon Teknika, Durham, N.C.), and the red blood cells co-migrating with the granulocyte pellet were lysed with ACK lysing buffer (Biowhittaker, Walkersville, Md.). Granulocytes washed twice with PBS+0.5% BSA+1 mM EDTA (PBE) were incubated with anti-CD 16-conjugated magnetic beads and isolated by magnetic activated cell sorting as per manufacturer's instructions (Miltenyi Biotec, Sunnyvale, Calif.). Eosinophils were isolated by this method to >97% purity (<3% contamination with mononuclear cells) as determined by Quik-Diff staining (Fisher Scientific), and >95% viability by trypan blue exclusion.

Eosinophil pre-treatment of viral stocks: Eosinophils isolated as described above were resuspended at $10^7$ to $10^8$ cells/ml in PBE, and introduced into viral stocks at concentrations varying from 0 (equivalent volume of PBE control) to $3\times10^6$ cells/ml, as indicated in each experiment. After 2 hours of gentle rotation at room temperature, eosinophils were removed by centrifugation, and the pre-treated viral stocks were used to transduce target K-562 human erythroleukemia target cells. In experiments indicated, placental ribonuclease inhibitor (RI, 40 U/ml, Boehringer Mannheim, Indianapolis, Ind.) was added to the viral stocks just prior to the addition of eosinophils.

Target cell transduction and histochemical staining: Transduction of cells of the K-562 human erythroleukemia cell line was performed as described previously (J. B. Domachowske et al., 1996, Blood, 88:2980–2988). Briefly, 0.5 ml of viral stocks pretreated as described above were added to 0.5 ml exponential-phase cultures of K-562 cells (grown in RPMI+10% FCS+2 mM glutamine+penicillin/ streptomycin) in 24 well plates. Protamine (4 mg/ml) was added. and the cells and viral stocks were centrifuged together at 900 g, 32° C. for 1 hour. The cells together with the viral stock were then rested in a 5% $CO_2$ incubator at 37° C. for 1 hour, harvested and resuspended in 0.5 ml of the RPMI complete medium as described above. This procedure was repeated sequentially for a total three times to facilitate high efficiency target cell transduction. After the final resuspension, cells were cultured for an additional 48 hours in 5% $CO_2$ at 37° C. prior to fixation and histochemical staining for beta-galactosidase expression. which was performed as described (E. J. Murray and J. M. Walker, 1991, Methods in Molecular Biology, Humana Press Inc., Clifton, N.J., 7:217–235). Viability of target cells treated with control (PBE alone) and eosinophils (to $1\times10^6$/ml) remained >98% throughout the course of the experiment. Each experimental point represents the average of triplicate sample cultures with 500–800 cells scored per sample. Each scoring was performed independently by two observers, one blinded to the specific experimental conditions. Significance by analysis of variance (ANOVA) testing was as indicated in each experiment.

Ribonuclease assay: Generation of acid-soluble ribonucleotides from tRNA was performed as described previously (H. F. Rosenberg and K. D. Dyer, 1995, J. Biol. Chem., 270:21539–21544). Reactions were initiated by the addition of 8 μl 4 mg/ml tRNA (Sigma, St. Louis, Mo.) to 10 μl pre-treated viral stocks in an 0.8 ml reaction volume containing 40 mM sodium phosphate, pH 7.3 buffer, and stopped by the addition of cold 20 mM lanthanum nitrate/ 3% perchloric acid. Acid insoluble polymers were removed by centrifugation, and the acid soluble ribonucleotides generated were quantitated from the absorbance of the supernatant at 260 nm, with conversions and calculations as described (H. F. Rosenberg, and K. D. Dyer, 1995, J. Biol. Chem, 270:21539–21544).

Western blots: After high speed centrifugation, supernatants of viral stocks pretreated with eosinophils ($3\times10^6$/ml), eosinophils and ribonuclease inhibitor (RI, 200 U/ml), or buffer alone were subjected to gel electrophoresis and Western blotting as described (M. Ide et al., 1994, J. Immunol. Meth., 168:187–196). Blots were probed with 1:300 dilutions of either polyclonal anti-EDN or anti-ECP, pre-treated to remove cross-reacting antibodies, followed by a 1:1000 dilution of alkaline-phosphatase conjugated goat anti-rabbit IgG (Biorad, Richmond. Calif.). Blots were developed with nitroblue tetrazolium and 5-bromo-4-chloro-3-indolyl phosphate (Biorad).

Detection of intact viral genome by reverse-transcriptase polymerase chain reaction (RT-PCR): RNA was isolated from 1 ml volumes of eosinophil or buffer pre-treated viral stocks using RNAzol B (Teltest, Friendship, Tex.) as per manufacturer's instructions. Complementary DNA (cDNA) was prepared from resuspended RNA using a cDNA synthesis kit (Boehringer Mannheim) with a beta-galactosidase gene specific primer (priming negative-stranded RNA, bp 2701 to 2721, 5'-GGG CCG CAA GAA AAC TAT CCC-3'; SEQ ID NO:3). Thirty-five cycle PCR was performed on serial dilutions of cDNA using this sequence as the 5' primer, and bp 2870 to 2850, 5'-AAC TGG AAG TCG CCG CGC CAC-3'; SEQ ID NO:4 as the 3' primer. Products of PCR were separated by 2.5% agarose gel electrophoresis, and the single amplification product of appropriate size was identified.

Results

Figure 8A:
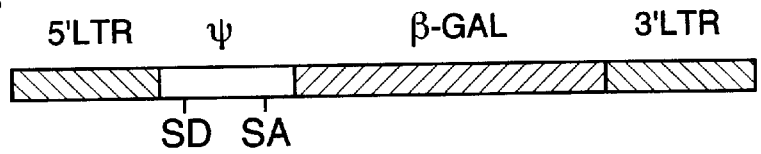
FIG. 8A is a schematic of the pMFGS-Bgal engineered retroviral genome. LTR, long terminal repeat; ψ, packaging sequence; SA, splice acceptor; SD, splice donor. Retroviral stocks were harvested from cultures of transfected cells of the psi-crip amphotrophic packaging line, source of retroviral gag, pol, and env proteins sufficient for a single round of target cell transduction.

In this model system, cellular transduction by retroviruses in vitro mimicked as much as possible events occurring in vivo, while at the same time provided a rapid and reproducible measure of changes in viral titer. The engineered retrovirus, pMFGS-βgal (O. Danos, and R. C. Mulligan, 1988, Proc. Natl. Acad. Sci. USA, 85:6460–6064) is uniquely suited to this type of experiment (FIG. 8A). In this construct, the retroviral gag, pol, and env genes are replaced by the beta-galactosidase reporter gene, providing a histochemical marker for transduced target cells. Initial transfection of the psi-crip packaging cell line (O. Danos and R. C. Mulligan, 1988, Proc. Natl. Acad. Sci. USA, 85:6460–6064) results in release of viral particles into the culture supernatant (=viral stock) with quantities of viral proteins sufficient for a single round of target cell transduction.

Figure 8B:
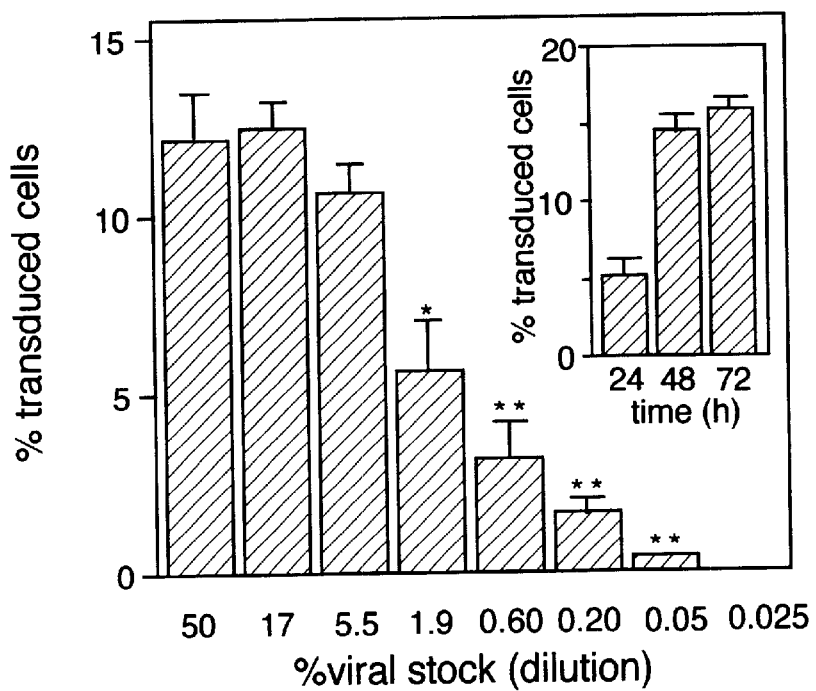
FIG. 8B shows transduction efficiency of serial dilutions of viral stock. Target K-562 human erythroleukemia cells were harvested at t=48 hrs and transduced cells were identified by histochemical staining for beta-galactosidase activity. Analysis of variance (ANOVA) testing demonstrated the significance of the differences between the groups indicated at the p<0.05 (*) and p<0.01 (**) levels. Inset: time dependence of the transduction efficiency as determined by histochemical staining.

The results of histochemical staining of human target cells (K-562 erythroleukemia) transduced with serial dilutions of viral stock is shown in FIG. 8B. When transductions were performed with a 50% dilution of viral stock in culture medium, 12.2+/−1.3% of the target cells were transduced; dilution of the viral stock to 1.9% reduced the transduction efficiency to 5.5+/−1.8%, as determined at t=48 hours after transduction. These results demonstrate a correlation between viral titer and transduction efficiency within a specific range of dilutions.

By comparing the eosinophil-mediated reduction in transduction efficiency to reductions resulting from viral dilution, one can assess the loss of viral titer directly. The results in the inset to FIG. 8B suggest that measurable histochemical staining increases between 24 to 48 hours, remaining relatively stable from 48 to 72 hours. Transductions were performed with the 50% dilution of viral stock, and staining performed at t=48 hours in all experiments to follow.

Figure 9A:
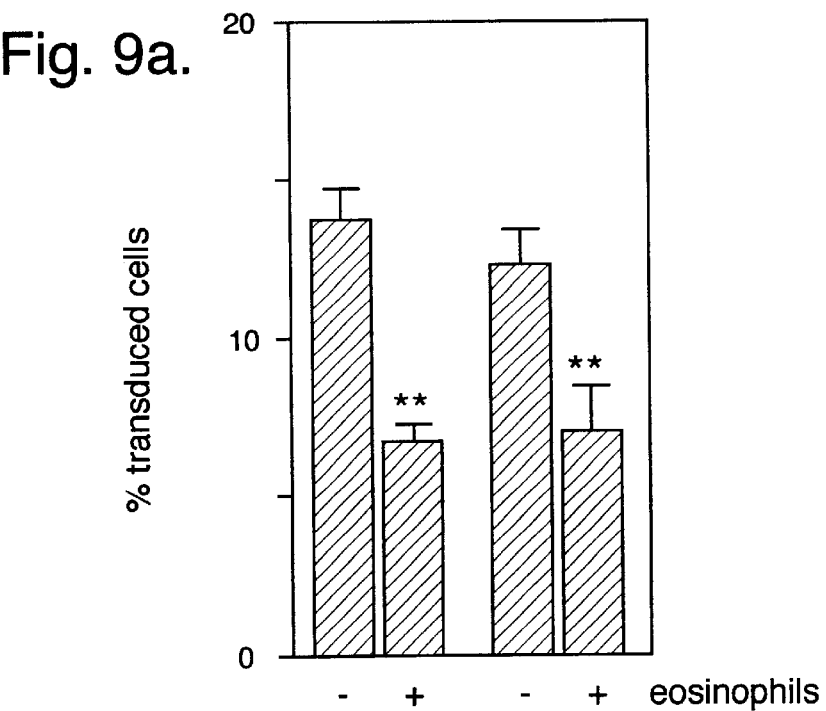
FIG. 9A shows results of independent trials demonstrating the reduction in transduction efficiency resulting from pre-treatment of viral stocks with human eosinophilic leukocytes (0.4×10⁶ per ml viral stock); the reduction in transduction efficiency achieved by pre-treatment with eosinophils corresponds to that observed with a ~20-fold dilution of the viral stock (50% to 2–3%.
Figure 9B:
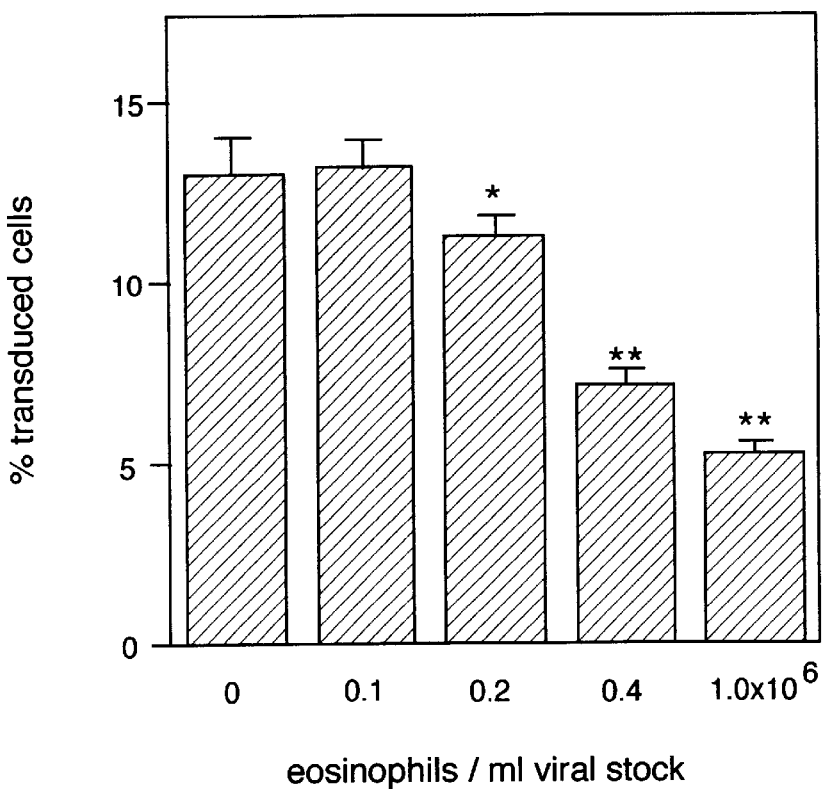
FIG. 9B shows dependence of the transduction efficiency on concentration of eosinophils per ml viral stock. ANOVA testing demonstrated the significance of the differences between the reduced and control conditions at the p<0.05 (*) and p≦0.01 (**) levels.

The results of two independent trials in which retroviral particles were pre-treated with human eosinophils ($0.4 \times 10^6$/ml) or with buffer control (PBE) prior to target cell transduction are shown in FIG. 9A. In both cases, the transduction efficiency was reduced from 12.4–13.5% to 6.5–7.0% reflecting a reduction in viral titer to 2 to 3% as demonstrated by the results shown in FIG. 8B. The results shown in FIG. 9B demonstrate that greater reductions in transduction efficiency are achieved in proportion to the concentration of eosinophils used to pre-treat the viral stocks. No differences in the growth and viability (>98% by trypan blue exclusion) of the target K-562 cell cultures were observed at any of the eosinophil concentrations shown (0 to $1 \times 10^6$/ml). Neither the eosinophils nor the control cells (see later) used to pre-treat viral stocks were not transduced by the retrovirus (as determined by histochemical staining), as the procedures facilitating high efficiency transduction were not performed until after they were removed from the viral stocks.

Figure 9C:
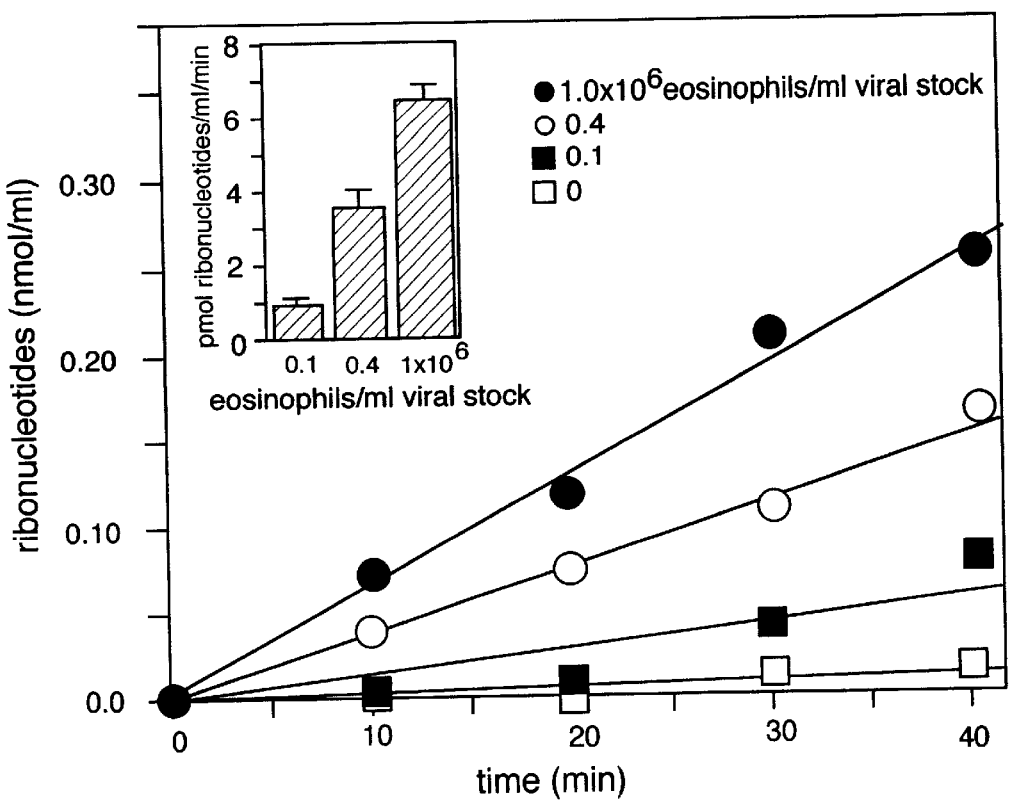
FIG. 9C shows ribonuclease activity released by eosinophils degranulating in retroviral stocks. Inset shows reaction rates (pmol/ml/min) versus eosinophil concentration (cells/ml viral stock) corrected for rate observed in the absence of eosinophils.

In the experiments shown in FIG. 9C, ribonuclease activity in both eosinophil- and PBE (control)-treated viral stocks was measured. The results demonstrate that the eosinophils degranulate, releasing the granule ribonucleases under these experimental conditions. Similar to the observed reduction in transduction efficiency (FIG. 9B), the increase in ribonuclease activity was directly proportional to the concentration of eosinophils added to the viral stock (inset to FIG. 8B).

Interestingly, release of ribonucleases into the culture medium occurred in both the presence and absence of viral particles. While this does not rule out the possibility of a specific virus-eosinophil interaction, the eosinophils are activated to some degree by the isolation procedure (H. F. Rosenberg, and H. L. Tiffany, 1994, J. Leukoc. Biol., 56:502–506) and additionally by components present in fetal calf serum of the cell culture medium.

Figure 9D:
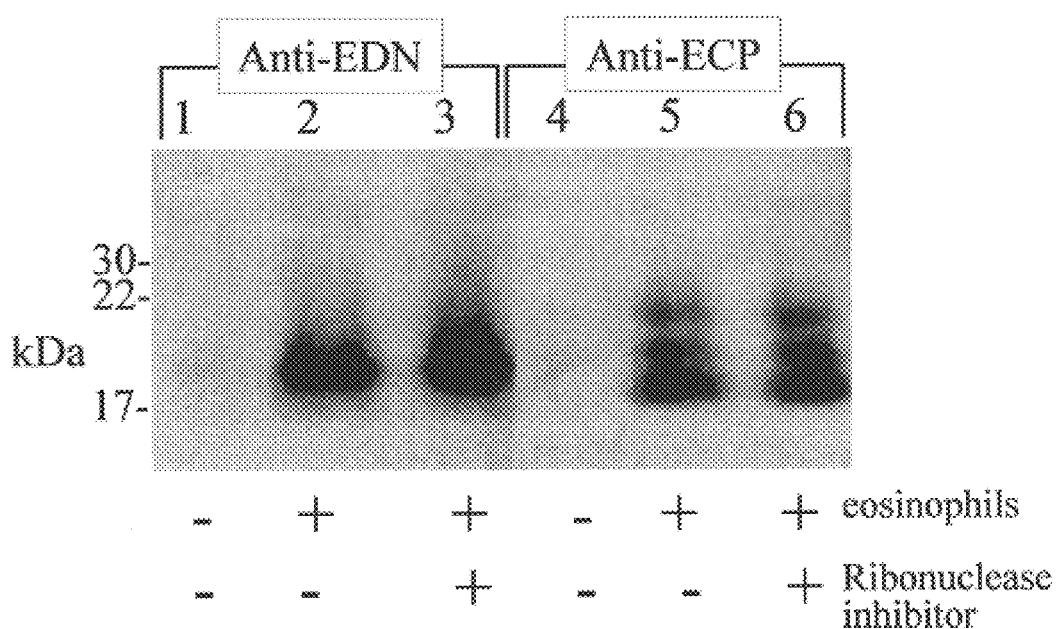
FIG. 9D shows detection of EDN and ECP in supernatants of viral stocks treated with eosinophils (3×10⁶/ml). Western blots were probed with polyclonal anti-EDN (lanes 1–3) or anti-ECP (lanes 4–6). In lanes 3 and 6, RI (200 U/ml) was added to the viral stocks prior to the addition of eosinophils.

The release of the eosinophil ribonucleases EDN and ECP into the viral supernatants was demonstrated directly by Western blotting (FIG. 9D). In addition to confirming degranulation, these results indicate that the addition of ribonuclease inhibitor (RI) has no demonstrable effect on the release of EDN or ECP under these experimental conditions.

Figure 9E:
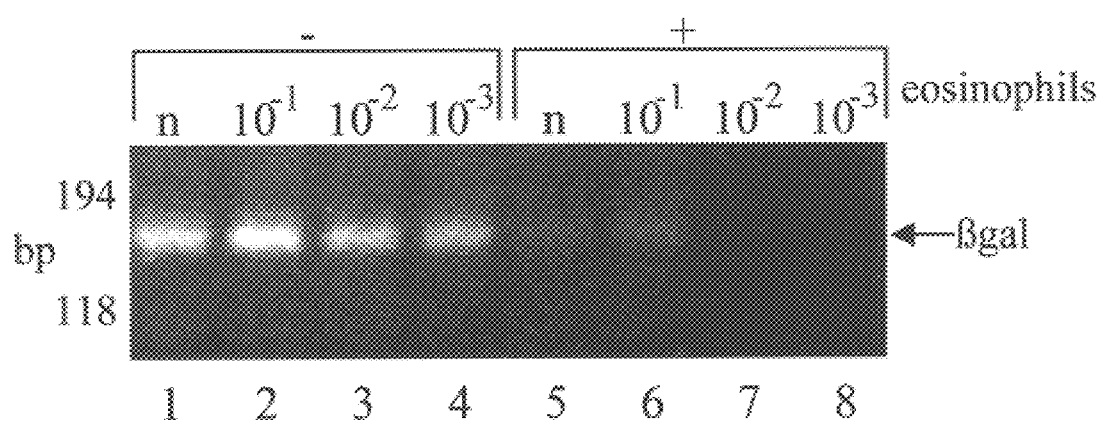
FIG. 9E shows RT-PCR detection of a 170 bp segment of the beta-galactosidase gene representing a portion of the intact retroviral ssRNA genome. Serial dilutions of cDNA generated from retroviral RNA from control-treated (lanes 1–4) and eosinophil-treated (lanes 5–8) viral stocks were used as templates for 35-cycle PCR.

In FIG. 9E, semi-quantitative RT-PCR amplification of a 3'-segment of the beta-galactosidase gene encoded by the retroviral genome is shown. Serial dilution of the cDNA templates prior to PCR indicates that there was significantly less (~100 fold) retroviral RNA remaining intact after eosinophil-pretreatment than in those retroviral stocks treated with PBE (control) buffer alone.

Figure 10A:
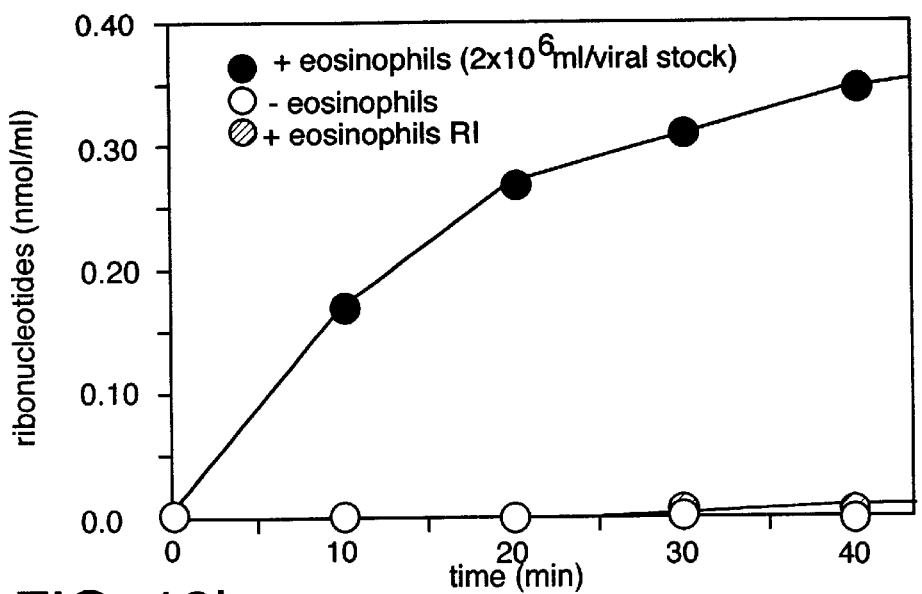
FIG. 10A shows inhibition of ribonuclease activity with placental ribonuclease inhibitor (RI, 40 U/ml).
Figure 10B:
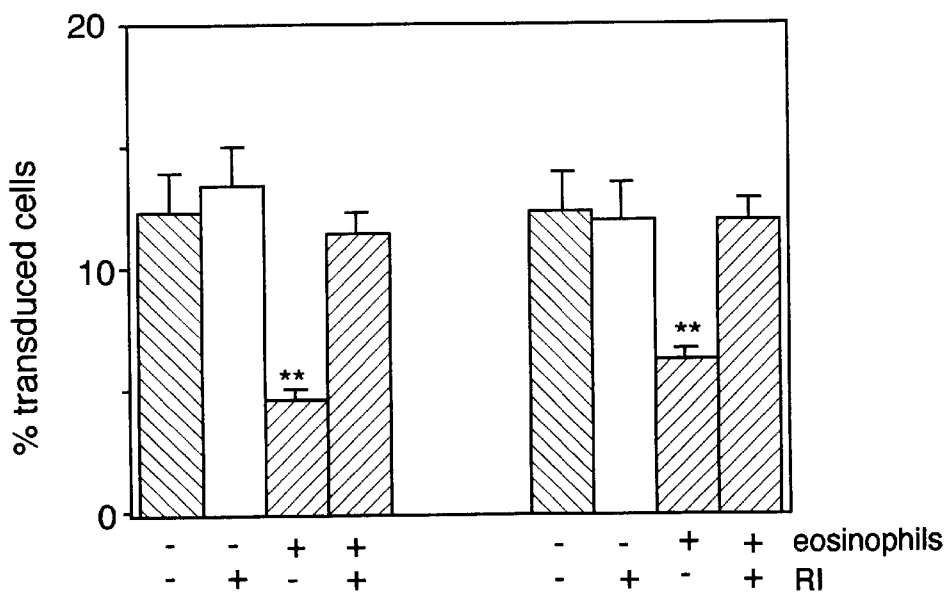
FIG. 10B shows that eosinophil-mediated reduction in retroviral transduction efficiency (0.4×10⁶ eosinophils/ml viral stock) is reversed in the presence of RI (40 U/ml), difference significant at the p<0.01 level (**)

As shown in FIG. 10A, placental ribonuclease inhibitor (RI) will inhibit the ribonuclease activity released from the eosinophils, as anticipated from results of earlier studies indicating sensitivity of EDN to the effect of this inhibitor (H. F. Rosenberg and K. D. Dyer, 1995, J. Biol. Chem., 270:21539–21544). The results of two independent trials in which RI (40 U/ml) was added to the viral stock immediately prior to the addition of either eosinophils ($0.4 \times 10^6$/ml) or buffer control are shown in FIG. 10B. In the presence of RI, the eosinophil-mediated reduction in transduction efficiency disappeared, and the percentage of tranduced cells reverted to control level.

Figure 10C:
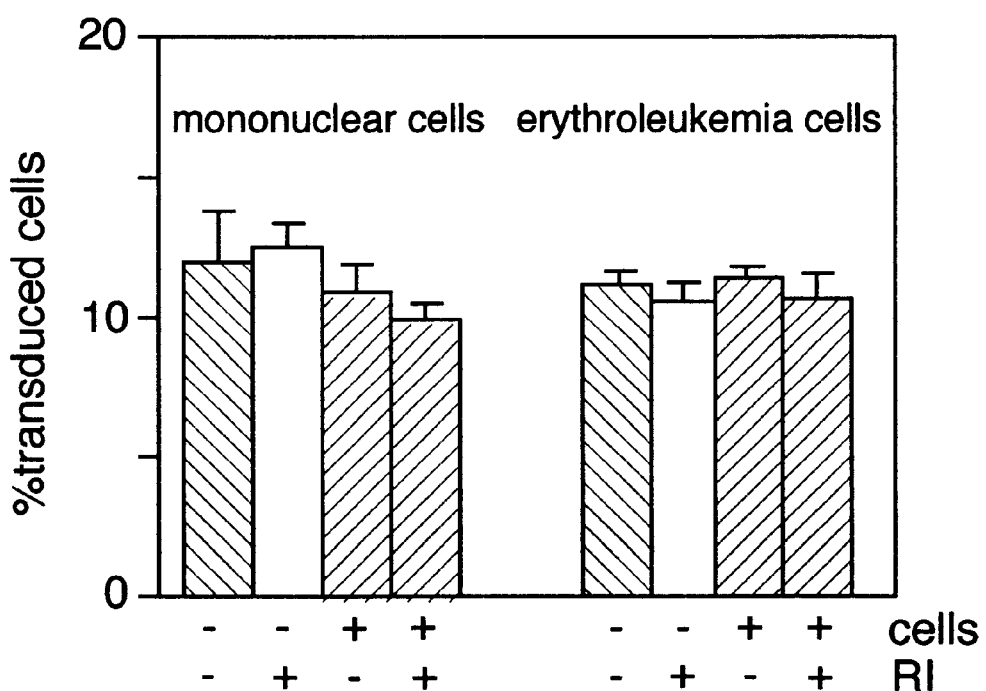
FIG. 10C shows the transduction efficiency observed with pre-treatment of viral stocks with control cells, including human peripheral blood mononuclear or K-562 erythroleukemia cells (0.4×10⁶/ml), with or without RI.

This finding suggests that ribonuclease activity released by eosinophils is crucial to the antiviral effect, and rules out such mechanisms as non-specific viral binding or incorporation by eosinophils. The results of pre-treatment of viral stocks with control (non-eosinophilic) cells is shown in FIG. 10C. No reduction in transduction efficiency was observed with pre-treatment of viral stocks with either isolated human mononuclear cells or with cells of the K-562 erythroleukemia cell line.

Discussion

These results indicate that eosinophils are capable of interfering with retroviral transduction of human target cells via a ribonuclease-dependent mechanism and point to the direct destruction of retroviral particles by the actions of the secreted granule proteins. EDN is the most active of the two ribonucleases, and thus likely to be crucial to the antiviral effect.

While eosinophils are not generally perceived as participants in host defense against viral disease, this impression may be changing. In their study of 855 HIV-infected patients, Cohen and Steigbigel (A. J. Cohen and R. T. Steigbigel, 1996, J. Inf. Dis., 174:615–618) noted a pronounced eosinophilia in a subgroup of patients and concluded that the HIV retroviral infection itself may have induced proliferation of eosinophils. Indeed, Klebanoff and Coombs (S. J. Klebanoff and R. W. Coombs, 1996, AIDS Res. and Human Retroviruses, 12:25–29) demonstrated that stimulated eosinophils and eosinophil peroxidase inhibited cellular transduction by a strain of HIV-1. Furthermore, eosinophils and their granule proteins have been implicated in the pathogenesis of infections caused by respiratory syncytial virus (RSV).

Several groups have shown that during RSV infection eosinophils are recruited to, and degranulate in the lung parenchyma (R. Garofalo et al., 1992, J. Pediatrics, 120:28–32; E. A. Colocho Zelaya et al., 1994, Ped. All. Immunol., 5:100–106; P. J. Openshaw, 1995, Am. J. Respir. Crit. Care Med., 152:59–62; N. Sigurs et al., 1994, Acta Paediatr., 83:1151–1155). Stark and colleagues (J. M. Stark et al., 1996, J. Immunol., 156:4774–4782) have shown that cultured respiratory epithelial cells infected with RSV support increased adherence of activated eosinophils, Kimpen and colleagues (J. L. L. Kimpen et al., 1992, Pediatric Res., 32:160–164) present evidence suggesting direct activation of eosinophils exposed to RSV in vitro.

Example 4

Identification of a Specific Carboxy-terminal Sequence Necessary for Enhanced Ribonuclease Activity The data presented in this example indicate that the Arg and/or lie residues adjacent to the carboxy-terminus are necessary (but not sufficient) for enhanced ribonuclease activity among the primate EDNs, and permit prediction of the relative ribonuclease activities based on differences in primary structure. This example demonstrates the preparation of recombinant EDN proteins from sequences derived from orangutan (Pongo pygmaeus, oEDN), Old World monkey (*Macaca fascicularis*, mcEDN), and from a second New World monkey sequence (*Aotus trivirgatus*, omEDN).

Materials and Methods

Isolation of EDN Gene from Owl Monkey (*Aotus Trivirgatus*): The intronless coding sequence of owl monkey EDN (omEDN) was isolated by polymerase chain reaction (PCR) as described (H. F. Rosenberg et al., 1995. Nature Genetics, 10:219–223). A 3' primer encoding a segment of the 3' untranslated region of human EDN was used in order to identify precise sequence at the 3' end of the coding sequence. The source of PCR template was genomic DNA isolated from the owl monkey kidney cell line OMK (637–69) from the American Type Culture Collection (cat. no. CRL-1556). All sequence analysis and comparisons were performed with the assistance of the Wisconsin Genetics Computer Group programs available on-line at the National Institutes of Health.

Preparation of chimeras: Chimeras were created by overlapping PCR mutagenesis as described (H. F. Rosenberg and K. D. Dyer, 1995, J. Biol. Chem., 270:21539–21544; Higuchi, R. (1990) PCR Protocols Chapt 22, Academic Press. San Diego, Calif.) with amplification primers designed to facilitate direct cloning into the pFCTS bacterial expression vector (International Biotechnologies, Inc., New Haven Conn.) as described below. All chimeras were confirmed by dideoxy-sequencing.

Expression constructs and isolation of recombinant protein: All primate EDNs were PCR amplified with primers containing restriction sites facilitating direct cloning into the pFCTS bacterial expression vector (IBI); all constructs were confirmed by dideoxy-sequencing. The pFCTS vector adds the octapeptide DYKDDDK ("FLAG"; residues 145–152 of SEQ ID NO:7) to the recombinant protein which permits its isolation and detection using the M2 anti-FLAG monoclonal antibody (mAb). As shown previously, the FLAG octapeptide does not interfere with the folding or the catalytic activity of recombinant ribonucleases (H. F. Rosenberg and K. D. Dyer, 1995, J. Biol. Chem., 270:21539–21544; H. F. Rosenberg, 1995, J. Biol. Chem., 270:7876–7881). Recombinant proteins were isolated from 2–4 liters of bacterial cultures after a 1 hr induction with isopropyl-1-thio-beta-galactoside (IPTG). After harvest and sucrose lysis, recombinant proteins were concentrated and isolated by M2 mAb-agarose affinity chromatography (IBI) as described in detail in H. F. Rosenberg and K. D. Dyer, 1995, J. Biol. Chem, 270:21539–21544. The concentration of recombinant protein was determined by comparison to serial dilutions of a known concentration of FLAG-conjugated standard as described (H. F. Rosenberg and K. D. Dyer, 1995, J. Biol. Chem, 270:21539–21544).

Ribonuclease assay and double reciprocal plots: Reactions were carried out with varying concentrations of yeast tRNA (Sigma Chemical Co., St. Louis, Mo., cat. no. R-9001) added in separate reactions to 0.8 ml of 40 mM sodium phosphate, pH 7.0, containing recombinant EDN at concentrations indicated. The assay, solutions, conditions and t=0 controls were as described in Rosenberg and Dyer, supra. The ribonuclease activity from sham isolates (M2-resin equilibration and glycine elution of periplasmic proteins isolated from equivalent volumes of pFCTS-vector alone bacterial transfectants) was determined; the sham isolates had levels of ribonuclease activity that were insignificant when compared to hEDN, oEDN and mcEDN, and represented no more than 20% of the experimentally determined initial rates for mEDN, omEDN and the lower-activity chimeras. All double-reciprocal plots were constructed from appropriately corrected initial rates. All time points represent the average of triplicate samples. Calculations included the following approximations: the average molecular weight ($M_r$) of tRNA as $M_r$=28,100 (75–90 ribonucleotides/tRNA molecule×$M_r$=341/ribonucleotide), with $A_{260}$ of 1.0 corresponding to 40 ug of RNA (J. Sambrook et al., 1989, Molecular Cloning: a laboratory manual 2nd Ed., Cold Spring Harbor Laboratory, Cold Spring Harbor, N.Y.). Bestfits and correlation coefficients ($r^2$) were determined with the assistance of Cricket Graph software on-line at the National Institutes of Health.

Results

Figures 11A, 11C:
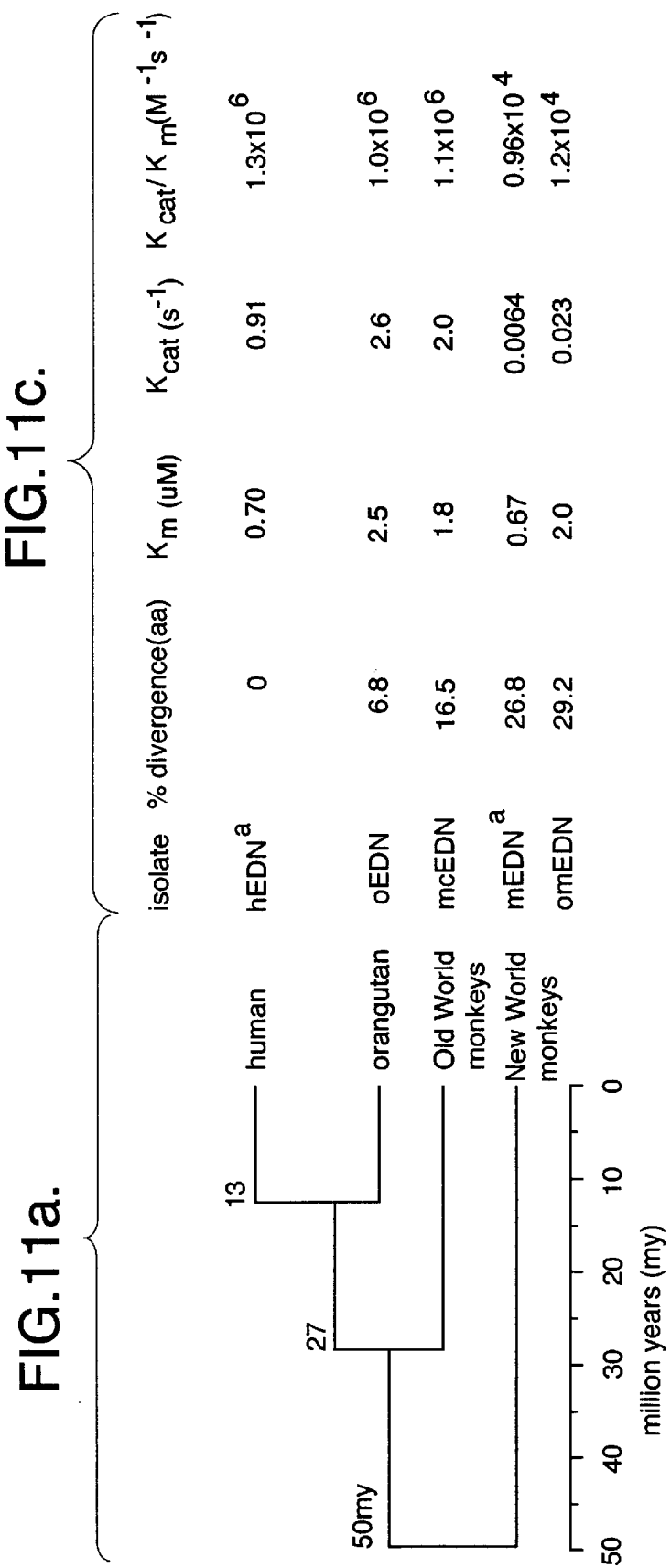
FIG. 11A shows estimated evolutionary distances between human and non-human primates (H. F. Rosenberg and K. D. Dyer, 1995, J. Biol. Chem., 270:21539–21544; H. f. Rosenberg, 1995, J. Biol. Chem., 270:7876–7881).
FIG. 11C shows characteristics of recombinant EDNs from sequences isolated from genomic DNA from the primates listed in FIG. 11B as well as from human (*H. sapiens*, hEDN) and another New World monkey (*S. oedipus*, mEDN). Percent amino acid divergence for all but omEDN were as reported in Rosenberg and Dyer (1995, J. Biol. Chem. 270:21539–21544). Values for $K_m$ ($\mu$M) and $k_{cat}$ ($s^{-1}$) were calculated from the data shown in FIG. 11B for oEDN, mcEDN and omEDN; those for hEDN and mEDN were taken from Rosenberg and Dyer, supra.
Figure 11B:
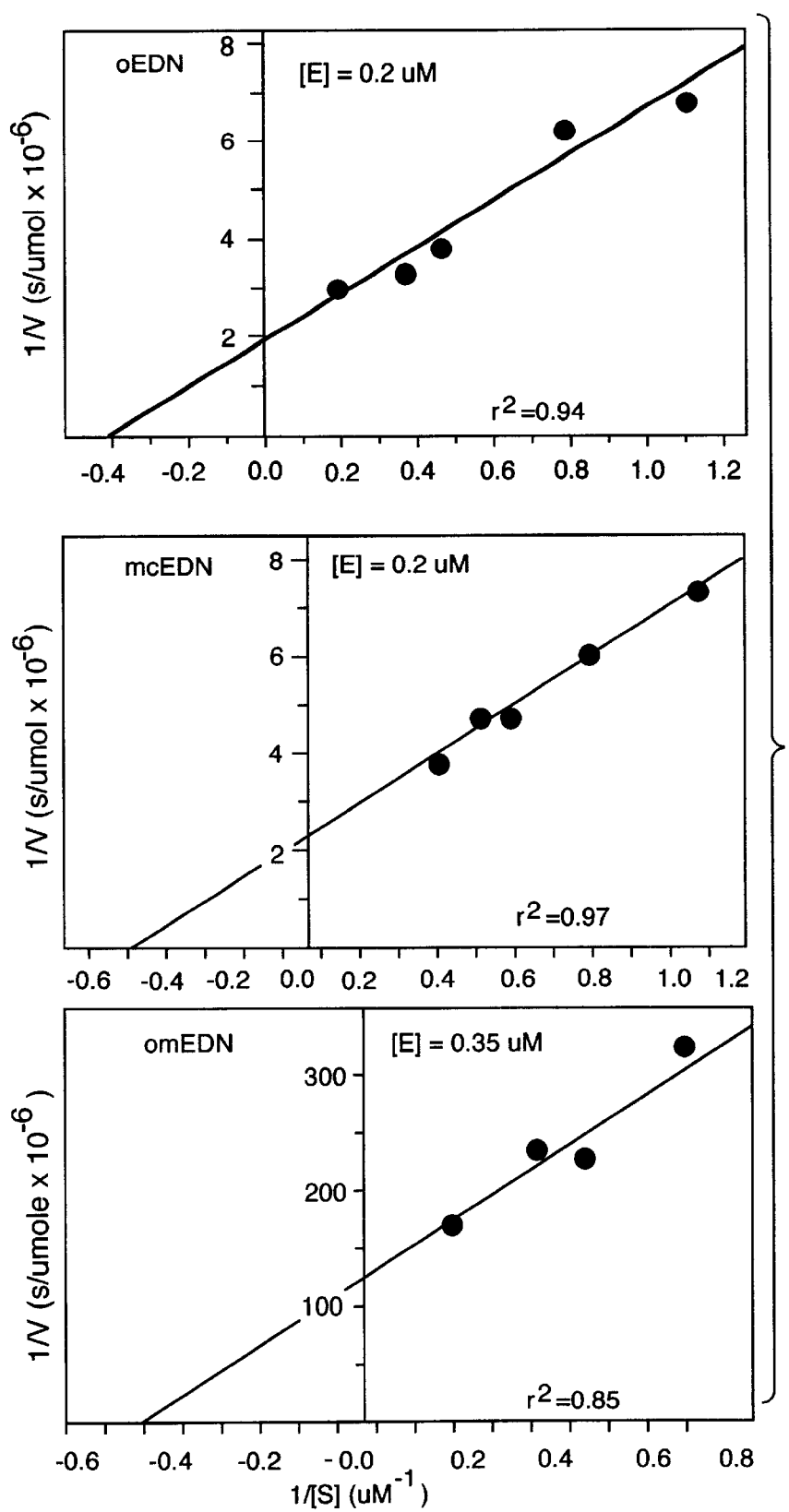
FIG. 11B shows ribonuclease activities (substrate versus initial rates of reaction) presented as double reciprocal plots. Recombinant EDNs were prepared from sequences isolated from orangutan (*P. pygmaeus*, oEDN), the Old World monkey, macaque (*M. fascicularis*. mcEDN) and the New World monkey, owl monkey (*A. trivigatus* omEDN) genomic DNA, with GenBank accession numbers U24104, U24099, and U88827, respectively.

Ribonuclease activity of primate EDNs: The estimated evolutionary distances between the human and non-human primate species discussed in this work are shown in FIG. 11A (H. F. Rosenberg and K. D. Dyer, 1995, J. Biol. Chem., 270:21539–21544; C. G. Sibley and J. E. Ahlquist, 1984, J. Mol. Evol., 20:2–15). The double reciprocal plots shown in FIG. 11B demonstrate the relationship between substrate concentration and ribonuclease activity for recombinant EDNs prepared from several non-human primate sequences: orangutan (Pongo pygmaeus, oEDN), the Old World monkey, macaque (*Macaca fascicularis*, mcEDN), and the New World monkey, owl monkey (*Aotus trivirgatus*, omEDN). The values for $K_m$ ($\mu$M), as determined from the x-intercepts, and $k_{cat}$ ($s^{-1}$), as determined from the y-intercepts of these plots, are tabulated in FIG. 11C and compared to those obtained previously for both human (*Homo sapiens*, hEDN) and New World monkey (*S. oedipus*, mEDN)-derived recombinant proteins (H. F. Rosenberg, and K. D. Dyer, 1995, J. Biol. Chem, 270:21539–21544).

Although the amino acid sequences of both oEDN and mcEDN differ significantly from that of hEDN (6.8% and 16.5% divergence, respectively), the catalytic constants and the calculated catalytic efficiency ($k_{cat}/K_m$) remain unchanged. The catalytic efficiencies of recombinant hEDN, oEDN, and mcEDN are all on the order of $10^6$ $M^{-1}$ $s^{-1}$. In contrast, the catalytic constants determined for the two EDNs isolated from New World monkeys (mEDN and omEDN) show significant reductions in $k_{cat}$, and thus reductions in overall catalytic efficiencies (~100-fold), with $k_{cat}/K_m$ calculated for each at 0.96×$10^4$ $M^{-1}$ $s^{-1}$ and 1.2×$10^4$ $M^{-1}$ $s^{-1}$, respectively.

Human (hEDN) and owl monkey (omEDN) sequence chimeras: An alignment of the predicted amino acid sequences of hEDN and omEDN is shown in FIG. 12A. The omEDN sequence retains the eight cysteines as well as the catalytic histidines and lysine that are characteristic of the RNase A gene family (J. J. Beintema et al., 1996, Academic Press, FL; H. F. Rosenberg and K. D. Dyer, 1996, Nucl. Acids Res., 18:3507–3513). Similarly, the omEDN sequence contains the CKXXNTF motif (amino acids 37–44 of SEQ ID NO:6) also found as invariant among these proteins (J. J. Beintema et al., 1996, Academic Press, FL; H. F. Rosenberg and K. D. Dyer, 1996, Nucl. Acids Res., 18:3507–3513; Protein Data Base, entry PDOC00118: October 1993 update). The calculated amino acid sequence divergence between hEDN and omEDN is 29.2% (see FIG.

11C). The two sequences were found to be identical within the two bracketed areas shown, permitting construction of chimeras A and B (FIG. 12B). The ribonucleolytic activities of both chimera A (first part hEDN followed by second and third parts omEDN) and chimera B (first and second parts hEDN followed by third part omEDN) were determined as "+", reflecting their similarity to the lower level of activity observed for omEDN (and mEDN).

These results suggest that a sequence element (or elements) present in the carboxy-terminus of hEDN is necessary for full catalytic activity. There are only two regions of significant divergence within this final segment of EDN sequence: the gap in omEDN in place of Arg 117 of hEDN, and the penultimate Thr-Thr in omEDN in place of Arg 132-Ile 133 of hEDN (see FIG. 11A). Interestingly, both oEDN and mcEDN are more closely related to hEDN at these sites; oEDN is identical to hEDN, and in mcEDN, a Val replaces Arg 117.

Carboxy-terminal chimeras: As shown in FIG. 13A, chimera C was created by exchanging the carboxy-terminal Arg-Ile-Ile (132–134) of hEDN with Thr-Thr-Ile from omEDN, and chimera D, by exchanging the Thr-Thr-Ile of hEDN for Arg-Ile-Ile. Double reciprocal plots of substrate concentration versus initial rates yielded the catalytic constants listed in FIG. 13B. Comparison of the values calculated for $k_{cat}/K_m$ for hEDN ($1.3\times10^6$ $M^{-1}$ $s^{-1}$) and chimera C ($16\times10^5$ $M^{-1}$ $s^{-1}$) demonstrates that the carboxy-termninal sequence exchange resulted in an ~8-fold reduction in catalytic activity. In contrast, $k_{cat}/K_m$ determined for chimera D ($1.3\times 10^4$ $M^{-1}$ $s^{-1}$) does not differ significantly from that determined for wild type omEDN. Taken together. these results indicate that the carboxy-terminal sequence Arg 132-Ile 133 is necessary to sustain the full catalytic activity of hEDN, but at the same time it has no effect on the relatively inactive omEDN.

Discussion

The ribonuclease activity of five evolutionary variants of EDN, representing one branch of the ribonuclease A gene family (J. J. Beintema et al., 1996, Academic Press, FL.), was compared. The EDN gene has an interesting structural and functional evolutionary history (H. F. Rosenberg, 1995, Nature Genetics, 10:219–223; H. F. Rosenberg and K. D. Dyer, 1995, J. Biol. Chem., 270:21539–21544). In particular, recombinant EDN derived from the New World monkey (S. oedipus) sequence had only a fraction of the ribonuclease activity demonstrated by its human ortholog despite the presence of structural and catalytic elements known to be crucial to this function (H. F. Rosenberg and K. D. Dyer, 1995, J. Biol. Chem, 270:21539–21544).

Recombinant EDNs derived from orangutan (oEDN) and macaque (mcEDN) sequences retained full catalytic efficiency against the tRNA substrate used in these experiments, while recombinant EDN derived from a second New World monkey, A. trivirgatus, (omEDN, 29.2% divergence from hEDN) was again ~100-fold less active. The relative ribonucleolytic activities of chimeras prepared from selected segments of hEDN and omEDN pointed to a carboxy-terminal segment as crucial to the elevated catalytic rate, and further analysis identified the penultimate amino acids in hEDN, Arg 132-Ile 133 as necessary (but notably, not sufficient) for enhanced activity.

It is not immediately clear why the Arg-Ile pair in this position should play such a crucial role in mediating enhanced catalytic activity. In the crystal structure of human EDN recently reported by Mosimann and colleagues (S. C. Mosimann et al., 1996, J. Mol. Biol., 260:540–552) Arg 132 and Ile 133 appear on the outer surface of the protein, within the sixth beta strand. They do not appear to interact directly with the active site residues (His 15, His 129, and Lys 38), nor are they included among the reported intermolecular contact points.

Beintema (J. J. Beintema, 1989, FEBS Letters, 254:1–4) predicted the importance of a cationic residue in this position, suggesting that it might form electrostatic contacts with the negatively charged phosphate group situated immediately 5' to the phosphodiester bond of the substrate undergoing ribonucleolytic cleavage. As such, Arg 132 would perform a function similar to that of Lys 66 in the $p^0$ subsite of bovine pancreatic ribonuclease (RNase A) (X. Pares et al., 1991, in Essays in Biochemistry, K. F. Tipton, ed., Portland Press, London, UK, pp. 89–103). Consistent with this hypothesis, exchanging the Arg 132-Ile 133 with Thr-Thr results in a significant reduction in the ribonucleolytic activity of recombinant hEDN. However, the reverse exchange-Arg 132-Ile 133 in place of the Thr-Thr-does nothing to enhance the relatively low catalytic activity of omEDN. indicating that Arg 132, while necessary, is not sufficient, and cannot act alone to augment the ribonucleolytic activity.

EDN is one of six human members of the RNase A family that have been characterized to date, and one of two ribonucleases present in large quantities in the human eosinophilic leukocyte. Other members of this family have been characterized as agents of host defense (C. J. F. Spry, 1988, Eosinophils. A comprehensive review and guide to the scientific and medical literature, Oxford University Press, Oxford, UK; S. J. Ackerman, 1993, Eosinophils. Biological and clinical aspects, CRC Press, Boca Raton, Fla., pp. 33–74) and of angiogenesis (R. Shapiro et al., 1986, Biochemistry, 25:3527–3532; D. K. St. Clair et al., 1987, Proc. Natl. Acad. Sci. USA, 84:8330–8334).

Example 5

Eosinophil Cationic Protein/RNase 3 is Another RNase A-family Ribonuclease With Direct Antiviral Activity This example provides a biochemical characterization of a novel formulation of recombinant human ECP (rhECP), and demonstrates that rhECP also has direct activity against extracellular forms of RSV. Interestingly, this antiviral activity is not shared with other RNase A-family ribonucleases. This specificity for EDN and ECP, along with the observation that EDN/ECP combinations did not enhance antiviral activity above that measured for EDN alone, suggests a possible ribonuclease-mediated mechanism of antiviral action.

Methods

Production of recombinant protein: Recombinant baculoviral vectors were constructed by inserting the full-length coding sequence of human ECP (Genbank Accession No. X15161, nucleotides 55 . 537) in-frame with a C-terminal Flag octapeptide (International Biotechnologies, Inc., New Haven, Conn.) into the Bam HI/Xba I sites of the pVL1393 transfer vector (Invitrogen, San Diego, Calif.). Three micrograms of recombinant vector and 0.5 μg of linear wild type baculovirus AcNPV (Pharmingen, San Diego, Calif.) were used to cotransfect Spodoptera frugiperda (Sf9) cells by the lipofectin method (Gibco BRL, Gaithersburg, Md.). Polyhedrin-deficient recombinant viruses were selected and cloned by standard plaque assay and the presence of the protein product was confirmed by immunoblotting with both the M2 monoclonal anti-FLAG antibody and polyclonal rabbit anti-ECP antiserum. Large scale production of rhECP was achieved by infecting 100 ml suspension cultures of Sf9 cells ($2 \times 10^6$/ml) with recombinant virions. Supernatants containing rhECP secreted from the infected cells were harvested 72–96 hours post-infection. Recombinant vectors encoding two additional RNase A-family ribonucleases, human EDN (rhEDN; Genbank Accession No. M24157) and human RNase k6 (rhRK6; Genbank Accession No. U64998) were prepared in a similar fashion and were used to transfect Sf9 cells, and supernatants containing secreted recombinant protein were likewise harvested at 72–96 h post-infection.

Protein purification: Supernatants harvested from 100 ml infected cultures were dialyzed (4° C.) against 50 mM tris pH 8.0+1 mM NaCl. Recombinant ECP was intially concentrated by heparin-sepharose column chromatography (Pharmacia Biotech, Piscataway, N.J.) and eluted via a salt-gradient (1 to 500 mM NaCl in 50 mM tris, pH 8.0). The fractions containing recombinant protein were concentrated (Centricon 10 concentrator, Amicon, Beverly Mass.) and subjected to size-fractionation (Superdex 200, Pharmacia Biotech), resulting in purified protein, with typical yields of 1 to 24 μg rhECP per ml infected Sf9 supernatant. Protein concentration was determined by BCA assay (Pierce, Rockford, Ill.) against bovine serum albumin standards. Recombinant proteins rhEDN and rhRK6 were purified in an analogous fashion.

Protein deglycosylation and Western blotting: Aliquots of purified rhECP were heat/detergent denatured prior to attempted deglycosylation with endoglycosidase H (endo H) or with peptide N-glycosidase F (PNGase F; New England Biolabs, Beverly, Mass.) as per manufacturer's instructions. Negative controls were treated identically, save for the addition of distilled water in place of enzyme. Western blots were performed as previously described (H. F. Rosenberg, 1995, J. Biol. Chem, 270:7876–7881; H. F. Rosenberg et al., 1995, J. Biol. Chem, 270:21539–21544); primary antibodies included a 1:200 dilution of M2 anti-Flag mAb and 1:300 dilution of rabbit polyclonal anti-ECP (H. F. Rosenberg et al. 1994, J. Leukoc. Biol., 56:502–506) with secondary antibodies including alkaline-phosphatase conjugated goat anti-mouse or anti-rabbit IgG, respectively (BioRad, Richmond, Calif.), and NBT and BCIP (BioRad) as developing reagents. Native ECP was detected in a 1% triton-extract from peripheral blood leukocytes, also as previously described (H. L. Tiffany et al., 1995, J. Leukoc. Biol., 58:49–54).

Ribonuclease assay: The ribonuclease assay was as described previously in detail (H. F. Rosenberg, 1995, J. Biol. Chem, 270:7876–7881; H. F. Rosenberg et al., 1995, J. Biol. Chem, 270:21539–21544; H. F. Rosenberg et al., 1997, Nucl. Acids Res., 25:3532–3536). Briefly, the concentration of perchloric acid soluble ribonucleotides generated from acid-precipitable yeast tRNA (Sigma, St. Louis, Mo.) in 40 mM sodium phosphate, pH 7.5 by a given quantity of ribonuclease (RNase A, rhEDN, rhECP, or rhRK6) was measured spectrophotometrically at 260 nm. Each point shown on the double reciprocal plot (FIG. 17A) and on the inhibition plot (FIG. 17B) represents an intial rate of reaction determined at given enzyme and substrate concentrations from at least four sequential time points, each measured in triplicate. Ribonuclease inhibitor (RI; 40 U/μl) was purchased from Boehringer Mannheim (Indianapolis, Ind.). The assays measuring ribonuclease activity in Tables 2 and 3 were performed using 10 μl of remaining viral stock to which ribonuclease has been added to the final concentration indicated (see antiviral assay below) and 10 82 l of 4 mg/ml yeast tRNA in an 0.8 ml reaction volume. Initial rates were determined from two sequential time points, each measured in triplicate.

Antiviral activity assay: Direct antiviral activity of rhECP and other ribonucleases was performed by the quantitative shell vial amplification technique described in Example 1, supra. Recombinant proteins (rhECP, rhEDN, rhRK6), native proteins (RNase A, Onconase) or equivalent volumes of buffer control (50 mM tris pH 8.0+150 mM NaCl) were added to viral stocks of RSV prepared as described in Example 2, supra. After 2 h gentle rotation at room temperature, the treated viral stocks (200 μl) were used to infect target HEp-2 cells (human pulmonary epithelial/laryngeal carcinoma cells) present in confluent monolayers ($3-4 \times 10^5$ cells/monolayer) on coverslips in one dram shell vials (Viromed, Minneapolis, Minn.). Inoculated shell vials were centrifuged at 700×g at 22° C. for 1 h to amplify the infection. One ml maintenance medium (Eagle's Minimal Essential Medium (EMEM)+10% heat-inactivated fetal bovine serum+2 mM glutamine) was added, and the shell vials were incubated at 37° C., 5% $CO_2$ for 16 hrs, conditions permitting only a single round of RSV infection. After incubation. the monolayers were washed and fixed with cold acetone. Immunofluorescence staining for primary RSV-infected cells was performed with mouse anti-RSV blend FITC-labelled monoclonal antibody (Chemicon International, Temecula, Calif.). Each coverslip was observed under fluorescence microscopy and the number of fluorescent cells per coverslip determined; each condition was assayed in triplicate. Data are expressed as infectious units/ml+/–standard deviation (sd). An infectious unit is defined as the component within the viral suspension that results in the detectable infection of a single cell in the confluent monolayer. Infectious units are linear with respect to viral dilution over the range utilized in these experiments ($r^2=0.987$) and have been shown to correlate with plaque-forming units over a wide range of viral concentrations. No toxicity to the HEp-2 monolayer was observed at any of the ribonuclease concentrations indicated.

Results

Electrophoretic mobility and glycosylation of recombinant human eosinophil cationic protein (rhECP): The electrophoretic mobility of rhECP prepared using the baculovirus expression system is shown in FIG. 16A. RhECP migrates as a single species of molecular mass of 22 kDa, similar to the most extensively glycosylated form of the native immunoreactive protein (FIG. 16B). Upon treatment with PNGase F (but not endo H), rhECP is deglycosylated to a single species of molecular mass ~18 kDa, suggesting substitution with complex carbohydrates at one or more of its three potential N-glycosylation sites. The activity of endo H was confirmed by digestion of immature forms of the recombinant protein identified in lysates of infected Sf9 cells.

Figure 17A:
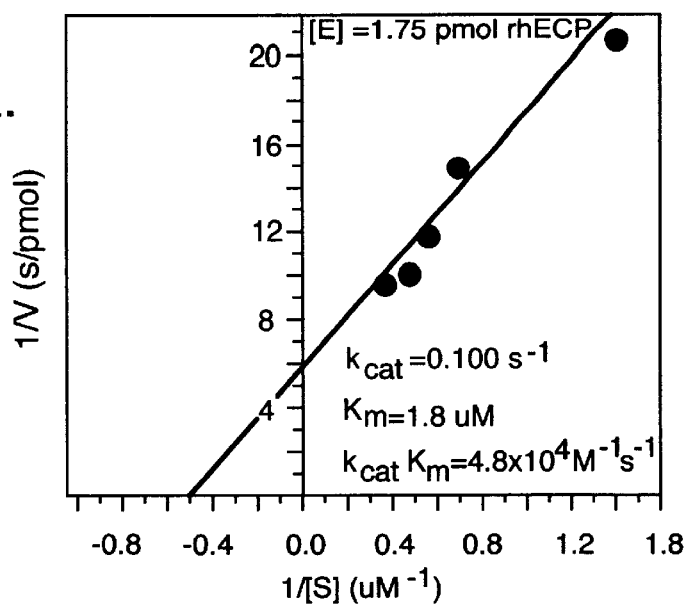
FIG. 17A shows a double reciprocal (Lineweaver-Burk) plots depicting rates of ribonuclease activity (pmol soluble ribonucleotides generated per second) at varying substrate concentrations (uM yeast tRNA) determined for baculovirus-derived rhECP. Catalytic constants $K_m$ and $k_{cat}$ were determined from x and y intercepts as previously described (12); $r^2=0.97$.

Ribonuclease activity of rhECP: Shown in FIG. 17A is a double reciprocal (Lineweaver-Burk) plot comprised of initial rates of reaction (1/V) in which acid-soluble ribonucleotides generated per unit time (pmol/s) at the given enzyme concentration [E] was measured at varying substrate concentrations (1/[S]). The catalytic constants for baculovirus-derived rhECP include: $k_{cat}=0.100$ s$^{-1}$, $K_m=1.9$ uM, and the catalytic efficiency $k_{cat}/K_m=4.9 \times 10^4$ M$^{-1}$ s$^{-1}$. Surprisingly, the values obtained for $k_{cat}$, and thus for catalytic efficiency $k_{cat}/K_m$, for the baculovirus-derived form of rhECP differed dramatically from those obtained previously for rhECP prepared in bacteria ($k_{cat}$=0.0024 s$^{-1}$, $K_m$=4.1 uM, $k_{cat}/K_m$= 0.59×10$^3$ M$^{-1}$ s$^{-1}$).

Figure 17B:
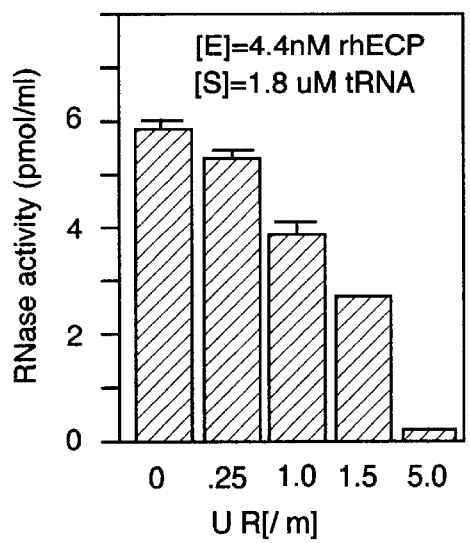
FIG. 17B shows ribonuclease activity (pmol/min) at single enzyme/substrate concentrations in the presence of increasing concentrations of placental ribonuclease inhibitor (RI).
Figure 19B:
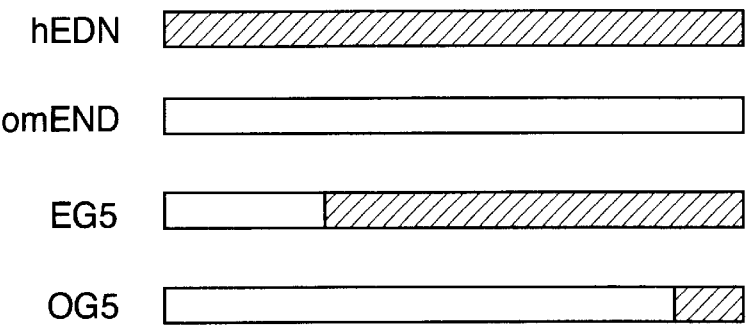
FIG. 19B shows segment maps of chimeras EG5 and OR5.

Ribonuclease inhibitor (RI) is a cytosolic protein with high affinity for many RNase A-family ribonucleases, with particularly strong interactions reported between RI and RNase A and RI and EDN/RNase 2. Shown in FIG. 17B is a bar graph demonstrating initial rates of reaction fixed enzyme (rhECP) and substrate (tRNA) concentrations in the presence of increasing concentrations of a commerical preparation of placental ribonuclease inhibitor (RI). These results demonstrate that rhECP is sensitive to the inhibitory effects of RI.

Antiviral activity of rhECP: In Tables 2 and 3, the antiviral activities of rhECP and rhEDN, separately and in combinations, are presented. Despite the fact that ECP is more cationic, and generally more toxic than EDN, rhECP is nearly ten-fold less effective than rhEDN in reducing the infectivity of RSV-B on a molar basis, with 500 nM rhECP reducing infectivity ~6-fold, as compared to the 54-fold observed with 500 nM rhEDN. The antiviral activity of rhECP is reduced in the presence of RI (Table 2); the concentration of RI used (0.8 U/pmol enzyme) was relatively low, enough so that a complete inhibition of rhECP would not be expected. Interestingly, the combinations of rhECP (62.5 to 500 nM) with 500 nM rhEDN displayed no synergistic nor any additive antiviral effect (Table 3).

Table 2 shows dose-dependent reduction in RSV-B infectivity (inf units/ml) in response to rhECP alone. RSV-B infectivity was determined by quantitative shell vial assay as described Example 2. Values shown are averages of duplicate samples +/−standard deviation (sd). Ribonuclease activity (pmol acid-soluble ribonucleotides generated per minute (pmol/min) was determined using ten microliter aliquots of viral supernatant to which rhECP was added to the concentrations indicated, with time points assayed in triplicate.

TABLE 2

| [rhECP] | infectious units/ml | RNase activity (pmol/m) | fold reduction viral titer |
|---|---|---|---|
| 0 | 4183 +/− 180 | 0.8 | — |
| 62.5 nM | 4338 +/− 166 | 0.8 | — |
| 125 nM | 3145 +/− 106* | 1.2 | 1.3 |
| 250 nM | 1983 +/− 103** | 1.9 | 2.1 |
| 500 nM | 660 +/− 28** | 3.6 | 6.3 |
| 500 nM 400U RI[a] | 1687 +/− 120 | 2.0 | 2.5 |

[a]Abbreviation RI refers to placental ribonuclease inhibitor. Values shown differ significantly from baseline ([rhECP] = 0) at the *p < 0.05 and **p < 0.01 levels.

Table 3 shows reduction in RSV-B infectivity (infectious units/ml) in response to rhEDN alone and in combinations with rhECP. Measurements of both infectivity and ribonuclease activity (pmol/min) are as described for Table 2. Values shown differ significantly from baseline ([rhEDN]= [rhECP]=0) at the (**) p<0.01 level.

TABLE 3

| [rhEDN] | [rhECP] | infectious units/ml | RNase activity (pmol/m) | fold reduction viral titer |
|---|---|---|---|---|
| 0 nM | 0 nM | 4183 +/− 180 | 0.8 | — |
| 500 nM | 0 nM | 78 +/− 25** | 201 | 54 |
| 500 nM | 62.5 nM | 100 +/− 28** | 185 | 42 |

TABLE 3-continued

| [rhEDN] | [rhECP] | infectious units/ml | RNase activity (pmol/m) | fold reduction viral titer |
|---|---|---|---|---|
| 500 nM | 125 nM | 125 +/− 0** | 206 | 33 |
| 500 nM | 250 nM | 138 +/− 11** | 217 | 30 |
| 500 nM | 500 nM | 105 +/− 21** | 229 | 39 |

Table 4 shows dose-dependent reduction in RSV-B infectivity (inf units/ml; triplicates+/−sd) in response to rhRNase k6, RNase A and Onconase. Measurements of RSV-B infectivity and ribonuclease assays are as described for Table 2.

TABLE 4

| | infectious units/ml | RNase activity (pmol/m) |
|---|---|---|
| [rhRNase k6] | | |
| 0 nM | 2452 +/− 108 | 0.7 |
| 150 nM | 2405 +/− 359 | 21.2 |
| 300 nM | 2562 +/− 115 | 59.2 |
| 500 nM | 2500 +/− 133 | 69.5 |
| [RNase A] | | |
| 0 nM | 4360 +/− 252 | 0.78 |
| 400 nM | 4020 +/− 342 | 1450 |
| 4000 nM | 4380 +/− 284 | 17,840 |
| [Onconase] | | |
| 0 nM | 3273 +/− 240 | 0.62 |
| 40 nM | 3203 +/− 240 | 0.70 |
| 400 nM | 2995 +/− 131 | 0.68 |
| 4000 nM | 3060 +/− 143 | 1.0 |

While the data in Tables 2 and 3 would suggest that antiviral activity correlates with increased ribonuclease activity (3.6 pmol/m from 500 nM rhECP vs. 201 pmol/m from 500 nM rhEDN), the results presented in Example 2 as well as the data presented in Table 4 indicate that ribonuclease activity is essential but not sufficient to explain EDN's and ECP's overall effectiveness. RNase A (bovine RNase 1), the prototype of this family, is a potent ribonuclease with no apparent antiviral activity even at concentrations as high as 4000 nM. Onconase, an amphibian ribonuclease that has low catalytic activity yet has antitumor and antiviral activity against intracellular forms of HIV (S. K. Saxena et al., 1996, J. Biol. Chem., 271:20783–20788) also has no direct antiviral activity against RSV-B in this assay. Human RNase k6, a ribonuclease with moderate catalytic activity that is closely related to EDN and ECP (50% amino acid sequence similarity (H. F. Rosenberg et al., 1996, Nucl. Acids Res., 24:3507–3513) likewise promotes no loss of RSV-B infectivity.

Discussion

Although ribonuclease activity appears to be crucial to the antiviral activity promoted by both rhECP and rhEDN, other members of the RNase A ribonuclease family, including the closely-related human RNase k6, have no direct antiviral activity in this assay. Taken together, these results suggest that EDN and ECP, the two most rapidly evolving coding sequences known among primates, may be responding to constraints promoting increased antiviral activity specifically within this lineage.

The non-glycosylated form of rhECP prepared as a recombinant secretory protein in bacteria was both toxic and enzymatically active with a catalytic efficiency ($K_m/k_{cat}$)

measured at $0.59 \times 10^3$ $M^{-1}$ $s^{-1}$. The rhECP prepared as a baculovirus-derived secretory protein is N-glycosylated, with electrophoretic mobility similar to that of the most extensively glycosylated form of the native protein (H. L. Tiffany et al., 1995, J. Leukoc. Biol., 58:49–54). The ribonucleolytic activity of this glycosylated form of rhECP is nearly 100-fold greater than that prepared in bacteria ($K_m/k_{cat}=4.9\times10^4$ $M^{-1}$ $s^{-1}$). This finding itself is not unusual, as there are a number of proteins (both recombinant and native) in which biologic activity has been shown to be enhanced by N-glycosylation. ECP has three potential sites for N-linked glycosylation; the observation that rhECP migrates as a single band by polyacrylamide gel electrophoresis suggests a homogeneous pattern of glycosylation, but this has not been established with certainty. Similarly, the molecular basis for enhanced ribonuclease activity has not yet been clarified, but the presence of negatively-charged glycosyl groups may alter the pattern of intracellular protein folding, and will also effectively reduce the net positive charge characteristic of the mature ECP polypeptide (calculated pI=11.8) which may in turn alter the way in which rhECP interacts with its negatively-charged polyribonucleotide substrate.

The interaction of rhECP with placental ribonuclease inhibitor (RI), a ubiquitous cytoplasmic protein with high affinity ($K_i$ s from ~$10^{-16}$) for several of the RNase A family ribonucleases has also been examined (J. Hofsteenge, 1997, in Ribonucleases: Structures and Functions (G. D' Alessio and J. F. Riordan. eds) pp. 621–658, Academic Press, San Diego, Calif.). Although the biologic role of RI has not been clarified, RI may serve to protect intracellular RNA from degradation by secretory ribonucleases such as ECP that found their way into the cell cytoplasm.

The direct antiviral activity exhibited by rhECP and rhEDN appears to be a unique feature of the eosinophil ribonucleases. The prototype of this family, RNase A, is a potent ribonuclease with no direct antiviral activity in this assay, and Onconase, an amphibian ribonuclease that has been shown to mediate antiviral activity against intracellular forms of HIV (S. K. Saxena et al., 1996, J. Biol. Chem., 271:20783–20788) was similarly ineffective. Perhaps most intriguing was the observation that human RNase k6, a moderately powerful ribonuclease with 50% amino acid sequence similarity to EDN/ECP, prepared in an identical fashion from supernatants from baculovirus-infected Sf9 cells, also proved to be unable to reduce infectivity of RSV-B.

As all of these ribonucleases are capable of generalized RNA degradation, it would seem as though the eosinophil ribonucleases must possess some unique, specific features apart from ribonuclease activity that permit them to penetrate the viral capsid to gain access to the viral RNA genome. The results of the EDN/ECP combination experiments suggest how this might occur. EDN/ECP combinations resulted in no synergy nor any observable additivity. These results suggested that EDN might be binding to a specific, saturable target molecule, most likely on the viral surface. While ECP can promote some antiviral activity on its own, its reduced antiviral toxicity may be due to lower affinity for this specific target. When presented in the combinations shown, the entire antiviral effect observed is that promoted by rhEDN, the higher-affinity ribonuclease. The ribonucleolytically inactivated form of rhEDN, rhEDNdK[38], shown to have no activity as an antiviral agent, is capable of blocking the antiviral activity of ribonucleolytically active rhEDN when presented in equimolar amounts. While these results provide evidence in support of a specific, saturable interaction between rhEDN and an as yet unidentified target molecule, the nature of this entity and the specifics of the proposed interaction both remain to be clarified.

Example 6

Evolution of Antiviral Activity in a Primate Ribonuclease Gene Family Evidence for a Specific Interaction Between Eosinophil-Derived Neurotoxin (EDN/Rnase 2) and Respiratory Syncytial Virus This example demonstrates the existence of a unique structural feature characteristic of EDN, by demonstrating that the interaction between EDN and extracellular virions of RSV is both specific and saturable. It also shows that acquisition of antiviral activity parallels the evolutionary development of the primate EDN gene lineage, and, through the construction of human/owl monkey EDN chimeras, identifies an amino terminal segment of human EDN that contains one or more of these specific elements.

Materials and Methods

For the experiments described in Tables 5 and 9, recombinant proteins were prepared from cDNAs encoding EDNs of human (*Homo sapiens*; Genbank M24157), orangutan (*Pongo pygmaeus*; U24104), macaque (*Macaca fascicularis*, U24096), tamarin (*Saguinus oedipus*, U24099) and owl monkey (*Aotus trivirgatus*; U88827) in the pFCTS bacterial expression vector as described (H. F. Rosenberg and K. D. Dyer, 1995, J. Biol. Chem., 270:21539–21544). With this system, recombinant ribonucleases are directed to the bacterial periplasm and can be isolated in enzymatically active form. Culture, induction, and isolation of recombinant protein via M2 agarose chromatography was as described previously (H. F. Rosenberg and K. D. Dyer, supra) save for changes in the induction and harvest conditions. Limited induction with a reduced concentration of IPTG (1 µM), followed by bacterial freeze-thaw and sonication, has permitted quantitative harvest of ribonucleolytically-active recombinant protein, avoiding the losses necessitated by gentle periplasmic stripping (H. F. Rosenberg, 1998, Biotechniques, 24(2):188–192). Human/owl monkey EDN chimeras were prepared by overlap PCR mutagenesis as described (H. F. Rosenberg and K. D. Dyer, 1997, Nucleic Acids Res., 25:3532–3536) and prepared as recombinant proteins via the pFCTS expression vector.

Preparation of recombinant ribonucleases via baculovirus expression: For the experiments described in Tables 7 and 8, recombinant human RNase k6 (H. F. Rosenberg and K. D. Dyer, 1996, Nucleic Acids Res., 24:3507–3513, Genbank Accession No. U64998), human EDN, and human EDNdK[38] (ribonucleolytically-inactived EDN via conversion of the catalytic residue K[38] to R) were prepared from supernatants of Sf9 cells infected with recombinant baculoviral constructs. The recombinant baculoviral vectors included the full-length coding sequences of each of these three ribonucleases inserted in-frame with the carboxy-terminal FLAG octapeptide (analogous to the pFCTS expression constructs) into the Bam HI/Xba I sites of the pVL 1393 transfer vector (Invitrogen, San Diego, Calif.). Three micrograms of recombinant vector and 0.5 µg of linear wild type baculovirus AcNPV (Pharmingen, San Diego, Calif.) were used to cotransfect *Spodoptera frugiperda* (Sf9) insect cells by the lipofectin method (Gibco BRL, Gaithersburg, Md.). Polyhedrin-deficient recombinant viruses were selected and cloned by standard plaque assay, and the protein product was confirmed by immunoblotting with the M2 monoclonal anti-FLAG antibody. Large scale production of each ribonuclease was achieved by infecting 100 ml suspension cultures of Sf9 cells (2×10⁶/ml) with recombinant virions. Supernatants containing each ribonuclease were harvested at 96 h post-infection, at >60% cell lysis, and frozen at −80° C. prior to use. Defrosted supernatants (100–200 ml) were dialyzed overnight at 4° C. against 20 volumes of 50 mM tris, pH 8.0+1 mM NaCl. Recombinant ribonucleases were initially concentrated by Heparin-Sepharose FPLC chromatography and eluted via a salt gradient (1 mM to 500 mM NaCl). Fractions containing recombinant protein were concentrated (Centricon 10, Amicon, Beverly, Mass.) and subjected to size fractionation (Superdex G-75, Pharmacia Biotech) in a 50 mM tris+150 mM NaCl mobile phase, resulting in purified protein by gel electrophoretic analysis. Protein concentration was determined by BCA assay (Pierce, Rockford, Ill.) against bovine serum albumin standards.

Determination of viral infectivity: The antiviral activity of each recombinant ribonuclease versus extracellular virions of respiratory syncytial virus (RSV) group B was determined as described above. Briefly, recombinant protein at the final concentrations indicated (or buffer control) was added directly to suspensions containing virions (2 to 5×10³ infectious units/ml) in culture medium (Iscove's Modified Dulbecco's Medium+10% heat-inactivated fetal calf serum+2 mM glutamine), and incubated together with gentle rotation at room temperature. After a 2h incubation, 200 μl of the suspension was used to infect target cells (human respiratory epithelial HEp-2) present in confluent monolayers (3–4×10⁵ cells/monolayer) on coverslips within one-dram shell vial (Viromed, Minneapolis, Minn.). After spin amplification (70033 g at 22° C.) and 16 h incubation (37° C., 5% $CO_2$), the primary infected cells are identified by immunofluorescent staining (mouse anti-RSV blend, FITC labelled, Chemicon International, Temencula, Calif.). Data are presented as infectious units+/−standard deviation. The infectious unit is defined as the active component of the viral suspension that results in the detectable infection of a single cell within the HEp-2 monolayer. In addition, there exists a linear relationship between infectious units detected by this method and viral dilution (r2=0.99; x), and infectious units correspond to plaque-forming units generated by the more traditional plaque forming assay over the range of concentrations utilized in these experiments. No toxicity to the HEp-2 monolayer was observed at any of the ribonuclease concentrations indicated. In the specific blocking assay (Table 7), rhEDN was added after either rhEDNdK "or rhRNase k6 in the combinations as indicated.

Ribonuclease assay: The ribonuclease assay has been described above in detail. Briefly, the concentration of perchloric acid soluble ribonucleotides generated from acid-insoluble yeast tRNA (Sigma, St. Louis, Mo.) in a 40 mM sodium phosphate, pH 7.5 buffer by a given quantity of ribonuclease was measured spectrophotometrically at 260 nm, with the conversion to pmol tRNA. In the experiments described here, 10 μl of viral suspension to which recombinant ribonuclease had been added (final concentration 100 nM) was included in 0.8 ml reaction volume with 10 μl 4 mg/ml yeast tRNA. Presented here (Tables 5, 7, and 9) are initial rates calculated from four sequential time points, each assayed in triplicate.

Evolutionary analysis: Analysis of the molecular evolution of primate ribonucleases (FIGS. 18A–C, Table 6) was based on several previous studies (H. F. Rosenberg et al., 1995, Nature Genetics, 10:219–223; H. F. Rosenberg and K. D. Dyer, 1995, J. Biol. Chem., 270:21539–21544; J. Zhang et al., 1998, Proc. Natl. Acad. Sci. USA, 95:3708–3713). Values for synonymous and non-synonymous nucleotide substitution were calculated by the method described by Nei and Gojobori (M. Nei and T. Gojobori, 1986, Mol. Biol. Evol., 3:418–426). Values for nonsynonymous ($K_a$) and synonymous ($K_s$) substitution are calculated by the equations $K_a = N_d/N$ and $K_s = S_d/S$, respectively, where N and S are the probabilities that any single nucleotide change in a given coding sequence will be either non-silent (N) or silent (S) multiplied by the total number of nucleotides. $N_d$ and $S_d$ are determined via direct comparison of the sequences to one another, with each nucleotide sequence change scored appropriately. The data were also analyzed using the method described by Li (W.-H. Li et al., 1985, Mol. Biol. Evol., 2:150–174; W.-H Li, 1993, J. Mol. Evol., 36:96–99), which yielded analogous results. The sequence of the ancestral gene inferred by maximum parsimony methods (W.-H. Li and D. Graur, 1991, Fundamentals of Molecular Evolution., Sinauer Associates, Inc., Sunderland, Mass.) included 263 informative sites of a total 402 nucleotides. The amino acid sequence encoded by this ancestral sequence is as follows (with X denoting a codon including a non-informative site):

KPPQFTWAQWFXIQHIXXTPXXCTNAM-
RXINXYQXRCKNQNTFLXTTFADVVN-
VCGNXNXTCPRXXXLNNCHXSGVQV-
PLXXCNLXXXGPXXISNCXYXXTXANMF
YVVACDNRDXRRDPPQYPVVPVHLDTII (SEQ ID NO:11).

Results

Evolution of primate ribonuclease genes: The genes encoding the two eosinophil ribonucleases, EDN and ECP, are incorporating non-silent mutations at rates exceeding all other functional coding sequences studied among primates (H. F. Rosenberg et al., 1995, Nature Genetics, 10:219–223). Zhang and colleagues have provided evidence for Darwinian selection at the molecular level in this ribonuclease lineage (J. Zhang et al., 1998, Proc. Natl. Acad. Sci. USA, 95:3708–3713). The dendrogram in FIG. 18A and the divergence calculations in FIG. 18B depict the relationships among the primate EDN orthologs included in the present study. In FIG. 18C, the catalytic coefficients ($k_{cat}/K_m$) derived from double-reciprocal plots for each protein in recombinant form are listed. Acquisition of enhanced ribonuclease activity parallels the split between the Old World (macaque, african green monkey) and the New World monkeys (tamarin, owl monkey); the enhanced ribonuclease activity is maintained through the higher primate lineages.

Evolution of antiviral activity: A comparison of the antiviral activities of the various primate orthologs of human EDN is shown in Table 5. Human, orangutan, and macaque EDNs are equally effective against extracellular virions of RSV in suspension, with a 12–14 fold reduction in infectious units/ml observed in response to 100 nM recombinant protein in each case. As anticipated from their catalytic coefficients (FIG. 18C), the ribonuclease activities measured in the viral suspensions to which 100 nM recombinant EDN had been added were indistinguishable from one another. In contrast, neither of the two New World monkey ribonucleases, tamarin EDN and owl monkey EDN, displayed any antiviral activity in this assay. These amino acid sequences of these EDNs differ from human EDN by 27% and 29%, respectively, and they are not as ribonucleolytically active as the EDNs from higher primates.

Table 5 shows antiviral activity of primate orthologs of EDN. Sequences orthologous to human EDN were isolated from species indicated: genus/species designations include

*Pongo pygmaeus* (orangutan), *Macaca fascicularis* (macaque), *Saguinus oedipus* (tamarin), and *Aotus trivirgatus* (owl monkey). Antiviral activity was measured via the quantitative shell vial assay. Double asterisk (**) indicates that value differs significantly from baseline (0 nM) at the p<0.01 level. Ribonuclease activity was measured as generation of acid soluble ribonucleotides from acid insoluble tRNA substrate. Baseline ribonuclease activity measured in the absence of added EDN is 0.6 pmol/m.

TABLE 5

| Ortholog | Concentration (nM) | Infectious Units/ml +/− sd | RNase activity (pmol/m) |
|---|---|---|---|
| human EDN | 0 | 3220 +/− 208 | 35 |
|  | 25 | 2432 +/− 93 |  |
|  | 50 | 500 +/− 58** |  |
|  | 100 | 258 +/− 30** |  |
| orangutan EDN | 0 | 3768 +/− 88 | 30 |
|  | 25 | 2823 +/− 235 |  |
|  | 50 | 603 +/− 93** |  |
|  | 100 | 260 +/− 91** |  |
| macaque EDN | 0 | 3900 +/− 219 | 28 |
|  | 25 | 3268 +/− 214 |  |
|  | 50 | 583 +/− 26** |  |
|  | 100 | 302 +/− 60** |  |
| tamarin EDN | 0 | 3008 +/− 78 | 1.8 |
|  | 25 | 3015 +/− 184 |  |
|  | 50 | 3128 +/− 68 |  |
|  | 100 | 2951 +/− 63 |  |
| owl monkey EDN | 0 | 3122 +/− 87 | 2.7 |
|  | 25 | 3093 +/− 86 |  |
|  | 50 | 3078 +/− 138 |  |
|  | 100 | 3122 +/− 106 |  |

Table 6 present the rates of nonsynonymous ($K_a$) and synonymous substitution ($K_s$), respectively, for four World monkey/New World monkey EDN pairs. Each Old World monkey sequence was compared to an ancestral nucleotide sequence inferred to be present at the time of species divergence by maximum parsimony methods; the sequence is analogous (but not identical to) that of "node a" defined by Zhang and colleagues (J. Zhang et al., 1998, Proc. Natl. Acad. Sci. USA, 95:3708–3713). This type of analysis proceeds under two simplifying assumptions: (1) that synonymous, or silent substitution proceeds without specific constraints, and (2) that nonsynonymous, or non-silent substitution can be observed only when response to evolutionary constraints can be reconciled with the need to maintain structural integrity (positive selection). A $K_a/K_s$ greater than 1.0, or, the rate of nonsynonymous substitution exceeding the rate of synonymous substitution, has been accepted as an indication of positive selection, although there are very few examples of this phenomenon (J. Zhang et al., supra; M. Long and C. H. Langley, 1993, Science, 260:91–95; T. Ohta, 1994, Genetics, 138:1331–1337; D. J. Begun, 1997, Genetics, 145:375–382; M. Goodman et al., 1975, Nature, 253:603–608). While not exceeding unity, the $K_a/K_s$ ratios determined for the EDN pairs were relatively high, ranging from 0.68 to 0.82, with the ratios including the ancestral sequence somewhat lower. However, similar ratios were calculated for a series of Old World/New World monkey pairs encoding RNase 6, an RNase A-family ribonuclease that has displayed a more conservative rate of sequence divergence during primate evolution (M. S. Deming et al., 1998, Genome Research, 8(6):599–607).

Table 6 shows evolutionary analysis of New World and Old World monkey EDNs. Ratios of synonymous substitution per synonymous site ($K_s$) and nonsynonymous substitutions per nonsynonymous site ($K_a$) were calculated using the MEGA (Molecular Evolutionary Genetics Analysis) Program (Kumar, S. et al., 1993, *MEGA: Molecular Evolutionary Genetics Analysis*, version 1.01, The Pennsylvania State University, University Park, Pa.) and the DIVERGE algorithm (W.-H. Li et al., 1985, Mol. Biol. Evol. 2:150–174; W.-H. Li, 1993, J. Mol. Evol. 36:96–99) of the Wisconsin Genetics Computer Group program on-line at the National Institutes of Health. Analysis of the coding sequences did not include amino-terminal signal sequences. The sequence of the ancestral sequence inferred by maximum parsimony is provided in the Methods section above.

TABLE 6

| Coding sequence pairs | $K_a$ (substitutions/site) | $K_s$ (substitutions/site) | $K_a/K_s$ |
|---|---|---|---|
| EDN (RNase 2) New World/Old World |  |  |  |
| tamarin/macaque | 0.20 +/− 0.05 | 0.30 +/− 0.09 | 0.68 |
| tamarin/afr grn monkey | 0.20 +/− 0.05 | 0.27 +/− 0.08 | 0.74 |
| owl monkey/macaque | 0.22 +/− 0.05 | 0.29 +/− 0.09 | 0.74 |
| owl monkey/afr grn monkey | 0.21 +/− 0.09 | 0.26 +/− 0.08 | 0.82 |
| EDN (RNase 2) ancestral/Old World |  |  |  |
| ancestral/macaque | 0.078 +/− 0.03 | 0.14 +/− 0.05 | 0.56 |
| ancestral/afr grn monkey | 0.073 +/− 0.03 | 0.14 +/− 0.0 | 0.52 |
| EDN (RNase 2) New World/ancestral |  |  |  |
| tamarin/ancestral | 0.029 +/− 0.02 | 0.059 +/− 0.03 | 0.49 |
| owl monkey/ancestral | 0.041 +/− 0.02 | 0.071 +/− 0.04 | 0.58 |
| RNase k6 New World/Old World |  |  |  |
| tamarin/rhesus monkey k6 | 0.045 +/− 0.021 | 0.096 +/− 0.033 | 0.47 |
| tamarin/afr grn monkey k6 | 0.056 +/− 0.024 | 0.123 +/− 0.037 | 0.45 |
| owl monkey/rhesus monkey k6 | 0.046 +/− 0.019 | 0.062 +/− 0.025 | 0.74 |
| owl monkey/afr grn monkey k6 | 0.048 +/− 0.021 | 0.089 +/− 0.030 | 0.54 |
| squirrel monkey/rhesus monkey k6 | 0.077 +/− 0.022 | 0.095 +/− 0.054 | 0.82 |
| squirrel monkey/afr grn monkey k6 | 0.080 +/− 0.024 | 0.122 +/− 0.056 | 0.65 |

Antiviral activity of other RNase A family ribonucleases: As shown in the preceding Examples, other RNase A-family ribonucleases have no antiviral activity against extracellular virions of RSV in this assay (J. B. Domachowske et al., 1998, J. Infect. Dis., 177:1458–1464; J. B. Domachowske et al., 1998, Nucleic Acids Res. In press.), including RNase A, human RNase k6, and onconase. Table 7 extends this list to include bovine seminal ribonuclease (BSR), a dimeric ribonuclease shown to have antiviral activity against intracellular forms of HIV-1 (R. J. Youle et al., 1994, Proc. Natl. Acad. Sci. USA, 91:6012–6016). These results support the hypothesis that there are regions of primary sequence unique to EDN (and shared at least somewhat with ECP) that are necessary to promote this antiviral effect.

Table 7 shows antiviral activity of other RNase A superfamily ribonucleases. Antiviral activity was measured via the quantitative shell vial assay, and ribonuclease activity by generation of acid soluble ribonucleotides from acid insoluble tRNA substrate. Baseline ribonuclease activity measured in the absence of added ribonuclease was 0.6 pmol/m.

TABLE 7

| RNase | concentration (nM) | infectious units/ml +/- sd | rnase activity (pmol/m) |
|---|---|---|---|
| RNase A | 0 | 2480 +/- 66 | 114 |
| | 25 | 2423 +/- 230 | |
| | 50 | 2502 +/- 65 | |
| | 100 | 2482 +/- 140 | |
| BSR[a] | 0 | 3900 +/- 219 | 80 |
| | 25 | 4035 +/- 147 | |
| | 50 | 4015 +/- 58 | |
| | 100 | 3995 +/- 139 | |
| RNase k6 | 0 | 2480 +/- 66 | 20 |
| | 25 | 2313 +/- 206 | |
| | 50 | 2288 +/- 62 | |
| | 100 | 2485 +/- 111 | |

[a]BSR = bovine seminal ribonuclease

Specific interaction between EDN and extracellular virions of RSV: The antiviral activity of rhEDN was evaluated in the presence of increasing concentrations of the ribonucleolytically-inactivated point mutant, rhEDNdK$^{38}$. As shown above, this form of inactivated rhEDN has no antiviral activity in this assay. Table 8 shows that rhEDN's antiviral activity is blocked by increasing concentrations of rhEDNdK$^{38}$. In contrast, increasing concentrations of rhRNase k6, a related, ribonucleolytically active protein with no demonstrable antiviral activity (Table 7), had no effect on the antiviral activity of rhEDN.

Table 8 shows antiviral activity of rhEDN in the presence of rhEDNdK$^{38}$ or rhRK6. Antiviral activity against extracellular virions of RSV-B was measured by quantitative shell vial assay. Double asterisk (**) indicates that value differs significantly from baseline (0 nM) at the p<0.01 level.

TABLE 8

| rhEDN (nM) | rhEDNdK$^{38}$ (nM) | infectious units/ml (+/- sd) |
|---|---|---|
| 0 | 0 | 5625 +/- 220 |
| 0 | 1000 | 5698 +/- 324 |
| 200 | 0 | 573 +/- 126** |
| 200 | 200 | 3273 +/- 167 |
| 1000 | 200 | 2482 +/- 315 |
| | rhRK6 (nM) | |
| 0 | 0 | 6380 +/- 145 |
| 0 | 1000 | 6205 +/- 318 |
| 200 | 0 | 522 +/- 46** |
| 200 | 200 | 626 +/- 37** |
| 200 | 1000 | 502 +/- 114** |

Antiviral activity of human/owl monkey EDN chimeras: As an initial step toward identifying the region or regions of EDN that are crucial for interaction with RSV, two chimeras were assembled utilizing complementary regions of human and owl monkey EDNs, as shown in FIG. 19. Analysis of the antiviral effects of each chimera is shown in Table 9. Chimera OR5 has low-level ribonucleolytic activity, and, not surprisingly, has no measurable antiviral activity. Interestingly, chimera EG5, has ribonuclease activity that is nearly as potent as human EDN, but has only slight antiviral activity, suggesting the presence of a crucial region or regions somewhere within the first fifty residues of human EDN.

Table 9 shows antiviral activity of human/owl monkey EDN chimera& Antiviral activity was measured via the quantitative shell vial assay. Single asterisk (*) indicates that value differs significantly from baseline (0 nM) at the p<0.05 level. Ribonuclease activity was measured as generation of acid soluble ribonucleotides from acid insoluble tRNA substrate. Baseline ribonuclease activity measured in the absence of added EDN is 0.6 pmol/m.

TABLE 9

| chimera (pmol/m) | concentration (nM) | infectious units/ml +/- sd | rnase activity |
|---|---|---|---|
| OR5 | 0 | 5112 +/- 415 | 5 |
| | 100 | 5615 +/- 690 | |
| EG5 | 0 | 5112 +/- 415 | 20 |
| | 25 | 5717 +/- 755 | |
| | 50 | 5247 +/- 420 | |
| | 100 | 2641 +/- 539* | |

Discussion

This Example shows that the emergence of antiviral activity parallels acquisition of enhanced ribonuclease activity among EDN genes, as both features emerge some time after the divergence of the Old World from the New World monkey species. Interestingly, Zhang and colleagues evaluated the evolutionary history of the analogous set of primate genes encoding ECP, and concluded that ECP's antimicrobial function was acquired as a result of positive (Darwinian) selection at the molecular level (J. Zhang et al., 1998, Proc. Natl. Acad. Sci. USA, 95:3708–3713). The mathematical analysis shown here (Table 6) does not provide definitive support for positive selection with respect to the antiviral function of EDN; however, the conclusions from this type of analysis are based on the assumption that mutations that do not alter the protein sequence occur freely and at random. While this may be the case for some genes, it is likely to be an oversimplification; for instance, several groups have shown that sequences with elevated rates of non-silent mutations also tend to have elevated rates of silent mutations (D. Mouchiroud et al., 1995, J. Mol. Evol., 40:107–113; K. H. Wolfe and P. M. Sharp, 1993, J. Mol. Evol., 37:441–456; A. Ticher and D. Graur, 1989, J. Mol. Evol., 28:286–298), and others have suggested a correlation between rates of synonymous substitution and nucleotide and/or amino acid composition (K. H. Wolfe et al., 1989, Nature, 337:283–285; D. Graur, 1985, J. Mol. Evol., 22:53–62; X. Gu and W.-H. Li, 1994, J. Mol. Evol., 38:468–475). A clearer understanding of the evolutionary constraints promoting both silent and non-silent mutations both in general and for individual protein coding sequences may ultimately result in a reassessment of the conclusions drawn here.

Perhaps the most important findings presented here are those that address the mechanism of EDN's antiviral activity. The previous Examples showed that ribonuclease activity was crucial to the antiviral effect, but that it was not sufficient to explain EDN's apparent unique activity among the RNase A ribonucleases. This Example shows that EDN's antiviral activity is specifically blocked by increasing concentrations of a ribonucleolytically-inactivated point mutant of EDN, rhEDNdK$^{38}$, while similar concentrations of ribonucleolytically active, but antivirally-inactive human RNase k6 had no effect whatsoever. The implications of this result reach out in many directions. The presence of specific, saturable binding suggests physiologic relevance, and stands in greatest support of the hypotheses regarding the physiologic function of EDN and the double-edged sword of eosinophilic inflammation. In terms of mechanism, identification and characterization of the elements of specificity, both within EDN and within the as-yet-to-be-identified viral surface target(s), may provide some insight into the way in which EDN successfully penetrates the viral capsid and gains access to the viral RNA genome. As most antiviral agents in current use function by inhibiting replication of virions intracellularly, information on how and where one might attack virions extracellularly might ultimately be harnessed toward the creation of a novel class of antiviral agents.

Example 7

Anti-viral Activity of EDN in Tissue Culture

This Example shows that an eosinophil-derived ribonuclease can exhibit anti-viral activity in a tissue culture model. HEp-2 human respiratory epithelial cells were grown in culture to 50% confluency. At time zero, the cultures were infected with RSV at a multiplicity of infection of 0.1. Unincorporated viral particles were removed after 2 hours. At this 2 hour time point, and again every 24 hours thereafter, baculovirus-derived human EDN or baculovirus-derived rhEDNdK38 were added to maintain a concentration of 50 nM, and syncytia formation was measured as an indicator of viral cytopathic effect. rhEDN, but not rhEDNdK$^{38}$, protected the human respiratory epithelial cells from viral infection as determined at 6 days.

What is claimed is:

1. A method for inactivating a virion of an enveloped single-stranded RNA virus of the family Paramyxoviridae comprising contacting the virion with an eosinophil-derived ribonuclease, a fragment thereof or a pharmaceutically acceptable salt thereof.

2. The method of claim 1, wherein the eosinophil-derived ribonuclease is eosinophil-derived neurotoxin (EDN) or eosinophil cationic protein (ECP).

3. The method of claim 1, wherein the eosinophil-derived ribonuclease is a recombinant protein.

4. The method of claim 3, wherein the eosinpohil-derived ribonuclease is a human protein.

5. The method of claim 4, wherein the eosinophil-derived ribonuclease comprises the amino acid sequence shown in SEQ ID NO:7 or SEQ ID NO:10.

6. The method of claim 1, wherein the member of the Paramyxoviridae family is respiratory syncytial virus (RSV) or parainfluenza virus (PIV).

7. An aerosolizer device for delivery of a pharmaceutical composition comprising eosinophil-neurotoxin (EDN), a fragment thereof, or a pharmaceutically acceptable salt thereof in a pharmaceutically effective amount for treating a subject infected by an enveloped single-stranded RNA virus of the family Paramyxoviridae, and a pharmaceutically acceptable carrier.

8. The aerosolizer device of claim 7, wherein the carrier is suitable for aerosol administration.

9. The composition of claim 7, wherein the eosinophil-derived neurotoxin (EDN) is a recombinant protein.

10. The composition of claim 7, wherein the eosinophil-derived neurotoxin (EDN) is a human protein.

11. The composition of claim 10, wherein the eosinophil-derived neurotoxin comprises the amino acid sequence shown in SEQ ID NO:7 or SEQ ID NO:10.

12. A method for treating a subject infected by an enveloped single-stranded RNA virus of the family Paramyxoviridae comprising administering to the subject an effective amount of an eosinophil-derived ribonuclease, a fragment thereof or a pharmaceutically acceptable salt thereof, wherein said administering is parenteral or by aerosol.

13. A method according to claim 12, wherein the eosinophil-derived ribonuclease is a human protein.

14. The method of claim 12, wherein the eosinophil-derived ribonuclease comprises the amino acid sequence shown in SEQ ID NO:7 or SEQ ID NO:10.

15. A method according to claim 12, wherein the eosinophil-derived ribonuclease is a eosinophil cationic protein.

* * * * *

```
                              SEQUENCE LISTING

<160> NUMBER OF SEQ ID NOS:  11

<210> SEQ ID NO 1
<211> LENGTH: 20
<212> TYPE: DNA
<213> ORGANISM: respiratory syncytial virus

<400> SEQUENCE: 1
actcatccaa acaacccaca                                                    20

<210> SEQ ID NO 2
<211> LENGTH: 20
<212> TYPE: DNA
<213> ORGANISM: respiratory syncytial virus

<400> SEQUENCE: 2
ggracaaawt tgaacacttc                                                    20

<210> SEQ ID NO 3
<211> LENGTH: 21
<212> TYPE: DNA
<213> ORGANISM: Escherichia coli

<400> SEQUENCE: 3
gggccgcaag aaaactatcc c                                                  21

<210> SEQ ID NO 4
<211> LENGTH: 21
<212> TYPE: DNA
<213> ORGANISM: Escherichia coli

<400> SEQUENCE: 4
aactggaagt cgccgcgcca c                                                  21

<210> SEQ ID NO 5
<211> LENGTH: 134
<212> TYPE: PRT
<213> ORGANISM: Homo sapiens

<400> SEQUENCE: 5

Lys Pro Pro Gln Phe Thr Trp Ala Gln Trp Phe Glu Thr Gln His Ile
  1               5                  10                  15

Asn Met Thr Ser Gln Gln Cys Thr Asn Ala Met Gln Val Ile Asn Asn
             20                  25                  30

Tyr Gln Arg Arg Cys Lys Asn Gln Asn Thr Phe Leu Leu Thr Thr Phe
         35                  40                  45

Ala Asn Val Val Asn Val Cys Gly Asn Pro Asn Met Thr Cys Pro Ser
     50                  55                  60
```

```
Asn Lys Thr Arg Lys Asn Cys His His Ser Gly Ser Gln Val Pro Leu
 65                  70                  75                  80

Ile His Cys Asn Leu Thr Thr Pro Ser Pro Gln Asn Ile Ser Asn Cys
                 85                  90                  95

Arg Tyr Ala Gln Thr Pro Ala Asn Met Phe Tyr Ile Val Ala Cys Asp
            100                 105                 110

Asn Arg Asp Gln Arg Arg Asp Pro Pro Gln Tyr Pro Val Val Pro Val
        115                 120                 125

His Leu Asp Arg Ile Ile
    130
```

<210> SEQ ID NO 6
<211> LENGTH: 131
<212> TYPE: PRT
<213> ORGANISM: Aotus trivirgatus

<400> SEQUENCE: 6

```
Ala Pro Gln Lys Phe Thr Arg Ala Gln Trp Phe Ser Ile Gln His Ile
  1               5                  10                  15

Gln Thr Thr Pro Leu Arg Cys Thr Asn Ala Met Arg Ala Ile Asn Lys
                 20                  25                  30

Tyr Gln His Arg Cys Lys Asn Gln Asn Thr Phe Leu His Thr Thr Phe
             35                  40                  45

Ala Ala Val Val Asn Val Cys Gly Asn Thr Asn Ile Thr Cys Pro Arg
     50                  55                  60

Asn Ala Ser Leu Asn Asn Cys His His Ser Arg Val Gln Val Pro Leu
 65                  70                  75                  80

Thr Tyr Cys Asn Leu Thr Gly Pro Pro Thr Ile Thr Asn Cys Val Tyr
                 85                  90                  95

Ser Ser Thr Gln Ala Asn Met Phe Tyr Val Val Ala Cys Asp Asn Arg
            100                 105                 110

Asp Gln Arg Asp Pro Pro Gln Tyr Pro Val Val Pro Val His Leu Asp
        115                 120                 125

Thr Thr Ile
    130
```

<210> SEQ ID NO 7
<211> LENGTH: 152
<212> TYPE: PRT
<213> ORGANISM: Homo sapiens

<400> SEQUENCE: 7

```
Ser Lys Pro Pro Gln Phe Thr Trp Ala Gln Trp Phe Glu Thr Gln His
  1               5                  10                  15

Ile Asn Met Thr Ser Gln Gln Cys Thr Asn Ala Met Gln Val Ile Asn
                 20                  25                  30

Asn Tyr Gln Arg Arg Cys Lys Asn Gln Asn Thr Phe Leu Leu Thr Thr
             35                  40                  45

Phe Ala Asn Val Val Asn Val Cys Gly Asn Pro Asn Met Thr Cys Pro
     50                  55                  60

Ser Asn Lys Thr Arg Lys Asn Cys His His Ser Gly Ser Gln Val Pro
 65                  70                  75                  80

Leu Ile His Cys Asn Leu Thr Thr Pro Ser Pro Gln Asn Ile Ser Asn
                 85                  90                  95

Cys Arg Tyr Ala Gln Thr Pro Ala Asn Met Phe Tyr Ile Val Ala Cys
            100                 105                 110
```

```
Asp Asn Arg Asp Gln Arg Arg Asp Pro Pro Gln Tyr Pro Val Val Pro
            115                 120                 125

Val His Leu Asp Arg Ile Ile Glu Phe Pro Gly Thr Arg Ser Val Asp
    130                 135                 140

Asp Tyr Lys Asp Asp Asp Asp Lys
145                 150
```

<210> SEQ ID NO 8
<211> LENGTH: 709
<212> TYPE: DNA
<213> ORGANISM: Homo sapiens

<400> SEQUENCE: 8

```
gctggatcag ttctcacagg agctacagcg cggagactgg gaaacatggt tccaaaactg      60
ttcacttccc aaatttgtct gcttcttctg ttggggcttc tggctgtgga gggctcactc     120
catgtcaaac ctccacagtt tacctgggct caatggtttg aaacccagca catcaatatg     180
acctcccagc aatgcaccaa tgcaatgcag gtcattaaca attatcaacg gcgatgcaaa     240
aaccaaaata ctttccttct tacaactttt gctaacgtag ttaatgtttg tggtaaccca     300
aatatgacct gtcctagtaa caaaactcgc aaaaattgtc accacagtgg aagccaggtg     360
ccttttaatcc actgtaacct cacaactcca agtccacaga atatttcaaa ctgcaggtat     420
gcgcagacac cagcaaacat gttctatata gttgcatgtg acaacagaga tcaacgacga     480
gaccctccac agtatccggt ggttccagtt cacctggata gaatcatcta agctcctgta     540
tcagcactcc tcatcatcac tcatctgcca agctcctcaa tcatagccaa gatcccatct     600
ctccatatac tttgggtatc agcatctgtc ctcatcagtc tccataccc ttcagctttc      660
ctgagctgaa gtgccttgtg aaccctgcaa taaactgctt tgcaaattc                 709
```

<210> SEQ ID NO 9
<211> LENGTH: 537
<212> TYPE: DNA
<213> ORGANISM: Homo sapiens

<400> SEQUENCE: 9

```
atggttccaa aactgttcac ttcccaaatt tgtctgcttc ttctgttggg gcttctggct      60
gtggagggct cactccatgt caaacctcca cagtttacct gggctcaatg gtttgaaacc     120
cagcacatca atatgacctc ccagcaatgc accaatgcaa tgcaggtcat taacaattat     180
caacggcgat gcaaaaacca aaatactttc cttcttacaa cttttgctaa cgtagttaat     240
gtttgtggta acccaaatat gacctgtcct agtaacaaaa ctcgcaaaaa ttgtcaccac     300
agtggaagcc aggtgccttt taatccactg taacctcaca ctccaagtcc acagaatatt     360
tcaaactgca ggtatgcgca gacaccagca aacatgttct atatagttgc atgtgacaac     420
agagatcaac gacgagaccc tccacagtat ccggtggttc cagttcacct ggatagaatc     480
atcgaattgc cgggtaccag atctgtcgac gactacaagg acgatgacga caagtga       537
```

<210> SEQ ID NO 10
<211> LENGTH: 178
<212> TYPE: PRT
<213> ORGANISM: Homo sapiens

<400> SEQUENCE: 10

```
Met Val Pro Lys Leu Phe Thr Ser Gln Ile Cys Leu Leu Leu Leu Leu
  1               5                  10                  15
```

```
Gly Leu Leu Ala Val Glu Gly Ser Leu His Val Lys Pro Pro Gln Phe
                20                  25                  30

Thr Trp Ala Gln Trp Phe Glu Thr Gln His Ile Asn Met Thr Ser Gln
            35                  40                  45

Gln Cys Thr Asn Ala Met Gln Val Ile Asn Asn Tyr Gln Arg Arg Cys
        50                  55                  60

Lys Asn Gln Asn Thr Phe Leu Leu Thr Thr Phe Ala Asn Val Val Asn
 65                  70                  75                  80

Val Cys Gly Asn Pro Asn Met Thr Cys Pro Ser Asn Lys Thr Arg Lys
                    85                  90                  95

Asn Cys His His Ser Gly Ser Gln Val Pro Leu Ile His Cys Asn Leu
                100                 105                 110

Thr Thr Pro Ser Pro Gln Asn Ile Ser Asn Cys Arg Tyr Ala Gln Thr
            115                 120                 125

Pro Ala Asn Met Phe Tyr Ile Val Ala Cys Asp Asn Arg Asp Gln Arg
        130                 135                 140

Arg Asp Pro Pro Gln Tyr Pro Val Val Pro Val His Leu Asp Arg Ile
145                 150                 155                 160

Ile Glu Phe Pro Gly Thr Arg Ser Val Asp Asp Tyr Lys Asp Asp Asp
                165                 170                 175

Asp Lys

<210> SEQ ID NO 11
<211> LENGTH: 134
<212> TYPE: PRT
<213> ORGANISM: Artificial Sequence
<220> FEATURE:
<223> OTHER INFORMATION: Description of Artificial Sequence: Inferred
      Primate Ancestral Sequence
<223> OTHER INFORMATION: 12, 17, 18, 21, 22, 29, 32, 35, 45, 58, 60, 65,
      66, 67, 73, 81, 82, 86, 87, 88, 91, 92, 97, 99,
      100, 102, and 116 comprise Non-informative sites
      of inferred ancestral sequence

<400> SEQUENCE: 11

Lys Pro Pro Gln Phe Thr Trp Ala Gln Trp Phe Xaa Ile Gln His Ile
 1               5                  10                  15

Xaa Xaa Thr Pro Xaa Xaa Cys Thr Asn Ala Met Arg Xaa Ile Asn Xaa
                20                  25                  30

Tyr Gln Xaa Arg Cys Lys Asn Gln Asn Thr Phe Leu Xaa Thr Thr Phe
            35                  40                  45

Ala Asp Val Val Asn Val Cys Gly Asn Xaa Asn Xaa Thr Cys Pro Arg
        50                  55                  60

Xaa Xaa Xaa Leu Asn Asn Cys His Xaa Ser Gly Val Gln Val Pro Leu
 65                  70                  75                  80

Xaa Xaa Cys Asn Leu Xaa Xaa Xaa Gly Pro Xaa Xaa Ile Ser Asn Cys
                    85                  90                  95

Xaa Tyr Xaa Xaa Thr Xaa Ala Asn Met Phe Tyr Val Val Ala Cys Asp
                100                 105                 110

Asn Arg Asp Xaa Arg Arg Asp Pro Pro Gln Tyr Pro Val Val Pro Val
            115                 120                 125

His Leu Asp Thr Ile Ile
            130
```